US011235045B2

(12) United States Patent
Milich et al.

(10) Patent No.: US 11,235,045 B2
(45) Date of Patent: Feb. 1, 2022

(54) HYBRID HEPADNAVIRUS CORES CARRYING MULTIPLE MALARIA PARASITE EPITOPES

(71) Applicant: VLP Biotech, Inc., San Diego, CA (US)

(72) Inventors: David R. Milich, Escondido, CA (US); David C. Whitacre, San Diego, CA (US)

(73) Assignee: VLP Biotech, Inc., San Diego, CA (US)

( * ) Notice: Subject to any disclaimer, the term of this patent is extended or adjusted under 35 U.S.C. 154(b) by 272 days.

(21) Appl. No.: 16/175,681

(22) Filed: Oct. 30, 2018

(65) Prior Publication Data

US 2019/0209672 A1     Jul. 11, 2019

Related U.S. Application Data

(63) Continuation of application No. PCT/US2017/030475, filed on May 1, 2017.

(60) Provisional application No. 62/330,137, filed on Apr. 30, 2016.

(51) Int. Cl.
    *A61K 39/015*     (2006.01)
    *A61P 33/06*     (2006.01)
    *C12Q 1/70*     (2006.01)
    *A61K 39/29*     (2006.01)
    *A61K 39/295*     (2006.01)

(52) U.S. Cl.
    CPC ............ *A61K 39/015* (2013.01); *A61K 39/29* (2013.01); *A61K 39/295* (2013.01); *A61P 33/06* (2018.01); *C12Q 1/701* (2013.01)

(58) Field of Classification Search
None
See application file for complete search history.

(56) References Cited

U.S. PATENT DOCUMENTS

| 6,942,866 | B2 | 9/2005 | Birkett | |
| 7,144,712 | B2 * | 12/2006 | Milich | A61K 39/12 435/69.3 |
| 7,320,795 | B2 * | 1/2008 | Milich | A61K 39/12 424/189.1 |
| 7,811,576 | B2 * | 10/2010 | Milich | A61K 39/292 424/189.1 |

(Continued)

FOREIGN PATENT DOCUMENTS

| WO | WO-2005011571 A2 | 2/2005 | |
| WO | WO2014/144775 | * 9/2014 | ............ A61K 39/29 |

OTHER PUBLICATIONS

Alloueche et al., (2003). "Protective Efficacy Of the RTS,S/AS02 Plasmodium Falciparum Malaria Vaccine is Not Strain Specific," Am J Trop Med Hyg., 68:97-101.

(Continued)

*Primary Examiner* — Agnieszka Boesen
(74) *Attorney, Agent, or Firm* — Morrison & Foerster LLP

(57) ABSTRACT

The present disclosure relates to rodent hepadnavirus core antigens including one or more B cell and T cell epitopes of a malaria parasite antigen. More specifically, the present disclosure relates to hybrid woodchuck hepadnavirus core antigens that have been modified to diminish the antibody response to the core antigen so as to enhance the antibody response to fragments of malaria antigen(s) included therein.

20 Claims, 16 Drawing Sheets

Specification includes a Sequence Listing.

*P. falciparum* CS Protein Epitope Targets
seq. on hybrid sporozoite

Pf aa no.: 98     323

B cell epitopes
- K-rich (93-113)
- N1 (112-123)
- UTC (333-352)

CD4+ T cell epitopes
- Repeats (140-159) aka "Mal" (298-315)
- TH.3R (354-378)
- CS.T3 (378-392)

VLPs Constructed
WHc-Mal-78
WHc-Krich-78
WHc-N1(112-123)-78
WHc-(298-315)-78
WHc-Mal5-78

WHc-Mal-78-UTC
WHc-Mal-78-TH
WHc-Mal-78-3T
WHc-Ct-3T
WHc(C61S)-Mal-78-3T

WHc-Pv-78

New Pb/Pf-CSP-CT Sporozoites
(318-397 from *P. falciparum*)

(56) References Cited

U.S. PATENT DOCUMENTS

| | | | |
|---|---|---|---|
| 7,883,843 | B2* | 2/2011 | Milich .................. C07K 14/005 |
| | | | 435/5 |
| 10,213,501 | B2* | 2/2019 | Spiegel .................... A61P 33/06 |
| 10,300,124 | B2 | 5/2019 | Milich et al. |
| 2005/0208068 | A1 | 9/2005 | Milich et al. |
| 2016/0022801 | A1 | 1/2016 | Milich et al. |
| 2016/0039883 | A1 | 2/2016 | Milich et al. |

OTHER PUBLICATIONS

Alonso et al., (2004). "Efficacy of the RTS,S/AS02A vaccine against Plasmodium falciparum infection and disease in young African children: randomised controlled trial," Lancet, 364:1411-1420.

Alper, (2005). "The human immune response to hepatitis B surface antigen," Exp Clin Immunogenet., 12:171-181.

Aponte et al., (2007). "Safety of the RTS,S/AS02D candidate malaria vaccine in infants living in a highly endemic area of Mozambique: a double blind randomised controlled phase I/IIb trial," Lancet, 370:1543-1551, 9 pages.

Betancourt et al., (2007). "Phase I clinical trial in healthy adults of a nasal vaccine candidate containing recombinant hepatitis B surface and core antigens," Int J Infect Dis., 11:394-401.

Billaud et al., (2005). "Combinatorial Approach to Hepadnavirus-Like Particle Vaccine Design," J Virol, 79:13656-13666.

Billaud et al., (2007). "Advantages to the use of rodent hepadnavirus core proteins as vaccine platforms," Vaccine, 25:1593-1606, 23 pages.

Birkett et al., (2002). "A modified hepatitis B virus core particle containing multiple epitopes of the Plasmodium falciparum circumsporozoite protein provides a highly immunogenic malaria vaccine in preclinical analyses in rodent and primate hosts," Infect Immun., 70:6860-6870.

Bojang et al., (2001). "Efficacy of RTS,S/AS02 malaria vaccine against Plasmodium falciparum infection in semi-immune adult men in The Gambia: a randomised trial," Lancet, 358:1927-1934.

Bruna-Romero et al., (2001). "Detection of malaria liver-stages in mice infected through the bite of a single Anopheles mosquito using a highly sensitive real-time PCR," Int J Parasitol., 31:1499-1502.

Calle et al., (1992). "Recognition of different domains of the Plasmodium falciparum CS protein by the sera of naturally infected individuals compared with those of sporozoite-immunized volunteers," J Immunol., 149:2695-2701.

Gerami et al., (1992). "The basolateral domain of the hepatocyte plasma membrane bears receptors for the circumsporozoite protein of plasmodium falciparum sporozoites," Cell, 70:1021-1033.

Cockburn et al., (2011). "Dendritic Cells and Hepatocytes Use Distinct Pathways to Process Protective Antigen from Plasmodium in vivo," PLoS Pathog., 7:e1001318, 10 pages.

Cohen et al., (1998). "Sequence comparison of woodchuck hepatitis virus replicative forms shows conservation of the genome," Virology, 162:12-20.

Conway et al., (1997). "Visualization of a 4-helix bundle in the hepatitis B virus capsid by cryo-electron microscopy," Nature, 386:91-94.

Crosnier et al., (2011). "BASIGIN is a receptor essential for erythrocyte invasion by Plasmodium falciparum," Nature, 480:534-537, 13 pages.

Dakappagari et al., (2003). "A Chimeric Multi-Human Epidermal Growth Factor Receptor-2 B Cell Epitope Peptide Vaccine Mediates Superior Antitumor Responses," J Immunol, 170:4242-4253.

Douglas et al., (2015). "A PfRH5-Based Vaccine is Efficacious against Heterologous Strain Blood-Stage Plasmodium falciparum Infection in Aotus Monkeys," Cell Host Microbe, 17:130-139.

Duffy et al., (2012). "Pre-erythrocytic malaria vaccines: identifying the targets," Expert Rev Vaccines, 11:1261-1280, 32 pages.

Espinosa et al., (2013). "Development of a Chimeric Plasmodium berghei Strain Expressing the Repeat Region of the P. vivax Circumsporozoite Protein for In Vivo Evaluation of Vaccine Efficacy," Infect Immun., 81:2882-2887.

Espinosa et al., (2015). "Proteolytic Cleavage of the Plasmodium falciparum Circumsporozoite Protein is a Target of Protective Antibodies," J Infect Dis, 212:1111-1119.

Good et al., (1986). "Genetic control of the immune response in mice to a Plasmodium falciparum sporozoite vaccine. Widespread nonresponsiveness to single malaria T epitope in highly repetitive vaccine," J Exp Med., 164:655-660.

Good et al., (1988). "Human T-cell recognition of the circumsporozoite protein of Plasmodium falciparum: immunodominant T-cell domains map to the polymorphic regions of the molecule," Proc Natl Acad Sci., 85:1199-1203.

Gordon et al., (1995). "Safety, immunogenicity, and efficacy of a recombinantly produced Plasmodium falciparum circumsporozoite protein-hepatitis B surface antigen subunit vaccine," J Infect Dis., 171:1576-1585.

Greenstein et al., (1992). "A universal T cell epitope-containing peptide from hepatitis B surface antigen can enhance antibody specific for HIV gp120," J Immunol, 148:3970-3977.

International Preliminary Report on Patentability received for PCT Patent Application No. PCT/US2017/030475, dated Nov. 15, 2018, 5 pages.

International Search Report and Written Opinion Received for PCT Patent Application No. PCT/US17/30475, dated Jul. 21, 2017, 5 Pages.

Kaba et al., (2012). "Protective Antibody and CD8+ T-Cell Responses to the Plasmodium falciparum Circumsporozoite Protein Induced by a Nanoparticle Vaccine," PLoS One, 7:e48304, 11 pages.

Kastenmuller et al., (2013). "Full-Length Plasmodium falciparum Circumsporozoite Protein Administered with Long-Chain Poly(I-C) or the Toll-Like Receptor 4 Agonist Glucopyranosyl Lipid Adjuvant-Stable Emulsion Elicits Potent Antibody and CD4+ T Cell Immunity and Protection in Mice," Infect Immun., 81:789-800.

Kumar et al., (2006). "The circumsporozoite protein is an immunodominant protective antigen in irradiated sporozoites," Nature, 444:937-940.

Lee et al., (2009). "Interaction of the hepatitis B core antigen and the innate immune system," J Immunol., 182:6670-6681.

Menard et al., (1997). "Gene Targeting in Malaria Parasites," Methods, 13:148-157.

Milich et al., (1986). "The nucleocapsid of hepatitis B virus is both a T-cell-independent and a T-cell-dependent antigen," Science, 234:1398-1401.

Milich et al., (1997). "Role of B cells in antigen presentation of the hepatitis B core," Proc Natl Acad Sci USA, 94:14648-14653.

Milich et al., (2002). "Conversion of poorly immunogenic malaria repeat sequences into a highly immunogenic vaccine candidate," Vaccine, 20:771-788.

Neafsey et al., (2015). "Genetic diversity and protective efficacy of the RTS,S/AS01 malaria vaccine," N Engl J Med, 373:2025-2037.

Olotu et al., (2013). "Four-Year Efficacy of RTS,S/AS01E and Its Interaction with Malaria Exposure," N Engl J Med, 368:1111-1120.

Ord et al., (2014). "A malaria vaccine candidate based on an epitope of the Plasmodium falciparum RH5 protein," Malar J., 13:326. 9 pages.

Persson et al., (2002). "Cutting edge: a new tool to evaluate human pre-erythrocytic malaria vaccines: rodent parasites bearing a hybrid Plasmodium falciparum circumsporozoite protein," J Immunol., 169:6681-6685.

Plassmeyer et al., (2009). "Structure of the Plasmodium falciparum circumsporozoite protein, a leading malaria vaccine candidate," J Biol Chem, 284:26951-26963.

Porter et al., (2013). "Transgenic parasites stably expressing full-length Plasmodium falciparum circumsporozoite protein as a model for vaccine down-selection in mice using sterile protection as an endpoint," Clin Vaccine Immunol., 20:803-810.

Przysiecki et al., (2012). "Sporozoite neutralizing antibodies elicited in mice and rhesus macaques immunized with a Plasmodium falciparum repeat peptide conjugated to meningococcal outer membrane protein complex," Front Cell Infect Microbiol., 2:146, 11 pages.

Rathore et al., (2005). "An immunologically cryptic epitope of Plasmodium falciparum circumsporozoite protein facilitates liver

(56) References Cited

OTHER PUBLICATIONS cell recognition and induces protective antibodies that block liver cell invasion," J Biol Chem., 280:20524-9.

Schodel et al., (1992). "The position of heterologous epitopes inserted in hepatitis B virus core particles determines their immunogenicity," J Virol, 66:106-114.

Schodel et al., (1994). "Immunity to malaria elicited by hybrid hepatitis B virus core particles carrying circumsporozoite protein epitopes," J Exp Med, 180:1037-1046.

Schodel et al., (1997). "Immunization with hybrid hepatitis B virus core particles carrying circumsporozoite antigen epitopes protects mice against Plasmodium yoelii challenge," Behring Inst Mitt., (98):114-119.

Stoute et al., (1997). "A Preliminary Evaluation of a Recombinant Circumsporozoite Protein Vaccine against Plasmodium falciparum Malaria," N Engl J Med., 336:86-91.

Stoute et al., (1998). "Long-term efficacy and immune responses following immunization with the RTS,S malaria vaccine," J Infect Dis, 178:1139-1144.

Tewari et al., (2002). "Function of region I and II adhesive motifs of Plasmodium falciparum circumsporozoite protein in sporozoite motility and infectivity," J Biol Chem., 277:47613-8.

Walther et al., (2005). "Safety, immunogenicity and efficacy of a pre-erythrocytic malaria candidate vaccine, ICC-1132 formulated in Seppic ISA 720," Vaccine, 23:857-864.

Webster et al., (2005). "Enhanced T cell-mediated protection against malaria in human challenges by using the recombinant poxviruses FP9 and modified vaccinia virus Ankara," Proc Natl Acad Sci USA, 102:4836-4861.

Whitacre et al., (2015). "P. falciparum and P. vivax epitope-focused VLPs elicit sterile immunity to blood stage infections," PLoS One, 10(5):e0124856, 22 pages.

Whitacre et al., (2015). "Chapter 13: Use of VLPs in the Design of Malaria Vaccines," Viral Nanotechnology, pp. 209-231.

White et al., (1993). "Induction of cytolytic and antibody responses using Plasmodium falciparum repeatless circumsporozoite protein encapsulated in liposomes," Vaccine, 11:1341-1346.

White et al., (2013). "The Relationship between RTS,S Vaccine-Induced Antibodies, CD4+ T Cell Responses and Protection against Plasmodium falciparum Infection," PLoS One, 8:e61395, 10 pages.

Williams et al., (2012). "Enhancing Blockade of Plasmodium falciparum Erythrocyte Invasion Assessing Combinations of Antibodies against PfRH5 and Other Merozoite Antigens," PLoS Pathog., 8(11):e1002991, 15 pages.

Zavala et al., (1983). "Circumsporozoite proteins of malaria parasites contain a single immunodominant region with two or more identical epitopes," J Exp Med., 157:1947-1957.

Zavala et al., (1985). "Rationale for development of a synthetic vaccine against Plasmodium falciparum malaria," Science, 228:1436-1440.

* cited by examiner

*P. falciparum* CS Protein Epitope Targets
seq. on hybrid sporozoite

Pf aa no.: 98    323

N ▬▬▬▬▬▬▬▬▬▬▬▬▬▬▬▬▬▬ C

B cell epitopes:
- K-rich (93-113)
- N1 (112-123)
- Repeats (140-159) aka "Mal"

CD4+ T cell epitopes:
- (298-315)
- UTC (333-352)
- TH.3R (354-378)
- CS.T3 (378-392)

New Pb/Pf-CSP-CT Sporozoites (318-397 from *P. falciparum*)

FIG. 1A

VLPs Constructed

WHc-Mal-78
WHc-Krich-78
WHc-N1(112-123)-78
WHc-(298-315)-78
WHc-Mal5-78

WHc-Mal-78-UTC
WHc-Mal-78-TH
WHc-Mal-78-3T
WHc-Ct-3T
WHc(C61S)-Mal-78-3T

WHc-Pv-78

FIG. 1B

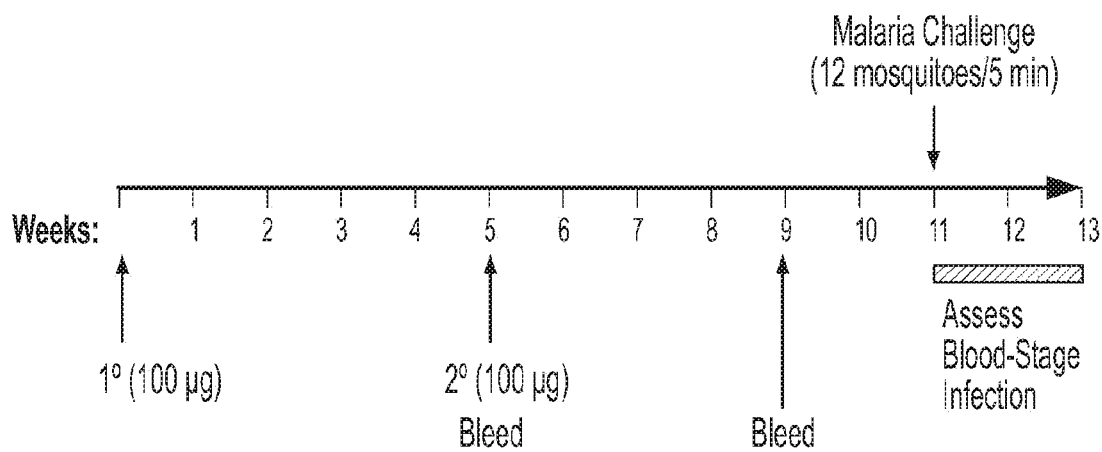
FIG. 6A
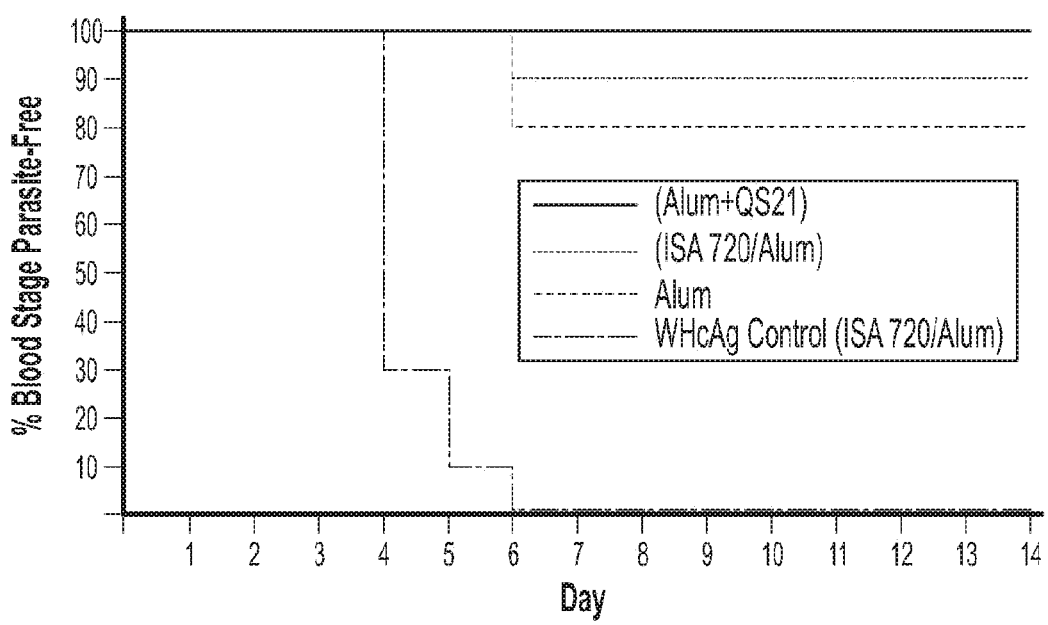
FIG. 6B
| Immunogen | Formulation (prime/boost) | Mice Challenged | Mice Infected | Protection | Mean Days Pre-patent |
|---|---|---|---|---|---|
| WHc(C61S)-Mal-78-3T | Alum/Alum | 10 | 2 | 80% | 6 |
| | Alum+QS-21/Alum+QS21 | 9 | 0 | 100% | - |
| | ISA 720/Alum | 10 | 1 | 90% | 6 |
| WHcAg | ISA 720/Alum | 10 | 10 | 0% | 4.4 |
FIG. 6C

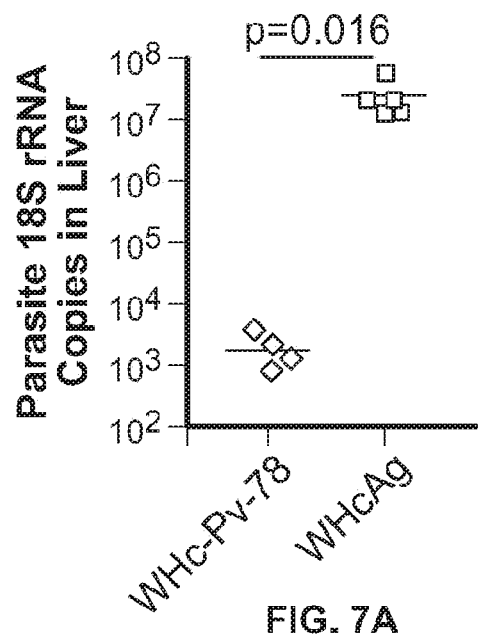
FIG. 7A
| Cohort | Infected/ challenged (mice) | Pre-patent period (days) | Protection |
|---|---|---|---|
| WHc-Pv-78 | 0/4 | - | 100% |
| WHcAg | 4/5 | 4.5 | 20% |
FIG. 7B
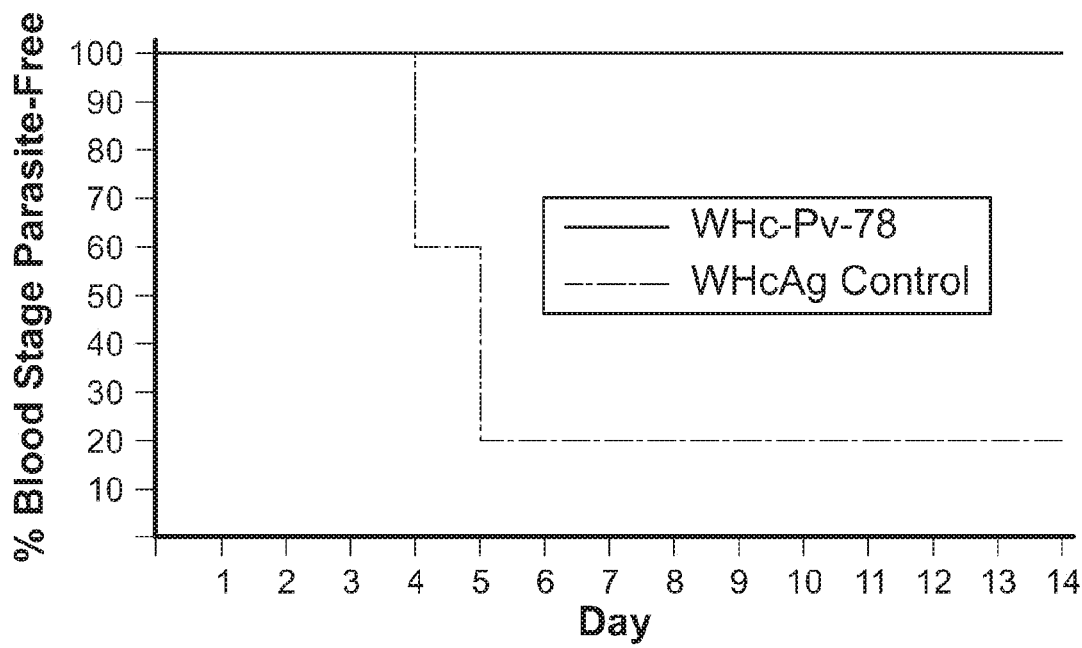
FIG. 7C Sequence of the hybrid CS protein

```
  1 MKKCTILVVA SLLLVNSLLP GYGQNKSIQA QRNLNELCYN EGNDNKLYHV  50
 51 LNSKNGKIYN RNTVNRLLAD APEGKKNEKK NEKIERNNKL KQPPPPPNPN 100
101 DPPPPNPNDP PPPNPNDPPP PNPNDPPPPN ANDPPPPNAN DPAPPNANDP 150
151 APPNANDPAP PNANDPAPPN ANDPPPPNPN DPAPPNANDP PPPNPNDPAP 200
201 PQGNNNPQPQ PRPQPQPQPQ PQPQPQPQPQ PRPQPQPQPG GNNNNKNNNN 250
251 DDSYIPSAEK ILEYLNKIQN SLSTEWSPCS VTCGNGIQVR IKPGSANKPK 300
301 DELDYENDIE KKICKMEKCS SVFNVVNSSI GLIMVLSFLF LN* 342
```

SEQ ID NO:21

FIG. 10A

|  | UTC | TH.3R | CS.T3 | |
|---|---|---|---|---|
| | EFVKQIRDSITEEWSQCNVT | C GSGIRVRKRKGSNKKAEDLTLEDI | DTE--ICKMDKCSSIFN | *P. berghei* SEQ ID NO:22 |
| | I.. I I.. III I II | I II II . II I I . | I I IIII.IIII. | |
| | EYLNKIQNSLSTEWSPCSVT | S GNGIQVRIKPGSANKPKDELDYEN | DIEKKICKMEKCSSV-- | SEQ ID NO:23 *P. falciparum* |
| Identical aa's: | 9/20 (45%) | 9/24 (38%) | 10/15 (67%) | |
| Similar aa's: | 13/20 (65%) | 11/24 (46%) | 12/15 (80%) | |

FIG. 10B

| Task | Selection Process | End-Point |
|---|---|---|
| 1. Select B cell epitopes | $(NANP)_4$, (NVDP), CS-non-repeats | α-Peptide binds CS protein and sporozoites |
| 1a. Epitope optimization | NANP-NVDP-$(NANP)_3$ | ++Antigenicity/immunogenicity |
| Select T cell epitopes | UTC; TH.3R; CS(CST3) | Th cell function in humans |
| Select molecular adjuvants | ssRNA | ++immunogenicity |
| 2. Produce construct | Combinatorial technology 17 insertion sites/21 C-termini | |
| 3. Transform *E.coli* with constructs (0.5 L culture volume) | Screen lysates (ELISAs) | |
| | Protein expression | 2-3 units |
| | Particle assembly | 3-4 units |
| | Epitope antigenicity | 3-4 units |
| 4. CS-WHcAg purification (5 L culture volume) | Assembly (1% agarose, CL-4B) Yield | Particulate ≥ 80 mg/L |
| 5. Biochemical/structural characterization | Particle size | 30-50 nm |
| | Electron microscopy | Formation of particle structures |
| | CD specra | WHcAg like (high alpha helix) |
| | Thermal stability | > 70°C |
| 6. Immunogenicity in mice | *In vivo* Ab Production | α-Insert titer of $10^6$-$10^7$ IgG isotypes, Ab persistence |
| | *In vitro/in vivo* Th cell activity (1 prime/1 boost) | + IL-2, + $IFN_\gamma$ |
| 7. In vitro immunofluoresence assay (IFA) on sporozoites | | IFA titer of $10^4$-$10^5$ |
| 8. In vivo protection liver/blood | a. Direct immunization/ challenge | CD4+/antibody % protection |
| | b. Passive transfer of antisera | only antibody % protection |

Selection criteria for improvements to the preliminary FLw-Mal-74-TH vaccine candidate and new vaccine particles.

FIG. 11

Comparison of WHc-CS Malaria VLP Vaccine Features to Previous-Generation Malaria VLP Vaccines RST,S and ICC-1132

| | | RST,S | WHc-CS | Apovia (ICC-1132) |
|---|---|---|---|---|
| Malaria | B epitopes | CS repeats: $(NANP)_{16}$ only | CS repeats (NANP and NVDP) | CS repeats (NANP and NVDP) |
| | T epitopes | CS, C-terminus 302-395 | CS 318-337 (UTC) CS 339-363 (TH-3R) CS 363-377 (CS.T3) | CS 318-337 |
| Carrier | | HBsAg (human pathogen) | WHcAg (full length) (nonhuman pathogen) | HBcAg (truncated) (human pathogen) |
| | | T cell dependent | T cell dependent or independent | T cell dependent or independent |
| | | 100-1000-fold less immunogenic in mice | 100-1000-fold more immunogenic in mice | 100-1000-fold more immunogenic in mice |
| | | Soluble HBsAg less immunogenic in humans | N.D. | Soluble HBcAg more immunogenic in humans |
| | | MHC nonresponder genotypes (mice and human) | No MHC nonresponders identified | No MHC nonresponders identified |
| | | Preexisting anti-HBs from HBV infection | Not relevant | Preexisting anti-HBc from HBV infection |
| | | Immune tolerance in HBV chronics | No Immune tolerance in HBV chronics | Immune tolerance in HBV chronics |
| | | N.D. | Δ carrier B cell sites | N.D. |
| | | N.D. | Replace spikes | N.D. |
| | | N.D. | Modify C-terminus | N.D. |

FIG. 12

| | | | |
|---|---|---|---|
| | Requires coexpression of HBsAg for HBsAg-CS assembly? | Self-assembly of WHc-CS | Self-assembly of HBc-CS |
| | Cannot express in bacteria<br>N.D. ? | Bacterial expression<br>Sterile immunity to blood stage in Tg sporozoite model | Bacterial expression<br>N.D. |
| Endogenous molecular adjuvants | None | ssRNA-TLR7/8 ligands | None |
| Stability to fixation | Lyophilization | Lyophilization | N.D. |
| Cold chain | Not required | Not required | N.D. |
| Formulation/adjuvants | Absolute requirement for immunostimulatory adjuvant (ASO1B, MPL/QS-21/oil/liposome) | Saline, alum, Montanide ISA-720 | Montanide ISA-720, alum |
| Phase II clinical results | 1-3 dose, 0 protection<br>3 dose + AS02A, 30%-50% | N.D.<br>N.D. | 1 dose, 0 protection<br>N.D. |

Note: Bold represents characteristics unique to WHc(C61S)-Mal-78-3T.

FIG. 12 (Cont.)

```
WHcAg      MDIDPYKEFGSSYQLLNFLPLDFFPDLNALVDTATALYEEELTGREHCSPHHTAIRQALV
WHcAgΔ2    MDIDPYKEFGSSYQLLNFLPADFFPAAAVLADTATALYEEELTGREHCSPHHTAIRQALV
WHcAgΔ3    MDIDPYKEFGSSYQLLNFLPLDFFPDLNALVDTATALYEEELTGREHCSPHHTAIRQALV
WHcAgΔ4    MDIDPYKEFGSSYQLLNFLPLDFFPDLNALVDTATALYEEELTGREHCSPHHTAIRQALV
WHcAgΔ5    MDIDPYKEFGSSYQLLNFLPLDFFPDLNALVDTATALYEEELTGREHCSPHHTAIRQALV
WHcAgΔ6    MDIDPYKEFGSSYQLLNFLPLDFFPDLNALVDTATALYEEELTGREHCSPHHTAIRQALV
WHcAgΔ7    MDIDPYKEFGSSYQLLNFLPLDFFPDLNALVDTATALYEEELTGREHCSPHHTAIRQALV
           ******************** ****    * *****************************

WHcAg      CWDELTKLIAWMSSNITSEQVRTIIVNHVNDTWGLKVRQSLWFHLSCLTFGQHTVQEFLV
WHcAgΔ2    CWDELTKLIAWMSSNITSEQVRTIIVNHVNDTWGLKVRQSLWFHLSCLTFGQHTVQEFLV
WHcAgΔ3    CWDELTKLIAWMSSNITSEQVRTIIVNHVNDTWGLKVRQSLWFHLSCLTFGQHTVQEFLV
WHcAgΔ4    SWDELTKLIAWMSSNITSEQVRTIIVNHVNDTWGLKVRQSLWFHLSCLTFGQHTVQEFLV
WHcAgΔ5    CXXXXXXXXXXXXXXXXXXXXXXXXXXHVNDTWGLKVRQSLWFHLSCLTFGQHTVQEFLV
WHcAgΔ6    CWDELTKLIAWMSSNITSEQVRTIIVNHVNDTWGLKVRQSLWFHLSCLTFGQHTVQEFLV
WHcAgΔ7    CWDELTKLIAWMSSAAAAAAAAAIIVNHVNDTWGLKVRQSLWFHLSCLTFGQHTVQEFLV
                                          *********************************

WHcAg      SFGVWIRTPAPYRPPNAPILSTLPEHTVIRRRGGARASRSPRRRTPSPRRRRSQSPRRRR
WHcAgΔ2    SFGVWIRTPAPYRPPNAPILSTLPEHTVIRRRGGARASRSPRRRTPSPRRRRSQSPRRRR
WHcAgΔ3    SFGVWIRTPAPYRPPPPPILSTLPEHTVIRRRGGARASRSPRRRTPSPRRRRSQSPRRRR
WHcAgΔ4    SFGVWIRTPAPYRPPNAPILSTLPEHTVIRRRGGARASRSPRRRTPSPRRRRSQSPRRRR
WHcAgΔ5    SFGVWIRTPAPYRPPNAPILSTLPEHTVIRRRGGARASRSPRRRTPSPRRRRSQSPRRRR
WHcAgΔ6    SFGVWIRTPAPYRPPNAPILSTLPEHTVIAAAGGAAASASPAAATPSPAAARSQSPAAAA
WHcAgΔ7    SFGVWIRTPAPYRPPNAPILSTLPEHTVIRRRGGARASRSPRRRTPSPRRRRSQSPRRRR
           ***************  ************   *** ** **   ****   *****

WHcAg      SQSPSANC (SEQ ID NO:1)
WHcAgΔ2    SQSPSANC (SEQ ID NO:2)
WHcAgΔ3    SQSPSANC (SEQ ID NO:3)
WHcAgΔ4    SQSPSANC (SEQ ID NO:4)
WHcAgΔ5    SQSPSANC (SEQ ID NO:5)
WHcAgΔ6    SQSPSANC (SEQ ID NO:6)
WHcAgΔ7    SQSPSANC (SEQ ID NO:7)
           ********
```

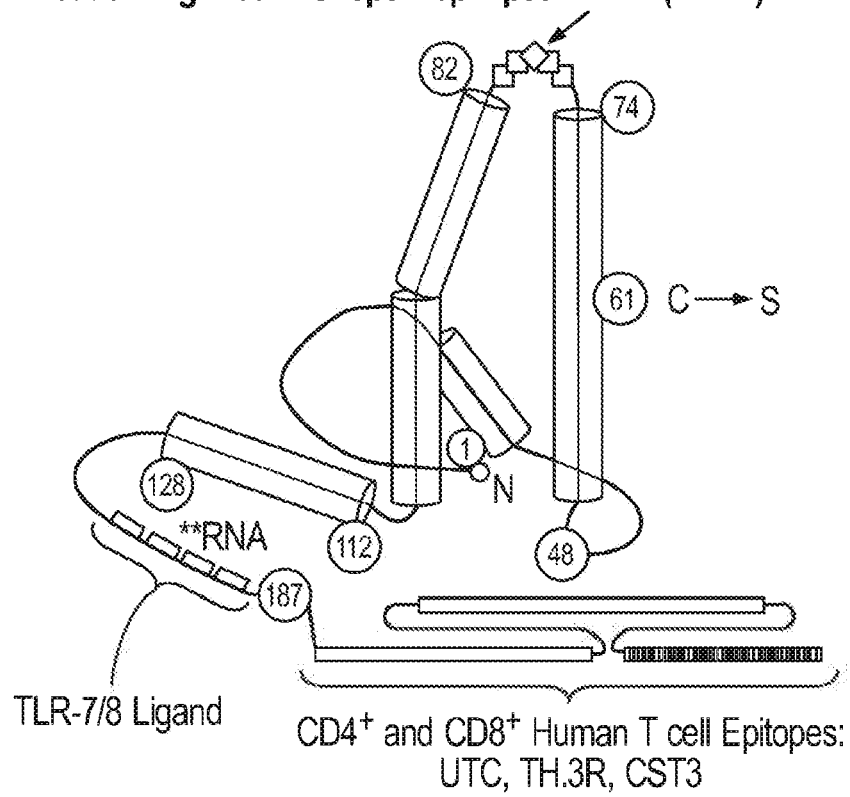

FIG. 14A

```
WHcAg    MDIDPYKEFGSSYQLLNFLPLDFFPDLNALVDTATALYEEELTGREHCSPHHTAIRQALV 60
VLP-162  MDIDPYKEFGSSYQLLNFLPLDFFPDLNALVDTATALYEEELTGREHCSPHHTAIRQALV 60
         ************************************************************

WHcAg    CWDELTKLIAWMSSNITS-----------------------EQVRTIIVNHVNDTWGLK 96
VLP-162  SWDELTKLIAWMSSNITSGILNANPNVDPNANPNANPNANPLEQVRTIIVNHVNDTWGLK 120
          *****************                       *******************

WHcAg    VRQSLWFHLSCLTFGQHTVQEFLVSFGVWIRTPAPYRPPNAPILSTLPEHTVIRRRGGAR 156
VLP-162  VRQSLWFHLSCLTFGQHTVQEFLVSFGVWIRTPAPYRPPNAPILSTLPEHTVIRRRGGAR 180
         ************************************************************

WHcAg    ASRSPRRRTPSPRRRRSQSPRRRRSQSPSANC---------------------------- 188
VLP-162  ASRSPRRGTPSPRRRRSQSPRRRRSQSPSANCDIEYLNKIQNSLSTEWSPCSVTSGNGIQ 240
         ******* ************************

WHcAg    ----------------------------------- 188 (SEQ ID NO:1)
VLP-162  VRIKPGSANKPKDELDYENDIEKKICKMEKCSSV  274 (SEQ ID NO:20)
```

FIG. 14B

```
WHcAg   MDIDPYKEFGSSYQLLNFLPLDFFPDLNALVDTATALYEEELTGREHCSPHHTAIRQALV  60
VLP-206 MDIDPYKEFGSSYQLLNFLPLDFFPDLNALVDTATALYEEELTGREHCSPHHTAIRQALV  60
        ************************************************************

WHcAg   CWDELTKLIAWMSSNITS-----------------------------------------E  79
VLP-206 CWDELTKLIAWMSSNITSGILDRADGQPAGDRADGQPAGDRAAGQPAGDRAAGQPAGDLE 120
        ******************                                         *

WHcAg   QVRTIIVNHVNDTWGLKVRQSLWFHLSCLTFGQHTVQEFLVSFGVWIRTPAPYRPPNAPI 139
VLP-206 QVRTIIVNHVNDTWGLKVRQSLWFHLSCLTFGQHTVQEFLVSFGVWIRTPAPYRPPNAPI 180
        ************************************************************

WHcAg   LSTLPEHTVIRRRGGARASRSPRRRTPSPRRRRSQSPRRRRSQSPSANC 188 (SEQ ID NO:1)
VLP-206 LSTLPEHTVIRRRGGARASRSPRRRTPSPRRRRSQSPRRRRSQSPSANC 229 (SEQ ID NO:85)
        *************************************************
```

FIG. 15A

```
WHcAg   MDIDPYKEFGSSYQLLNFLPLDFFPDLNALVDTATALYEEELTGREHCSPHHTAIRQALV  60
VLP-245 MDIDPYKEFGSSYQLLNFLPLDFFPDLNALVDTATALYEEELTGREHCSPHHTAIRQALV  60
        ************************************************************

WHcAg   CWDELTKLIAWMSSNITS------------------EQVRTIIVNHVNDTWGLKVRQSLWF 103
VLP-245 CWDELTKLIAWMSSNITSGILEEDNEKLRKPKHELEQVRTIIVNHVNDTWGLKVRQSLWF 120
        ******************                  ***********************

WHcAg   HLSCLTFGQHTVQEFLVSFGVWIRTPAPYRPPNAPILSTLPEHTVIRRRGGARASRSPRR 163
VLP-245 HLSCLTFGQHTVQEFLVSFGVWIRTPAPYRPPNAPILSTLPEHTVIRRRGGARASRSPRR 180
        ************************************************************

WHcAg   RTPSPRRRRSQSPRRRRSQSPSANC 188 (SEQ ID NO:1)
VLP-245 RTPSPRRRRSQSPRRRRSQSPSANC 205 (SEQ ID NO:86)
        *************************
```

FIG. 15B

SEQUENCE LISTING

<160> NUMBER OF SEQ ID NOS: 94

<210> SEQ ID NO 1
<211> LENGTH: 188
<212> TYPE: PRT
<213> ORGANISM: Woodchuck hepatitis virus

<400> SEQUENCE: 1

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln

```
            100                 105                 110

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
            130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 2
<211> LENGTH: 188
<212> TYPE: PRT
<213> ORGANISM: Artificial Sequence
<220> FEATURE:
<223> OTHER INFORMATION: Synthetic Construct

<400> SEQUENCE: 2

Met Asp Ile Asp Pro Tyr Lys Glu Phe Gly Ser Ser Tyr Gln Leu Leu
1               5                   10                  15

Asn Phe Leu Pro Ala Asp Phe Phe Pro Ala Ala Ala Val Leu Ala Asp
                20                  25                  30

Thr Ala Thr Ala Leu Tyr Glu Glu Leu Thr Gly Arg Glu His Cys
            35                  40                  45

Ser Pro His His Thr Ala Ile Arg Gln Ala Leu Val Cys Trp Asp Glu
50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
            130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 3
<211> LENGTH: 188
<212> TYPE: PRT
<213> ORGANISM: Artificial Sequence
<220> FEATURE:
<223> OTHER INFORMATION: Synthetic Construct

<400> SEQUENCE: 3

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30
```

```
Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Thr Ser Glu Gln
 65                  70                  75                  80

Val Arg Thr Ile Ile Val Asn His Val Asn Asp Thr Trp Gly Leu Lys
                 85                  90                  95

Val Arg Gln Ser Leu Trp Phe His Leu Ser Cys Leu Thr Phe Gly Gln
             100                 105                 110

His Thr Val Gln Glu Phe Leu Val Ser Phe Gly Val Trp Ile Arg Thr
             115                 120                 125

Pro Ala Pro Tyr Arg Pro Pro Pro Pro Ile Leu Ser Thr Leu Pro
130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
             180                 185
```

<210> SEQ ID NO 4
<211> LENGTH: 188
<212> TYPE: PRT
<213> ORGANISM: Artificial Sequence
<220> FEATURE:
<223> OTHER INFORMATION: Synthetic Construct

<400> SEQUENCE: 4

```
Met Asp Ile Asp Pro Tyr Lys Glu Phe Gly Ser Ser Tyr Gln Leu Leu
 1               5                   10                  15

Asn Phe Leu Pro Leu Asp Phe Phe Pro Asp Leu Asn Ala Leu Val Asp
             20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Ser Trp Asp Glu
 50                  55                  60

Leu Thr Lys Leu Ile Ala Trp Met Ser Ser Asn Ile Thr Ser Glu Gln
 65                  70                  75                  80

Val Arg Thr Ile Ile Val Asn His Val Asn Asp Thr Trp Gly Leu Lys
                 85                  90                  95

Val Arg Gln Ser Leu Trp Phe His Leu Ser Cys Leu Thr Phe Gly Gln
             100                 105                 110

His Thr Val Gln Glu Phe Leu Val Ser Phe Gly Val Trp Ile Arg Thr
             115                 120                 125

Pro Ala Pro Tyr Arg Pro Asn Ala Pro Ile Leu Ser Thr Leu Pro
130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
             180                 185
```

<210> SEQ ID NO 5
<211> LENGTH: 188

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 62, 63, 64, 65, 66, 67, 68, 69, 70, 71, 72, 73, 74, 75,
      76, 77, 78, 79, 80, 81, 82, 83, 84, 85, 86, 87
<223> OTHER INFORMATION: Xaa = Any Amino Acid

<400> SEQUENCE: 5

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
            165                 170                 175

Arg Arg Arg Arg Ser Gln Ser Pro Ser Ala Asn Cys
            180                 185

<210> SEQ ID NO 6
<211> LENGTH: 188
<212> TYPE: PRT
<213> ORGANISM: Artificial Sequence
<220> FEATURE:
<223> OTHER INFORMATION: Synthetic Construct

<400> SEQUENCE: 6

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110
```

His Thr Val Gln Glu Phe Leu Val Ser Phe Gly Val Trp Ile Arg Thr
        115                 120                 125
Pro Ala Pro Tyr Arg Pro Pro Asn Ala Pro Ile Leu Ser Thr Leu Pro
        130                 135                 140
Glu His Thr Val Ile Ala Ala Gly Gly Ala Ala Ala Ser Ala Ser
145                 150                 155                 160
Pro Ala Ala Ala Thr Pro Ser Pro Ala Ala Arg Ser Gln Ser Pro
                165                 170                 175
Ala Ala Ala Ala Ser Gln Ser Pro Ser Ala Asn Cys
            180                 185

<210> SEQ ID NO 7
<211> LENGTH: 188
<212> TYPE: PRT
<213> ORGANISM: Artificial Sequence
<220> FEATURE:
<223> OTHER INFORMATION: Synthetic Construct

<400> SEQUENCE: 7

Met Asp Ile Asp Pro Tyr Lys Glu Phe Gly Ser Ser Tyr Gln Leu Leu
1               5                   10                  15
Asn Phe Leu Pro Leu Asp Phe Phe Pro Asp Leu Asn Ala Leu Val Asp
            20                  25                  30
Thr Ala Thr Ala Leu Tyr Glu Glu Leu Thr Gly Arg Glu His Cys
        35                  40                  45
Ser Pro His His Thr Ala Ile Arg Gln Ala Leu Val Cys Trp Asp Glu
    50                  55                  60
Leu Thr Lys Leu Ile Ala Trp Met Ser Ser Ala Ala Ala Ala Ala
65                  70                  75                  80
Ala Ala Ala Ile Ile Val Asn His Val Asn Asp Thr Trp Gly Leu Lys
                85                  90                  95
Val Arg Gln Ser Leu Trp Phe His Leu Ser Cys Leu Thr Phe Gly Gln
            100                 105                 110
His Thr Val Gln Glu Phe Leu Val Ser Phe Gly Val Trp Ile Arg Thr
        115                 120                 125
Pro Ala Pro Tyr Arg Pro Pro Asn Ala Pro Ile Leu Ser Thr Leu Pro
        130                 135                 140
Glu His Thr Val Ile Arg Arg Arg Gly Gly Ala Arg Ala Ser Arg Ser
145                 150                 155                 160
Pro Arg Arg Arg Thr Pro Ser Pro Arg Arg Arg Ser Gln Ser Pro
                165                 170                 175
Arg Arg Arg Arg Ser Gln Ser Pro Ser Ala Asn Cys
            180                 185

<210> SEQ ID NO 8
<211> LENGTH: 187
<212> TYPE: PRT
<213> ORGANISM: Ground squirrel hepatitis virus

<400> SEQUENCE: 8

Met Asp Ile Asp Pro Tyr Lys Glu Phe Gly Ser Ser Tyr Gln Leu Leu
1               5                   10                  15
Asn Phe Leu Pro Leu Asp Phe Phe Pro Asp Leu Asn Ala Leu Val Asp
            20                  25                  30
Thr Ala Ala Ala Leu Tyr Glu Glu Leu Thr Gly Arg Glu His Cys
        35                  40                  45
Ser Pro His His Thr Ala Ile Arg Gln Ala Leu Val Cys Trp Glu Glu

```
                 50                  55                  60

Leu Thr Arg Leu Ile Thr Trp Met Ser Glu Asn Thr Thr Glu Val
 65                  70                  75                  80

Arg Arg Ile Ile Val Asp His Val Asn Asp Thr Trp Gly Leu Lys Val
                 85                  90                  95

Arg Gln Thr Leu Trp Phe His Leu Ser Cys Leu Thr Phe Gly Gln His
                100                 105                 110

Thr Val Gln Glu Phe Leu Val Ser Phe Gly Val Trp Ile Arg Thr Pro
                115                 120                 125

Ala Pro Tyr Arg Pro Pro Asn Ala Pro Ile Leu Ser Thr Leu Pro Glu
                130                 135                 140

His Thr Val Ile Arg Arg Gly Gly Ser Arg Ala Ala Arg Ser Pro
145                 150                 155                 160

Arg Arg Arg Thr Pro Ser Pro Arg Arg Arg Ser Gln Ser Pro Arg
                165                 170                 175

Arg Arg Arg Ser Gln Ser Pro Ala Ser Asn Cys
                180                 185

<210> SEQ ID NO 9
<211> LENGTH: 187
<212> TYPE: PRT
<213> ORGANISM: Arctic ground squirrel hepatitis virus

<400> SEQUENCE: 9

Met Asp Ile Asp Pro Tyr Lys Glu Phe Gly Ser Ser Tyr Gln Leu Leu
 1               5                  10                  15

Asn Phe Leu Pro Leu Asp Phe Phe Pro Glu Leu Asn Ala Leu Val Asp
                20                  25                  30

Thr Ala Thr Ala Leu Tyr Glu Glu Glu Leu Thr Gly Arg Glu His Cys
                35                  40                  45

Ser Pro His His Thr Ala Ile Arg Gln Ala Leu Val Cys Trp Glu Glu
                50                  55                  60

Leu Thr Arg Leu Ile Ala Trp Met Ser Ala Asn Ile Asn Ser Glu Glu
 65                  70                  75                  80

Val Arg Arg Val Ile Val Ala His Val Asn Asp Thr Trp Gly Leu Lys
                85                  90                  95

Val Arg Gln Asn Leu Trp Phe His Leu Ser Cys Leu Thr Phe Gly Gln
                100                 105                 110

His Thr Val Gln Glu Phe Leu Val Ser Phe Gly Val Arg Ile Arg Thr
                115                 120                 125

Pro Ala Pro Tyr Arg Pro Pro Asn Ala Pro Ile Leu Ser Thr Leu Pro
                130                 135                 140

Glu His Thr Val Ile Arg Arg Arg Gly Ser Ala Arg Val Val Arg Ser
145                 150                 155                 160

Pro Arg Arg Arg Thr Pro Ser Pro Arg Arg Arg Ser Gln Ser Pro
                165                 170                 175

Arg Arg Arg Arg Gln Ser Pro Ala Ser Asn Cys
                180                 185

<210> SEQ ID NO 10
<211> LENGTH: 183
<212> TYPE: PRT
<213> ORGANISM: Human hepatitis B virus

<400> SEQUENCE: 10

Met Asp Ile Asp Pro Tyr Lys Glu Phe Gly Ala Thr Val Glu Leu Leu
```

```
                1               5                   10                  15
            Ser Phe Leu Pro Ser Asp Phe Pro Ser Val Arg Asp Leu Leu Asp
                            20                  25                  30

Thr Ala Ser Ala Leu Tyr Arg Glu Ala Leu Glu Ser Pro Glu His Cys
                            35                  40                  45

Ser Pro His His Thr Ala Leu Arg Gln Ala Ile Leu Cys Trp Gly Glu
                50                      55                  60

Leu Met Thr Leu Ala Thr Trp Val Gly Val Asn Leu Glu Asp Pro Ala
            65                      70                  75                  80

Ser Arg Asp Leu Val Val Ser Tyr Val Asn Thr Asn Met Gly Leu Lys
                            85                  90                  95

Phe Arg Gln Leu Leu Trp Phe His Ile Ser Cys Leu Thr Phe Gly Arg
                            100                 105                 110

Glu Thr Val Ile Glu Tyr Leu Val Ser Phe Gly Val Trp Ile Arg Thr
                            115                 120                 125

Pro Pro Ala Tyr Arg Pro Pro Asn Ala Pro Ile Leu Ser Thr Leu Pro
                    130                 135                 140

Glu Thr Thr Val Val Arg Arg Gly Arg Ser Pro Arg Arg Arg Thr
            145                 150                 155                 160

Pro Ser Pro Arg Arg Arg Ser Gln Ser Pro Arg Arg Arg Ser
                            165                 170                 175

Gln Ser Arg Glu Ser Gln Cys
                            180
```

<210> SEQ ID NO 11
<211> LENGTH: 149
<212> TYPE: PRT
<213> ORGANISM: Artificial Sequence
<220> FEATURE:
<223> OTHER INFORMATION: Synthetic Construct

<400> SEQUENCE: 11

```
            Met Asp Ile Asp Pro Tyr Lys Glu Phe Gly Ser Ser Tyr Gln Leu Leu
            1               5                   10                  15

Asn Phe Leu Pro Leu Asp Phe Phe Pro Asp Leu Asn Ala Leu Val Asp
                            20                  25                  30

Thr Ala Thr Ala Leu Tyr Glu Glu Leu Thr Gly Arg Glu His Cys
                            35                  40                  45

Ser Pro His His Thr Ala Ile Arg Gln Ala Leu Val Cys Trp Asp Glu
                50                      55                  60

Leu Thr Lys Leu Ile Ala Trp Met Ser Ser Asn Ile Thr Ser Glu Gln
            65                      70                  75                  80

Val Arg Thr Ile Ile Val Asn His Val Asn Asp Thr Trp Gly Leu Lys
                            85                  90                  95

Val Arg Gln Ser Leu Trp Phe His Leu Ser Cys Leu Thr Phe Gly Gln
                            100                 105                 110

His Thr Val Gln Glu Phe Leu Val Ser Phe Gly Val Trp Ile Arg Thr
                            115                 120                 125

Pro Ala Pro Tyr Arg Pro Pro Asn Ala Pro Ile Leu Ser Thr Leu Pro
                    130                 135                 140

Glu His Thr Val Ile
            145
```

<210> SEQ ID NO 12
<211> LENGTH: 188
<212> TYPE: PRT

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 21, 26, 27, 28, 29, 31, 61, 62, 63, 64, 65, 66, 67, 68,
      69, 70, 71, 72, 73, 74, 75, 76, 77, 78, 79, 80, 81, 82, 83,
      84, 85, 86, 87, 136, 137, 150, 151, 152, 153, 154, 155,
      156, 157, 158, 159, 160, 161, 162, 163, 164, 165, 166, 167
<223> OTHER INFORMATION: Xaa = Any Amino Acid and can be present or
      absent
<220> FEATURE:
<221> NAME/KEY: VARIANT
<222> LOCATION: 168, 169, 170, 171, 172, 173, 174, 175, 176, 177, 178,
      179, 180, 181, 182, 183, 184, 185, 186, 187, 188
<223> OTHER INFORMATION: Xaa = Any Amino Acid and can be present or
      absent

<400> SEQUENCE: 12

Met Asp Ile Asp Pro Tyr Lys Glu Phe Gly Ser Ser Tyr Gln Leu Leu
1               5                   10                  15

Asn Phe Leu Pro Xaa Asp Phe Phe Pro Xaa Xaa Xaa Xaa Leu Xaa Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa His Val Asn Asp Thr Trp Gly Leu Lys
                85                  90                  95

Val Arg Gln Ser Leu Trp Phe His Leu Ser Cys Leu Thr Phe Gly Gln
                100                 105                 110

His Thr Val Gln Glu Phe Leu Val Ser Phe Gly Val Trp Ile Arg Thr
            115                 120                 125

Pro Ala Pro Tyr Arg Pro Pro Xaa Xaa Pro Ile Leu Ser Thr Leu Pro
        130                 135                 140

Glu His Thr Val Ile Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa
            180                 185

<210> SEQ ID NO 13
<211> LENGTH: 188
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 21, 26, 27, 28, 29, 31, 61, 62, 63, 64, 65, 66, 67, 68,
      69, 70, 71, 72, 73, 74, 75, 76, 77, 78, 79, 80, 81, 82, 83,
      84, 85, 86, 87, 136, 137, 150, 151, 152, 156, 159, 162,
      163, 164, 169, 170, 171, 177, 178, 179, 180
<223> OTHER INFORMATION: Xaa = Any Amino Acid and can be present or
      absent

<400> SEQUENCE: 13

Met Asp Ile Asp Pro Tyr Lys Glu Phe Gly Ser Ser Tyr Gln Leu Leu
1               5                   10                  15

Asn Phe Leu Pro Xaa Asp Phe Phe Pro Xaa Xaa Xaa Xaa Leu Xaa Asp
            20                  25                  30
```

Thr Ala Thr Ala Leu Tyr Glu Glu Leu Thr Gly Arg Glu His Cys
            35                  40                  45

Ser Pro His His Thr Ala Ile Arg Gln Ala Leu Val Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Xaa Xaa Pro Ile Leu Ser Thr Leu Pro
    130                 135                 140

Glu His Thr Val Ile Xaa Xaa Xaa Gly Gly Ala Xaa Ala Ser Xaa Ser
145                 150                 155                 160

Pro Xaa Xaa Xaa Thr Pro Ser Pro Xaa Xaa Xaa Arg Ser Gln Ser Pro
            165                 170                 175

Xaa Xaa Xaa Xaa Ser Gln Ser Pro Ser Ala Asn Cys
            180                 185

<210> SEQ ID NO 14
<211> LENGTH: 188
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 21, 26, 27, 28, 29, 31, 61, 62, 63, 64, 65, 66, 67, 68,
      69, 70, 71, 72, 73, 74, 75, 76, 77, 78, 79, 80, 81, 82, 83,
      84, 85, 86, 87, 136, 137, 150, 151, 152, 156, 159, 162,
      163, 164, 169, 170, 171, 177, 178, 179, 180, 188
<223> OTHER INFORMATION: Xaa = Any Amino Acid and can be present or
      absent

<400> SEQUENCE: 14

Met Asp Ile Asp Pro Tyr Lys Glu Phe Gly Ser Ser Tyr Gln Leu Leu
1               5                   10                  15

Asn Phe Leu Pro Xaa Asp Phe Phe Pro Xaa Xaa Xaa Xaa Leu Xaa Asp
            20                  25                  30

Thr Ala Thr Ala Leu Tyr Glu Glu Leu Thr Gly Arg Glu His Cys
            35                  40                  45

Ser Pro His His Thr Ala Ile Arg Gln Ala Leu Val Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Xaa Xaa Pro Ile Leu Ser Thr Leu Pro
    130                 135                 140

Glu His Thr Val Ile Xaa Xaa Xaa Gly Gly Ala Xaa Ala Ser Xaa Ser
145                 150                 155                 160

Pro Xaa Xaa Xaa Thr Pro Ser Pro Xaa Xaa Xaa Arg Ser Gln Ser Pro
            165                 170                 175

Xaa Xaa Xaa Xaa Ser Gln Ser Pro Ser Ala Asn Xaa
            180                 185

<210> SEQ ID NO 15
<211> LENGTH: 567
<212> TYPE: DNA
<213> ORGANISM: Woodchuck hepatitis virus

<400> SEQUENCE: 15
atggacatag atccctataa agaatttggt tcatcttatc agttgttgaa ttttcttcct     60
ttggacttct ttcctgacct taatgctttg gtggacactg ctactgcctt gtatgaagaa    120
gagctaacag gtagggaaca ttgctctccg caccatacag ctattagaca agctttagta    180
tgctgggatg aattaactaa attgatagct tggatgagct caacataac ttctgaacaa     240 gtaagaacaa tcatagtaaa tcatgtcaat gatacctggg gacttaaggt gagacaaagt    300
ttatggtttc atttgtcatg tctcactttt ggacaacata cagttcaaga attttagta    360 agttttggag tatggatcag aactccagct ccatatagac ctcctaatgc acccattctc    420
tcgactcttc cggaacatac agtcattagg agaagaggag gtgcaagagc ttctaggtcc    480
cccagaagac gcactccctc tcctcgcagg agaagatctc aatcaccgcg tcgcagacgc    540
tctcaatctc catctgccaa ctgctga                                         567

<210> SEQ ID NO 16
<211> LENGTH: 3323
<212> TYPE: DNA
<213> ORGANISM: Woodchuck hepatitis virus

<400> SEQUENCE: 16
aattcgggac ataccacgtg gtttagttcc gcctcaaact ccaacaaatc gagatcaagg     60
gagaaagcct actcctccaa ctccacctct aagagatact cacccccact taactatgaa    120
aaatcagact tttcatctcc aggggttcgt agacggatta cgagacttga caacaacgga    180
acgccaacac aatgcctatg agatcctttt tacaacacta gcccctgcgg ttcctactgt    240
atccaccata ttgtctcctc cctcgacgac tggggaccct gcactgtcac cggagatgtc    300
accatcaagt ctcctaggac tcctcgcagg attacaggtg gtgtatttct gtggacaaa    360 aatcctaaca atagctcaga atctagattg gtggtggact ctctcagtt tccaggggg     420 cataccagag tgcactggcc aaaattcgca gttccaaact tgcaaacact tgccaacctc    480
ctgtccacca acttgcaatg gctttcgttg gatgtatctg cggcgtttta tcatatacct    540
attagtcctg ctgctgtgcc tcatcttctt gttggttctc ctggactgga aggtttaat    600 acctgtctgt cctcttcaac ccacaacaga acaacagtc aattgcagac aatgcacaat    660
ctctgcacaa gacatgtata tcctccctta ctgttgttgt ttaaaaccta cggcaggaaa    720
ttgcacttgt tggcccatcc cttcatcatg gctttagga aattacctat gggagtgggc    780
cttagcccgt ttctcttggc tcaatttact agtgcccttg cttcaatggt taggaggaat    840
ttccctcatt gcgtggtttt tgcttatatg gatgatttgg ttttgggggc ccgcacttct    900
gagcatctta ccgccatttta ttcccatatt tgttctgttt ttcttgattt gggtatacat    960
ttgaatgtca ataaaacaaa atggtggggc aatcatctac atttcatggg atatgtgatt   1020
actagttcag gtgtattgcc acaagacaaa catgttaaga aaatttcccg ttatttgcgc    1080
tctgttcctg ttaatcaacc tctggattac aaaatttgtg aaagattgac tggtattctt   1140

```
aactatgttg ctccttttac gctatgtgga tacgctgctt taatgccttt gtatcatgct   1200
attacttccc gtacggcttt cattttctcc tccttgtata aatcctggtt gctgtctctt   1260
tatgaggagt tgtggcccgt tgtcaggcaa cgtggcgtgg tgtgcactgt gtttgctgac   1320
gcaaccccca ctggttgggg cattgccacc acctatcaac tcctttccgg gactttcgct   1380 ttcccctcc ctattgccac ggcggaactc attgccgcct gccttgcccg ctgctggaca    1440
ggggctcggc tgttgggcac tgacaattcc gtggtgttgt cggggaagct gacgtccttt   1500
ccatggctgc tcgcctgtgt tgccaactgg attctgcgcg gacgtccttt ctgctacgtc   1560
ccttcggccc tcaatccagc ggaccttcct tcccgcggcc tgctgccggt tctgcggcct   1620
cttccgcgtc ttcgccttcg ccctcagacg agtcggatct cccttgggc cgcctccccg    1680 cctgtttcgc ctcggcgtcc ggtccgtgtt gcttggtctt cacctgtgca gaattgcgaa   1740
ccatggattc caccgtgaac tttgtctcct ggcatgcaaa tcgtcaactt ggcatgccaa   1800
gtaaggacct ttggactcct tatataaaag atcaattatt aactaaatgg gaggagggca   1860
gcattgatcc tagattatca atatttgtat taggaggctg taggcataaa tgcatgcgac   1920
ttctgtaacc atgtatcttt ttcacctgtg ccttgttttt gcctgtgttc catgtcctac   1980
ttttcaagcc tccaagctgt gccttggatg gctttgggc atggacatag atccctataa    2040
agaatttggt tcatcttatc agttgttgaa ttttcttcct ttggacttct ttcctgacct   2100
taatgctttg gtggacactg ctactgcctt gtatgaagaa gagctaacag gtagggaaca   2160
ttgctctccg caccatacag ctattagaca agctttagta tgctgggatg aattaactaa   2220
attgatagct tggatgagct ctaacataac ttctgaacaa gtaagaacaa tcatagtaaa   2280
tcatgtcaat gatacctggg gacttaaggt gagacaaagt ttatggtttc atttgtcatg   2340
tctcactttt ggacaacata cagttcaaga atttttagta agttttggag tatggatcag   2400
aactccagct ccatatagac ctcctaatgc acccattctc tcgactcttc cggaacatac   2460
agtcattagg agaagaggag gtgcaagagc ttctaggtcc cccagaagac gcactccctc   2520
tcctcgcagg agaagatctc aatcaccgcg tcgcagacgc tctcaatctc catctgccaa   2580
ctgctgatct tcaatgggta cataaaacta atgctattac aggtctttac tctaaccaag   2640
ctgctcagtt caatccgcat tggattcaac ctgagtttcc tgaacttcat ttacataatg   2700
atttaattca aaaattgcaa cagtattttg gtccttgac tataaatgaa aagagaaaat     2760
tgcaattaaa ttttcctgcc agattttcc ccaaagctac taaatatttc cctttaatta    2820
aaggcataaa aaacaattat cctaattttg ctttagaaca tttctttgct accgcaaatt   2880
atttgtggac tttatgggaa gctggaattt tgtatttaag gaagaatcaa acaactttga   2940
cttttaaagg taaccatat tcttgggaac acagacagct agtgcaacat aatgggcaac     3000
aacataaaag tcaccttcaa tccagacaaa atagcagcat ggtggcctgc agtgggcact   3060
tattacacaa ccacttatcc tcagaatcag tcagtgtttc aaccaggaat ttatcaaaca   3120
acatctctga taaatcccaa aaatcaacaa gaactggact ctgttcttat aaacagatac   3180
aaacagatag actggaacac ttggcaagga tttcctgtgg atcaaaaatt accattggtc   3240
agcagggatc ctcccccaaa acctatata aatcaatcag ctcaaacttt cgaaatcaaa    3300
cctgggccta aatagttcc cgg                                            3323
```

<210> SEQ ID NO 17
<211> LENGTH: 64
<212> TYPE: PRT

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 5, 6, 7, 8, 9, 10, 11, 12, 13, 14, 15, 16, 17, 18,
      19, 20, 21, 22, 23, 24, 25, 26, 27, 28, 29, 30, 31, 32, 33, 34,
      35, 36, 37, 38, 39, 40, 41, 42, 43, 44, 45, 46, 47, 48, 49,
      50, 51, 52, 53, 54, 55, 56, 57, 58, 59, 60, 61, 62, 63
<223> OTHER INFORMATION: Xaa = Any Amino Acid and up to 60 can be
      present or absent

<400> SEQUENCE: 17

Gly Ile Leu Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Leu
    50                  55                  60

<210> SEQ ID NO 18
<211> LENGTH: 64
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 30, 31,
      32, 33, 34, 35, 36, 37, 38, 39, 40, 41, 42, 43, 44, 45,
      46, 47, 48, 49, 50, 51, 52, 53, 54, 55, 56, 57, 58, 59,
      60
<223> OTHER INFORMATION: Xaa = Any Amino Acid and up to 60 can be
      present or absent

<400> SEQUENCE: 18

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Trp Leu Trp Gly
    50                  55                  60

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct

<400> SEQUENCE: 19

Asn Ala Asn Pro Asn Val Asp Pro Asn Ala Asn Pro Asn Ala Asn Pro
1               5                   10                  15

Asn Ala Asn Pro
            20

<210> SEQ ID NO 20
<211> LENGTH: 274
<212> TYPE: PRT
<213> ORGANISM: Artificial Sequence
<220> FEATURE:
```

<223> OTHER INFORMATION: Synthetic Construct

<400> SEQUENCE: 20

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Ser Trp Asp Glu
    50                  55                  60

Leu Thr Lys Leu Ile Ala Trp Met Ser Ser Asn Ile Thr Ser Gly Ile
65                  70                  75                  80

Leu Asn Ala Asn Pro Asn Val Asp Pro Asn Ala Asn Pro Asn Ala Asn
                85                  90                  95

Pro Asn Ala Asn Pro Leu Glu Gln Val Arg Thr Ile Ile Val Asn His
            100                 105                 110

Val Asn Asp Thr Trp Gly Leu Lys Val Arg Gln Ser Leu Trp Phe His
        115                 120                 125

Leu Ser Cys Leu Thr Phe Gly Gln His Thr Val Gln Glu Phe Leu Val
    130                 135                 140

Ser Phe Gly Val Trp Ile Arg Thr Pro Ala Pro Tyr Arg Pro Pro Asn
145                 150                 155                 160

Ala Pro Ile Leu Ser Thr Leu Pro Glu His Thr Val Ile Arg Arg Arg
                165                 170                 175

Gly Gly Ala Arg Ala Ser Arg Ser Pro Arg Arg Gly Thr Pro Ser Pro
            180                 185                 190

Arg Arg Arg Arg Ser Gln Ser Pro Arg Arg Arg Ser Gln Ser Pro
            195                 200                 205

Ser Ala Asn Cys Asp Ile Glu Tyr Leu Asn Lys Ile Gln Asn Ser Leu
    210                 215                 220

Ser Thr Glu Trp Ser Pro Cys Ser Val Thr Ser Gly Asn Gly Ile Gln
225                 230                 235                 240

Val Arg Ile Lys Pro Gly Ser Ala Asn Lys Pro Lys Asp Glu Leu Asp
                245                 250                 255

Tyr Glu Asn Asp Ile Glu Lys Lys Ile Cys Lys Met Glu Lys Cys Ser
            260                 265                 270

Ser Val
```

<210> SEQ ID NO 21
<211> LENGTH: 342
<212> TYPE: PRT
<213> ORGANISM: Artificial Sequence
<220> FEATURE:
<223> OTHER INFORMATION: Synthetic Construct

<400> SEQUENCE: 21

```
Met Lys Lys Cys Thr Ile Leu Val Val Ala Ser Leu Leu Leu Val Asn
1               5                   10                  15

Ser Leu Leu Pro Gly Tyr Gly Gln Asn Lys Ser Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Asn Arg Asn Thr Val
    50                  55                  60
```

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Gln Pro Pro Pro Pro
                85                  90                  95

Pro Asn Pro Asn Asp Pro Pro Pro Asn Pro Asn Asp Pro Pro Pro
            100                 105                 110

Pro Asn Pro Asn Asp Pro Pro Pro Asn Pro Asn Asp Pro Pro Pro
            115                 120                 125

Pro Asn Ala Asn Asp Pro Pro Pro Asn Ala Asn Asp Pro Ala Pro
            130                 135                 140

Pro Asn Ala Asn Asp Pro Ala Pro Pro Asn Ala Asn Asp Pro Ala Pro
145                 150                 155                 160

Pro Asn Ala Asn Asp Pro Ala Pro Pro Asn Ala Asn Asp Pro Pro Pro
            165                 170                 175

Pro Asn Pro Asn Asp Pro Ala Pro Pro Asn Ala Asn Asp Pro Pro Pro
            180                 185                 190

Pro Asn Pro Asn Asp Pro Ala Pro Pro Gln Gly Asn Asn Asn Pro Gln
            195                 200                 205

Pro Gln Pro Arg Pro Gln Pro Gln Pro Gln Pro Gln Pro Gln Pro Gln
            210                 215                 220

Pro Gln Pro Gln Pro Gln Pro Arg Pro Gln Pro Gln Pro Gln Pro Gly
225                 230                 235                 240

Gly Asn Asn Asn Lys Asn Asn Asn Asp Asp Ser Tyr Ile Pro
                245                 250                 255

Ser Ala Glu Lys Ile Leu Glu Tyr Leu Asn Lys Ile Gln Asn Ser Leu
            260                 265                 270

Ser Thr Glu Trp Ser Pro Cys Ser Val Thr Cys Gly Asn Gly Ile Gln
            275                 280                 285

Val Arg Ile Lys Pro Gly Ser Ala Asn Lys Pro Lys Asp Glu Leu Asp
            290                 295                 300

Tyr Glu Asn Asp Ile Glu Lys Lys Ile Cys Lys Met Glu Lys Cys Ser
305                 310                 315                 320

Ser Val Phe Asn Val Val Asn Ser Ser Ile Gly Leu Ile Met Val Leu
            325                 330                 335

Ser Phe Leu Phe Leu Asn
            340

<210> SEQ ID NO 22
<211> LENGTH: 60
<212> TYPE: PRT
<213> ORGANISM: Plasmodium berghei

<400> SEQUENCE: 22

Glu Phe Val Lys Gln Ile Arg Asp Ser Ile Thr Glu Glu Trp Ser Gln
1               5                   10                  15

Cys Asn Val Thr Cys Gly Ser Gly Ile Arg Val Arg Lys Arg Lys Gly
            20                  25                  30

Ser Asn Lys Lys Ala Glu Asp Leu Thr Leu Glu Asp Ile Asp Thr Glu
        35                  40                  45

Ile Cys Lys Met Asp Lys Cys Ser Ser Ile Phe Asn
    50                  55                  60

<210> SEQ ID NO 23
<211> LENGTH: 60
<212> TYPE: PRT
<213> ORGANISM: Plasmodium falciparum

```
<400> SEQUENCE: 23

Glu Tyr Leu Asn Lys Ile Gln Asn Ser Leu Ser Thr Glu Trp Ser Pro
1               5                   10                  15

Cys Ser Val Thr Ser Gly Asn Gly Ile Gln Val Arg Ile Lys Pro Gly
            20                  25                  30

Ser Ala Asn Lys Pro Lys Asp Glu Leu Asp Tyr Glu Asn Asp Ile Glu
        35                  40                  45

Lys Lys Ile Cys Lys Met Glu Lys Cys Ser Ser Val
    50                  55                  60

<210> SEQ ID NO 24
<211> LENGTH: 24
<212> TYPE: PRT
<213> ORGANISM: Artificial Sequence
<220> FEATURE:
<223> OTHER INFORMATION: Synthetic Construct

<400> SEQUENCE: 24

Gly Ile Leu Asn Ala Asn Pro Asn Val Asp Pro Asn Ala Asn Pro Asn
1               5                   10                  15

Ala Asn Pro Asn Ala Asn Pro Leu
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic Construct

<400> SEQUENCE: 25

Gly Ile Leu Asp Pro Asn Ala Asn Pro Asn Val Asp Pro Asn Ala Asn
1               5                   10                  15

Pro Asn Val Leu
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic Construct

<400> SEQUENCE: 26

Gly Ile Leu Asn Pro Asn Val Asp Pro Asn Ala Asn Pro Asn Val Asp
1               5                   10                  15

Pro Asn Ala Leu
            20

<210> SEQ ID NO 27
<211> LENGTH: 16
<212> TYPE: PRT
<213> ORGANISM: Artificial Sequence
<220> FEATURE:
<223> OTHER INFORMATION: Synthetic Construct

<400> SEQUENCE: 27

Gly Ile Leu Asn Val Asp Pro Asn Ala Asn Pro Asn Val Asp Pro Leu
1               5                   10                  15

<210> SEQ ID NO 28
<211> LENGTH: 20
```

-continued

```
<212> TYPE: PRT
<213> ORGANISM: Artificial Sequence
<220> FEATURE:
<223> OTHER INFORMATION: Synthetic Construct

<400> SEQUENCE: 28

Gly Ile Leu Asn Ala Asn Pro Asn Val Asp Pro Asn Ala Asn Pro Asn
1               5                   10                  15

Val Asp Pro Leu
            20

<210> SEQ ID NO 29
<211> LENGTH: 22
<212> TYPE: PRT
<213> ORGANISM: Artificial Sequence
<220> FEATURE:
<223> OTHER INFORMATION: Synthetic Construct

<400> SEQUENCE: 29

Gly Ile Leu Glu Asn Ala Asn Pro Asn Ala Asn Pro Asn Ala Asn Pro
1               5                   10                  15

Asn Ala Asn Pro Glu Leu
            20

<210> SEQ ID NO 30
<211> LENGTH: 31
<212> TYPE: PRT
<213> ORGANISM: Artificial Sequence
<220> FEATURE:
<223> OTHER INFORMATION: Synthetic Construct

<400> SEQUENCE: 30

Gly Ile Leu Glu Glu Asp Glu Asp Lys Arg Asp Gly Asn Asn Glu Asp
1               5                   10                  15

Asn Glu Lys Leu Arg Lys Pro Lys His Lys Lys Leu Glu Glu Leu
            20                  25                  30

<210> SEQ ID NO 31
<211> LENGTH: 18
<212> TYPE: PRT
<213> ORGANISM: Artificial Sequence
<220> FEATURE:
<223> OTHER INFORMATION: Synthetic Construct

<400> SEQUENCE: 31

Gly Ile Leu Glu Lys Leu Lys Gln Pro Gly Asp Gly Asn Pro Asp Pro
1               5                   10                  15

Glu Leu

<210> SEQ ID NO 32
<211> LENGTH: 22
<212> TYPE: PRT
<213> ORGANISM: Artificial Sequence
<220> FEATURE:
<223> OTHER INFORMATION: Synthetic Construct

<400> SEQUENCE: 32

Gly Ile Leu His Asn Met Pro Asn Asp Pro Asn Arg Asn Val Asp Glu
1               5                   10                  15

Asn Ala Asn Ala Asn Leu
            20

<210> SEQ ID NO 33
<211> LENGTH: 17
```

```
<212> TYPE: PRT
<213> ORGANISM: Artificial Sequence
<220> FEATURE:
<223> OTHER INFORMATION: Synthetic Construct

<400> SEQUENCE: 33

Gly Ile Leu Glu Glu Asp Asn Glu Lys Leu Arg Lys Pro Lys His Glu
1               5                   10                  15

Leu

<210> SEQ ID NO 34
<211> LENGTH: 21
<212> TYPE: PRT
<213> ORGANISM: Artificial Sequence
<220> FEATURE:
<223> OTHER INFORMATION: Synthetic Construct

<400> SEQUENCE: 34

Gly Ile Leu Glu Asp Gly Asn Asn Glu Asp Asn Glu Lys Leu Arg Lys
1               5                   10                  15

Pro Lys His Glu Leu
            20

<210> SEQ ID NO 35
<211> LENGTH: 24
<212> TYPE: PRT
<213> ORGANISM: Artificial Sequence
<220> FEATURE:
<223> OTHER INFORMATION: Synthetic Construct

<400> SEQUENCE: 35

Gly Ile Leu Glu Glu Glu Glu Asp Asn Glu Lys Leu Arg Lys Pro Lys
1               5                   10                  15

His Lys Lys Leu Glu Glu Glu Leu
            20

<210> SEQ ID NO 36
<211> LENGTH: 27
<212> TYPE: PRT
<213> ORGANISM: Artificial Sequence
<220> FEATURE:
<223> OTHER INFORMATION: Synthetic Construct

<400> SEQUENCE: 36

Gly Ile Leu Glu Glu Glu Glu Asp Asn Glu Lys Leu Arg Lys Pro Lys
1               5                   10                  15

His Lys Lys Leu Lys Gln Pro Glu Glu Glu Leu
            20                  25

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct

<400> SEQUENCE: 37

Gly Ile Leu Glu Glu Asn Ala Ile Lys Lys Thr Lys Asn Gln Glu Glu
1               5                   10                  15

Leu

<210> SEQ ID NO 38
<211> LENGTH: 16
<212> TYPE: PRT
```

```
<213> ORGANISM: Artificial Sequence
<220> FEATURE:
<223> OTHER INFORMATION: Synthetic Construct

<400> SEQUENCE: 38

Gly Ile Leu Glu Glu Ser Ala Ile Lys Lys Pro Val Thr Glu Glu Leu
1               5                   10                  15

<210> SEQ ID NO 39
<211> LENGTH: 22
<212> TYPE: PRT
<213> ORGANISM: Artificial Sequence
<220> FEATURE:
<223> OTHER INFORMATION: Synthetic Construct

<400> SEQUENCE: 39

Gly Ile Leu Glu Tyr Gly Lys Ala Ile Ala Val Asp Ala Phe Ile Lys
1               5                   10                  15

Lys Ile Asn Glu Glu Leu
            20

<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Gly Ile Leu Asp Thr Asn Gly Ile Arg Tyr Ala Tyr Asp Leu
1               5                   10

<210> SEQ ID NO 41
<211> LENGTH: 20
<212> TYPE: PRT
<213> ORGANISM: Plasmodium falciparum

<400> SEQUENCE: 41

Glu Tyr Leu Asn Lys Ile Gln Asn Ser Leu Ser Thr Glu Trp Ser Pro
1               5                   10                  15

Cys Ser Val Thr
            20

<210> SEQ ID NO 42
<211> LENGTH: 24
<212> TYPE: PRT
<213> ORGANISM: Plasmodium falciparum

<400> SEQUENCE: 42

Gly Asn Gly Ile Gln Val Arg Ile Lys Pro Gly Ser Ala Asn Lys Pro
1               5                   10                  15

Lys Asp Glu Leu Asp Tyr Glu Asn
            20

<210> SEQ ID NO 43
<211> LENGTH: 15
<212> TYPE: PRT
<213> ORGANISM: Plasmodium falciparum

<400> SEQUENCE: 43

Asp Ile Glu Lys Lys Ile Cys Lys Met Glu Lys Cys Ser Ser Val
1               5                   10                  15

<210> SEQ ID NO 44
```

```
<211> LENGTH: 20
<212> TYPE: PRT
<213> ORGANISM: Plasmodium berghei

<400> SEQUENCE: 44

Glu Phe Val Lys Gln Ile Arg Asp Ser Ile Thr Glu Glu Trp Ser Gln
1               5                   10                  15

Cys Asn Val Thr
            20

<210> SEQ ID NO 45
<211> LENGTH: 24
<212> TYPE: PRT
<213> ORGANISM: Plasmodium berghei

<400> SEQUENCE: 45

Gly Ser Gly Ile Arg Val Arg Lys Arg Lys Gly Ser Asn Lys Lys Ala
1               5                   10                  15

Glu Asp Leu Thr Leu Glu Asp Ile
            20

<210> SEQ ID NO 46
<211> LENGTH: 15
<212> TYPE: PRT
<213> ORGANISM: Plasmodium berghei

<400> SEQUENCE: 46

Asp Thr Glu Ile Cys Lys Met Asp Lys Cys Ser Ser Ile Phe Asn
1               5                   10                  15

<210> SEQ ID NO 47
<211> LENGTH: 60
<212> TYPE: PRT
<213> ORGANISM: Plasmodium falciparum

<400> SEQUENCE: 47

Gln Tyr Leu Lys Lys Ile Lys Asn Ser Ile Ser Thr Glu Trp Ser Pro
1               5                   10                  15

Cys Ser Val Thr Cys Gly Asn Gly Ile Gln Val Arg Ile Lys Pro Gly
            20                  25                  30

Ser Ala Asn Lys Pro Lys Asp Glu Leu Asp Tyr Glu Asn Asp Ile Glu
        35                  40                  45

Lys Lys Ile Cys Lys Met Glu Lys Cys Ser Ser Val
    50                  55                  60

<210> SEQ ID NO 48
<211> LENGTH: 60
<212> TYPE: PRT
<213> ORGANISM: Plasmodium falciparum

<400> SEQUENCE: 48

Glu Tyr Leu Asn Lys Ile Gln Asn Ser Leu Ser Thr Glu Trp Ser Pro
1               5                   10                  15

Cys Ser Val Thr Cys Gly Asn Gly Ile Gln Val Arg Ile Lys Pro Gly
            20                  25                  30

Ser Ala Asn Lys Pro Lys Asp Glu Leu Asp Tyr Ala Asn Asp Ile Glu
        35                  40                  45

Lys Lys Ile Cys Lys Met Glu Lys Cys Ser Ser Val
    50                  55                  60

<210> SEQ ID NO 49
```

```
<211> LENGTH: 60
<212> TYPE: PRT
<213> ORGANISM: Plasmodium falciparum

<400> SEQUENCE: 49

Glu Tyr Leu Asn Lys Ile Gln Asn Ser Leu Ser Thr Glu Trp Ser Pro
1               5                   10                  15

Cys Ser Val Thr Ser Gly Asn Gly Ile Gln Val Arg Ile Lys Pro Gly
            20                  25                  30

Ser Ala Asn Lys Pro Lys Asp Glu Leu Asp Tyr Glu Asn Asp Ile Glu
        35                  40                  45

Lys Lys Ile Cys Lys Met Glu Lys Cys Ser Ser Val
    50                  55                  60

<210> SEQ ID NO 50
<211> LENGTH: 60
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gln or Glu
<220> FEATURE:
<221> NAME/KEY: VARIANT
<222> LOCATION: 4
<223> OTHER INFORMATION: Xaa = Lys or Asn
<220> FEATURE:
<221> NAME/KEY: VARIANT
<222> LOCATION: 7
<223> OTHER INFORMATION: Xaa = Lys or Gln
<220> FEATURE:
<221> NAME/KEY: VARIANT
<222> LOCATION: 10
<223> OTHER INFORMATION: Xaa = Ile or Leu
<220> FEATURE:
<221> NAME/KEY: VARIANT
<222> LOCATION: 21
<223> OTHER INFORMATION: Xaa = Cys or Ser
<220> FEATURE:
<221> NAME/KEY: VARIANT
<222> LOCATION: 44
<223> OTHER INFORMATION: Xaa = Glu or Ala

<400> SEQUENCE: 50

Xaa Tyr Leu Xaa Lys Ile Xaa Asn Ser Xaa Ser Thr Glu Trp Ser Pro
1               5                   10                  15

Cys Ser Val Thr Xaa Gly Asn Gly Ile Gln Val Arg Ile Lys Pro Gly
            20                  25                  30

Ser Ala Asn Lys Pro Lys Asp Glu Leu Asp Tyr Xaa Asn Asp Ile Glu
        35                  40                  45

Lys Lys Ile Cys Lys Met Glu Lys Cys Ser Ser Val
    50                  55                  60

<210> SEQ ID NO 51
<211> LENGTH: 21
<212> TYPE: DNA
<213> ORGANISM: Artificial Sequence
<220> FEATURE:
<223> OTHER INFORMATION: Synthetic Construct

<400> SEQUENCE: 51
tcaccctcaa gttgggtaaa a                                            21

<210> SEQ ID NO 52
<211> LENGTH: 20
```

<212> TYPE: DNA
<213> ORGANISM: Artificial Sequence
<220> FEATURE:
<223> OTHER INFORMATION: Synthetic Construct

<400> SEQUENCE: 52
gcagagccag gctttattct                                           20

<210> SEQ ID NO 53
<211> LENGTH: 24
<212> TYPE: DNA
<213> ORGANISM: Artificial Sequence
<220> FEATURE:
<223> OTHER INFORMATION: Synthetic Construct

<400> SEQUENCE: 53
tgtaaaaatg tgtatgttgt gtgc                                      24

<210> SEQ ID NO 54
<211> LENGTH: 20
<212> TYPE: DNA
<213> ORGANISM: Artificial Sequence
<220> FEATURE:
<223> OTHER INFORMATION: Synthetic Construct

<400> SEQUENCE: 54
gtgcccatta cgactttgct                                           20

<210> SEQ ID NO 55
<211> LENGTH: 33
<212> TYPE: DNA
<213> ORGANISM: Artificial Sequence
<220> FEATURE:
<223> OTHER INFORMATION: Synthetic Construct

<400> SEQUENCE: 55
tgttacaatg aaggaaatga taataaattg tat                            33

<210> SEQ ID NO 56
<211> LENGTH: 27
<212> TYPE: DNA
<213> ORGANISM: Artificial Sequence
<220> FEATURE:
<223> OTHER INFORMATION: Synthetic Construct

<400> SEQUENCE: 56
tcttttggac atatattcat tttagca                                   27

<210> SEQ ID NO 57
<211> LENGTH: 25
<212> TYPE: PRT
<213> ORGANISM: Artificial Sequence
<220> FEATURE:
<223> OTHER INFORMATION: Synthetic Construct

<400> SEQUENCE: 57

Gly Ile Leu Glu Glu Glu Asp Asn Glu Ala Leu Arg Ala Pro Lys His
1               5                   10                  15

Lys Lys Leu Lys Gln Pro Glu Glu Leu
            20                  25

<210> SEQ ID NO 58
<211> LENGTH: 23
<212> TYPE: PRT
<213> ORGANISM: Artificial Sequence
<220> FEATURE:

```
<223> OTHER INFORMATION: Synthetic Construct

<400> SEQUENCE: 58

Gly Ile Leu Glu Glu Asp Asn Glu Ala Leu Arg Ala Pro Lys His Lys
1               5                   10                  15

Ala Leu Lys Gln Pro Glu Leu
            20

<210> SEQ ID NO 59
<211> LENGTH: 23
<212> TYPE: PRT
<213> ORGANISM: Artificial Sequence
<220> FEATURE:
<223> OTHER INFORMATION: Synthetic Construct

<400> SEQUENCE: 59

Gly Ile Leu Glu Glu Asp Asn Glu Ala Leu Arg Ala Pro Lys His Ala
1               5                   10                  15

Ala Leu Lys Gln Pro Glu Leu
            20

<210> SEQ ID NO 60
<211> LENGTH: 23
<212> TYPE: PRT
<213> ORGANISM: Artificial Sequence
<220> FEATURE:
<223> OTHER INFORMATION: Synthetic Construct

<400> SEQUENCE: 60

Gly Ile Leu Glu Glu Asp Asn Glu Ala Leu Arg Ala Pro Lys His Ala
1               5                   10                  15

Lys Leu Ala Gln Pro Glu Leu
            20

<210> SEQ ID NO 61
<211> LENGTH: 21
<212> TYPE: PRT
<213> ORGANISM: Artificial Sequence
<220> FEATURE:
<223> OTHER INFORMATION: Synthetic Construct

<400> SEQUENCE: 61

Gly Ile Leu Glu Asp Asn Glu Ala Leu Arg Ala Pro Lys His Ala Ala
1               5                   10                  15

Leu Ala Gln Pro Leu
            20

<210> SEQ ID NO 62
<211> LENGTH: 18
<212> TYPE: PRT
<213> ORGANISM: Artificial Sequence
<220> FEATURE:
<223> OTHER INFORMATION: Synthetic Construct

<400> SEQUENCE: 62

Gly Ile Leu Ala Asp Asn Glu Gly Leu Arg Lys Pro Lys His Ala Glu
1               5                   10                  15

Glu Leu

<210> SEQ ID NO 63
<211> LENGTH: 18
<212> TYPE: PRT
<213> ORGANISM: Artificial Sequence
<220> FEATURE:
```

<223> OTHER INFORMATION: Synthetic Construct

<400> SEQUENCE: 63

Gly Ile Leu Ala Asp Asn Glu Gly Leu Arg Lys Gly Lys His Ala Glu
1               5                   10                  15

Glu Leu

<210> SEQ ID NO 64
<211> LENGTH: 17
<212> TYPE: PRT
<213> ORGANISM: Artificial Sequence
<220> FEATURE:
<223> OTHER INFORMATION: Synthetic Construct

<400> SEQUENCE: 64

Gly Ile Leu Ala Asp Asn Glu Gly Gly Arg Gly Gly Lys His Ala Glu
1               5                   10                  15

Leu

<210> SEQ ID NO 65
<211> LENGTH: 12
<212> TYPE: PRT
<213> ORGANISM: Artificial Sequence
<220> FEATURE:
<223> OTHER INFORMATION: Synthetic Construct

<400> SEQUENCE: 65

Glu Asp Asn Glu Ala Leu Arg Lys Pro Lys His Lys
1               5                   10

<210> SEQ ID NO 66
<211> LENGTH: 28
<212> TYPE: PRT
<213> ORGANISM: Artificial Sequence
<220> FEATURE:
<223> OTHER INFORMATION: Synthetic Construct

<400> SEQUENCE: 66

Gly Ile Leu Glu Glu Tyr His Lys Ser Ser Thr Tyr Gly Lys Ala Ile
1               5                   10                  15

Ala Val Asp Ala Phe Ile Lys Lys Ile Glu Glu Leu
            20                  25

<210> SEQ ID NO 67
<211> LENGTH: 22
<212> TYPE: PRT
<213> ORGANISM: Artificial Sequence
<220> FEATURE:
<223> OTHER INFORMATION: Synthetic Construct

<400> SEQUENCE: 67

Gly Ile Leu Glu Tyr Asn Asn Asn Phe Cys Asn Thr Asn Gly Ile Arg
1               5                   10                  15

Tyr His Tyr Asp Glu Leu
            20

<210> SEQ ID NO 68
<211> LENGTH: 19
<212> TYPE: PRT
<213> ORGANISM: Artificial Sequence
<220> FEATURE:
<223> OTHER INFORMATION: Synthetic Construct

<400> SEQUENCE: 68

```
Gly Ile Leu Glu Thr Asn Gly Ile Arg Tyr His Tyr Asp Glu Tyr Ile
1               5                   10                  15

His Glu Leu

<210> SEQ ID NO 69
<211> LENGTH: 41
<212> TYPE: PRT
<213> ORGANISM: Artificial Sequence
<220> FEATURE:
<223> OTHER INFORMATION: Synthetic Construct

<400> SEQUENCE: 69

Gly Ile Leu Asp Arg Ala Asp Gly Gln Pro Ala Gly Asp Arg Ala Asp
1               5                   10                  15

Gly Gln Pro Ala Gly Asp Arg Ala Ala Gly Gln Pro Ala Gly Asp Arg
            20                  25                  30

Ala Ala Gly Gln Pro Ala Gly Asp Leu
        35                  40

<210> SEQ ID NO 70
<211> LENGTH: 40
<212> TYPE: PRT
<213> ORGANISM: Artificial Sequence
<220> FEATURE:
<223> OTHER INFORMATION: Synthetic Construct

<400> SEQUENCE: 70

Gly Ile Leu Ala Asn Gly Ala Gly Asn Gln Pro Gly Ala Asn Gly Ala
1               5                   10                  15

Gly Asn Gln Pro Gly Ala Asn Gly Ala Gly Asp Gln Pro Gly Ala Asn
            20                  25                  30

Gly Ala Gly Asp Gln Pro Gly Leu
        35                  40

<210> SEQ ID NO 71
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Glu or Ala
<220> FEATURE:
<221> NAME/KEY: VARIANT
<222> LOCATION: 5
<223> OTHER INFORMATION: Xaa = Ala or Gly
<220> FEATURE:
<221> NAME/KEY: VARIANT
<222> LOCATION: 6
<223> OTHER INFORMATION: Xaa = Leu or Gly
<220> FEATURE:
<221> NAME/KEY: VARIANT
<222> LOCATION: 8
<223> OTHER INFORMATION: Xaa = Ala, Lys, or Gly
<220> FEATURE:
<221> NAME/KEY: VARIANT
<222> LOCATION: 9
<223> OTHER INFORMATION: Xaa = Pro or Gly
<220> FEATURE:
<221> NAME/KEY: VARIANT
<222> LOCATION: 12
<223> OTHER INFORMATION: Xaa = Lys or Ala
<220> FEATURE:
<221> NAME/KEY: VARIANT
<222> LOCATION: 13
<223> OTHER INFORMATION: Xaa = Lys, Ala, or absent
<220> FEATURE:
```

```
<221> NAME/KEY: VARIANT
<222> LOCATION: 14
<223> OTHER INFORMATION: Xaa = Leu or absent
<220> FEATURE:
<221> NAME/KEY: VARIANT
<222> LOCATION: 15
<223> OTHER INFORMATION: Xaa = Lys, Ala, or absent
<220> FEATURE:
<221> NAME/KEY: VARIANT
<222> LOCATION: 16
<223> OTHER INFORMATION: Xaa = Gln or absent
<220> FEATURE:
<221> NAME/KEY: VARIANT
<222> LOCATION: 17
<223> OTHER INFORMATION: Xaa = Pro or absent

<400> SEQUENCE: 71

Xaa Asp Asn Glu Xaa Xaa Arg Xaa Xaa Lys His Xaa Xaa Xaa Xaa Xaa
1               5                   10                  15

Xaa

<210> SEQ ID NO 72
<211> LENGTH: 17
<212> TYPE: PRT
<213> ORGANISM: Artificial Sequence
<220> FEATURE:
<223> OTHER INFORMATION: Synthetic Construct

<400> SEQUENCE: 72

Glu Ala Asn Glu Lys Leu Arg Lys Pro Lys His Lys Lys Leu Lys Gln
1               5                   10                  15

Pro

<210> SEQ ID NO 73
<211> LENGTH: 17
<212> TYPE: PRT
<213> ORGANISM: Artificial Sequence
<220> FEATURE:
<223> OTHER INFORMATION: Synthetic Construct

<400> SEQUENCE: 73

Glu Asp Ala Glu Lys Leu Arg Lys Pro Lys His Lys Lys Leu Lys Gln
1               5                   10                  15

Pro

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Glu Asp Asn Glu Ala Leu Arg Lys Pro Lys His Lys Lys Leu Lys Gln
1               5                   10                  15

Pro

<210> SEQ ID NO 75
<211> LENGTH: 17
<212> TYPE: PRT
<213> ORGANISM: Artificial Sequence
<220> FEATURE:
<223> OTHER INFORMATION: Synthetic Construct

<400> SEQUENCE: 75

Glu Asp Asn Glu Lys Leu Arg Lys Pro Ala His Lys Lys Leu Lys Gln
```

-continued

```
1               5                   10                  15
Pro

<210> SEQ ID NO 76
<211> LENGTH: 17
<212> TYPE: PRT
<213> ORGANISM: Artificial Sequence
<220> FEATURE:
<223> OTHER INFORMATION: Synthetic Construct

<400> SEQUENCE: 76

Glu Asp Asn Glu Lys Leu Arg Lys Pro Lys Ala Lys Lys Leu Lys Gln
1               5                   10                  15
Pro

<210> SEQ ID NO 77
<211> LENGTH: 17
<212> TYPE: PRT
<213> ORGANISM: Artificial Sequence
<220> FEATURE:
<223> OTHER INFORMATION: Synthetic Construct

<400> SEQUENCE: 77

Glu Asp Asn Glu Lys Leu Arg Ala Pro Lys His Lys Lys Leu Ala Gln
1               5                   10                  15
Pro

<210> SEQ ID NO 78
<211> LENGTH: 17
<212> TYPE: PRT
<213> ORGANISM: Artificial Sequence
<220> FEATURE:
<223> OTHER INFORMATION: Synthetic Construct

<400> SEQUENCE: 78

Glu Asp Asn Glu Ala Leu Arg Ala Pro Lys His Lys Lys Leu Ala Gln
1               5                   10                  15
Pro

<210> SEQ ID NO 79
<211> LENGTH: 17
<212> TYPE: PRT
<213> ORGANISM: Artificial Sequence
<220> FEATURE:
<223> OTHER INFORMATION: Synthetic Construct

<400> SEQUENCE: 79

Glu Asp Asn Glu Ala Leu Arg Ala Pro Lys His Ala Ala Leu Ala Gln
1               5                   10                  15
Pro

<210> SEQ ID NO 80
<211> LENGTH: 17
<212> TYPE: PRT
<213> ORGANISM: Artificial Sequence
<220> FEATURE:
<223> OTHER INFORMATION: Synthetic Construct

<400> SEQUENCE: 80

Glu Asp Asn Glu Ala Leu Arg Ala Pro Lys His Lys Lys Leu Lys Gln
1               5                   10                  15
Pro
```

<210> SEQ ID NO 81
<211> LENGTH: 17
<212> TYPE: PRT
<213> ORGANISM: Artificial Sequence
<220> FEATURE:
<223> OTHER INFORMATION: Synthetic Construct

<400> SEQUENCE: 81

Glu Asp Asn Glu Ala Leu Arg Ala Pro Lys His Lys Ala Leu Lys Gln
1               5                   10                  15

Pro

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct

<400> SEQUENCE: 82

Glu Asp Asn Glu Ala Leu Arg Ala Pro Lys His Ala Ala Leu Lys Gln
1               5                   10                  15

Pro

<210> SEQ ID NO 83
<211> LENGTH: 17
<212> TYPE: PRT
<213> ORGANISM: Artificial Sequence
<220> FEATURE:
<223> OTHER INFORMATION: Synthetic Construct

<400> SEQUENCE: 83

Glu Asp Asn Glu Ala Leu Arg Ala Pro Lys His Ala Lys Leu Ala Gln
1               5                   10                  15

Pro

<210> SEQ ID NO 84
<211> LENGTH: 17
<212> TYPE: PRT
<213> ORGANISM: Artificial Sequence
<220> FEATURE:
<223> OTHER INFORMATION: Synthetic Construct

<400> SEQUENCE: 84

Glu Asp Asn Glu Ala Leu Arg Ala Pro Lys His Ala Ala Leu Ala Gln
1               5                   10                  15

Pro

<210> SEQ ID NO 85
<211> LENGTH: 229
<212> TYPE: PRT
<213> ORGANISM: Artificial Sequence
<220> FEATURE:
<223> OTHER INFORMATION: Synthetic Construct

<400> SEQUENCE: 85

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

```
Ser Pro His His Thr Ala Ile Arg Gln Ala Leu Val Cys Trp Asp Glu
 50                  55                  60

Leu Thr Lys Leu Ile Ala Trp Met Ser Ser Asn Ile Thr Ser Gly Ile
 65                  70                  75                  80

Leu Asp Arg Ala Asp Gly Gln Pro Ala Gly Asp Arg Ala Asp Gly Gln
                 85                  90                  95

Pro Ala Gly Asp Arg Ala Ala Gly Gln Pro Ala Gly Asp Arg Ala Ala
                100                 105                 110

Gly Gln Pro Ala Gly Asp Leu Glu Gln Val Arg Thr Ile Ile Val Asn
                115                 120                 125

His Val Asn Asp Thr Trp Gly Leu Lys Val Arg Gln Ser Leu Trp Phe
130                 135                 140

His Leu Ser Cys Leu Thr Phe Gly Gln His Thr Val Gln Glu Phe Leu
145                 150                 155                 160

Val Ser Phe Gly Val Trp Ile Arg Thr Pro Ala Pro Tyr Arg Pro Pro
                165                 170                 175

Asn Ala Pro Ile Leu Ser Thr Leu Pro Glu His Thr Val Ile Arg Arg
                180                 185                 190

Arg Gly Gly Ala Arg Ala Ser Arg Ser Pro Arg Arg Thr Pro Ser
                195                 200                 205

Pro Arg Arg Arg Arg Ser Gln Ser Pro Arg Arg Arg Ser Gln Ser
210                 215                 220

Pro Ser Ala Asn Cys
225

<210> SEQ ID NO 86
<211> LENGTH: 205
<212> TYPE: PRT
<213> ORGANISM: Artificial Sequence
<220> FEATURE:
<223> OTHER INFORMATION: Synthetic Construct

<400> SEQUENCE: 86

Met Asp Ile Asp Pro Tyr Lys Glu Phe Gly Ser Ser Tyr Gln Leu Leu
 1                5                  10                  15

Asn Phe Leu Pro Leu Asp Phe Phe Pro Asp Leu Asn Ala Leu Val Asp
                 20                  25                  30

Thr Ala Thr Ala Leu Tyr Glu Glu Glu Leu Thr Gly Arg Glu His Cys
                 35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Thr Ser Gly Ile
 65                  70                  75                  80

Leu Glu Glu Asp Asn Glu Lys Leu Arg Lys Pro Lys His Glu Leu Glu
                 85                  90                  95

Gln Val Arg Thr Ile Ile Val Asn His Val Asn Asp Thr Trp Gly Leu
                100                 105                 110

Lys Val Arg Gln Ser Leu Trp Phe His Leu Ser Cys Leu Thr Phe Gly
                115                 120                 125

Gln His Thr Val Gln Glu Phe Leu Val Ser Phe Gly Val Trp Ile Arg
130                 135                 140

Thr Pro Ala Pro Tyr Arg Pro Pro Asn Ala Pro Ile Leu Ser Thr Leu
145                 150                 155                 160

Pro Glu His Thr Val Ile Arg Arg Arg Gly Gly Ala Arg Ala Ser Arg
                165                 170                 175
```

```
Ser Pro Arg Arg Arg Thr Pro Ser Pro Arg Arg Arg Ser Gln Ser
            180                 185                 190

Pro Arg Arg Arg Arg Ser Gln Ser Pro Ser Ala Asn Cys
        195                 200                 205

<210> SEQ ID NO 87
<211> LENGTH: 205
<212> TYPE: PRT
<213> ORGANISM: Artificial Sequence
<220> FEATURE:
<223> OTHER INFORMATION: Synthetic Construct

<400> SEQUENCE: 87

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Gly Ile
65                  70                  75                  80

Leu Glu Glu Asn Ala Ile Lys Lys Thr Lys Asn Gln Glu Glu Leu Glu
                85                  90                  95

Gln Val Arg Thr Ile Ile Val Asn His Val Asn Asp Thr Trp Gly Leu
            100                 105                 110

Lys Val Arg Gln Ser Leu Trp Phe His Leu Ser Cys Leu Thr Phe Gly
        115                 120                 125

Gln His Thr Val Gln Glu Phe Leu Val Ser Phe Gly Val Trp Ile Arg
    130                 135                 140

Thr Pro Ala Pro Tyr Arg Pro Pro Asn Ala Pro Ile Leu Ser Thr Leu
145                 150                 155                 160

Pro Glu His Thr Val Ile Arg Arg Arg Gly Gly Ala Arg Ala Ser Arg
                165                 170                 175

Ser Pro Arg Arg Arg Thr Pro Ser Pro Arg Arg Arg Ser Gln Ser
            180                 185                 190

Pro Arg Arg Arg Arg Ser Gln Ser Pro Ser Ala Asn Cys
        195                 200                 205

<210> SEQ ID NO 88
<211> LENGTH: 68
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4
<223> OTHER INFORMATION: Xaa = Glu or Asp, and can be present or absent
<220> FEATURE:
<221> NAME/KEY: VARIANT
<222> LOCATION: (5)..(64)
<223> OTHER INFORMATION: Xaa = Any Amino Acid, and each Xaa can be
      present or absent
<220> FEATURE:
<221> NAME/KEY: VARIANT
<222> LOCATION: 65, 66, 67, 68
<223> OTHER INFORMATION: Xaa = Glu or Asp, and each Xaa can be present
      or absent

<400> SEQUENCE: 88
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa
65

<210> SEQ ID NO 89
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2
<223> OTHER INFORMATION: Xaa = Asp, and can be present or absent
<220> FEATURE:
<221> NAME/KEY: VARIANT
<222> LOCATION: (3)..(122)
<223> OTHER INFORMATION: Xaa = Any Amino Acid, and each Xaa can be
      present or absent
<220> FEATURE:
<221> NAME/KEY: VARIANT
<222> LOCATION: 123, 124
<223> OTHER INFORMATION: Xaa = Ile, and can be present or absent

<400> SEQUENCE: 89

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa
        115                 120

<210> SEQ ID NO 90
<211> LENGTH: 20
<212> TYPE: PRT
<213> ORGANISM: Artificial Sequence
<220> FEATURE:
<223> OTHER INFORMATION: Synthetic Construct

<400> SEQUENCE: 90

Asn Ala Asn Pro Asn Ala Asn Pro Asn Ala Asn Pro Asn Ala Asn Pro
1               5                   10                  15

Asn Ala Asn Pro
            20
```

```
<210> SEQ ID NO 91
<211> LENGTH: 16
<212> TYPE: PRT
<213> ORGANISM: Artificial Sequence
<220> FEATURE:
<223> OTHER INFORMATION: Synthetic Construct

<400> SEQUENCE: 91

Asp Pro Asn Ala Asn Pro Asn Val Asp Pro Asn Ala Asn Pro Asn Val
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Synthetic Construct

<400> SEQUENCE: 92

Asn Ala Asn Pro Asn Ala Asn Pro Asn Ala Asn Pro Asn Ala Asn Pro
1               5                   10                  15

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Asn Val Asp Pro Asn Val Asp Pro
1               5

<210> SEQ ID NO 94
<211> LENGTH: 64
<212> TYPE: PRT
<213> ORGANISM: Artificial Sequence
<220> FEATURE:
<223> OTHER INFORMATION: Synthetic Construct

<400> SEQUENCE: 94

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
    50                  55                  60
```

HYBRID HEPADNAVIRUS CORES CARRYING MULTIPLE MALARIA PARASITE EPITOPES

CROSS-REFERENCE TO RELATED APPLICATIONS

This application is a continuation of International Application No. PCT/US2017/030475, filed May 1, 2017, which claims benefit of U.S. Provisional Application No. 62/330,137, filed Apr. 30, 2016, the contents of which are hereby incorporated by reference in their entirety.

STATEMENT REGARDING FEDERALLY SPONSORED RESEARCH

This invention was made in part with government support under Grant No. RO1AI082740 awarded by the National Institute of Allergy and Infectious Diseases, of the National Institutes of Health. The government has certain rights in the invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 720222000301SeqList.txt, dated recorded: Mar. 26, 2019, size: 65 KB).

FIELD

The present disclosure relates to rodent hepadnavirus core antigens including one or more B cell and T cell epitopes of a malaria parasite antigen. More specifically, the present disclosure relates to hybrid woodchuck hepadnavirus core antigens that have been modified to diminish the antibody response to the core antigen so as to enhance the antibody response to fragments of malaria antigen(s) included therein.

BACKGROUND

Malaria is an important tropical parasitic disease that kills more people than any other communicable disease with the exception of tuberculosis. The causative agents in humans are four species of Plasmodium protozoa: P. falciparum, P. vivax, P. ovale and P. malariae. Of these, P. falciparum is the most lethal. The vast majority of deaths occur among young children in Africa. P. vivax is the most prevalent species outside of sub-Saharan Africa and is responsible for approximately 50% of all malaria cases worldwide (Guerra et al., Trends Parasitol, 22:353-358, 2006). Malaria is a public health problem today in more than 100 countries, inhabited by over half of the world's population. Worldwide prevalence of the disease is extraordinarily high and malaria mortality is estimated to be about 500,000 per year (Murray et al., The Lancet, 379:413-431, 2012). P. falciparum malaria has 14 chromosomes, an estimated 5,300 genes (many of which vary extensively between strains) and a complex four-stage life cycle as it passes from a mosquito vector to humans and back again. Furthermore, the natural P. falciparum infection does not result in sterile immunity, and partial immunity occurs only after years of recurring infections and illnesses. Therefore, a useful human vaccine must out perform the immune response to the natural infection. This complexity and the lack of suitable animal models has impeded vaccine development against both P. falciparum and P. vivax.

All stages of the P. falciparum life cycle have been targeted for malaria vaccine development, however, only preerythrocytic stage immunogens (i.e., the circumsporozoite protein and the multiepitope-thrombospondin-related adhesion protein) have been shown to elicit significant clinical efficacy (Stoute et al., J Infect Dis, 178:1139-44, 1988; and Webster et al., Proc Natl Acad Sci USA, 102: 4836-4861, 2005). Only one circumsporozoite (CS) protein vaccine candidate, known as RTS,S or Mosquirix™ developed by GSK (London, United Kingdom) has reached phase III clinical trials. RTS,S is a recombinant subunit vaccine, which includes a fusion protein produced by fusing a fragment of a single allele (e.g., 3D7) of the CS protein fused to the hepatitis B surface antigen (HBsAg). RTS,S has been in development for over two decades and tested in multiple experimental and field trials (see, e.g., Alonso et al., Lancet, 364:1411-20, 2004; and Aponte et al., Lancet, 370:1543-51, 2007). In brief, protective efficacy of three doses of RTS,S formulated in a combination of three relatively potent adjuvants is reported to be between 30 and 50% as judged by prevention of clinical and severe malaria, although the level of protection is dependent on malaria transmission intensity, age and time since vaccination (Olotu et al., N Engl J Med, 368:1111-1120, 2013). Development of RTS,S is a significant achievement and demonstrates that a recombinant subunit vaccine containing only isolated B and T cell epitopes from a single CS protein delivered on a heterologous carrier can elicit protection in humans. However, it is generally acknowledged that "second generation" vaccines will be necessary for full implementation of a malaria vaccine intended for all at-risk populations (i.e., endemic populations, travelers to endemic regions and the military). The search for second generation preerythrocytic vaccine candidates has included use of the entire CS protein, addition of other preerythrocytic antigens, new adjuvants, DNA delivery, viral vectors, prime-boost strategies, etc., with little success to date (Duffy et al., Expert Rev Vaccines, 11:1261, 2012).

Thus what the art needs are more immunogenic malaria vaccine candidates that target one or both of the preerythrocyte and erythrocyte stages of Plasmodium. Specifically, next generation malaria vaccines that confer protection in a greater proportion of vaccinated subjects are desirable. Particularly desirable malaria vaccine candidates targeting the pre-erythrocyte stage contain B cell epitopes of two or more alleles of the CS protein. Malaria vaccine candidates targeting both P. falciparum and P. vivax are especially desirable. Ideally the protection conferred would be long-lived.

SUMMARY

The present disclosure relates to rodent hepadnavirus core antigens including one or more B cell and T cell epitopes of a malaria parasite antigen. More specifically, the present disclosure relates to hybrid woodchuck hepadnavirus core antigens that have been modified to diminish the antibody response to the core antigen so as to enhance the antibody response to fragments of malaria antigen(s) included therein.

BRIEF DESCRIPTION OF THE DRAWINGS

FIG. 1A-B shows B and T cell epitopes of the circumsporozoite coat protein (CS). FIG. 1A is a schematic representation of the Pf and hybrid Pb/Pf sporozoites. Native *P. berghei* sequence is indicated by light shading and transgenic *P. falciparum* sequence by dark shading. Neutralizing B-cell epitopes are denoted by black bars and CD4+ T cell epitopes by white bars. The "repeats" epitope (140-159) is part of a much larger motif, delineated by the dotted line. Numbering is based on the amino acid sequence of CSP from the 7G8 clone. FIG. 1B lists virus like particles (VLPs) described in the examples. In summary, Mal: NANP and NVDP repeats; Mal5: NANP repeat only; Ct: carboxy-terminal; TH: TH.3R and UTC epitopes; 3T: insertion of all 3 T cell epitopes; C61S: Cys-to-Ser mutation at position 61 of WHcAg; Pv: *P. vivax* B cell repeats. Each of the epitopes is genetically inserted into the sequence of the VLP gene and a fully-assembled VLP consists of 120 homodimers. Thus each VLP includes 240 copies of the inserted epitope(s).

FIG. 3B shows protection against liver stage Pb/Pf infection. Mice were injected with 500 µl of indicated rabbit antisera and challenged with 10,000 sporozoites i.v. shortly after receiving the antisera. Liver burden was determined by qPCR 40 hours after challenge. Control, normal mouse sera. P values are for Mann-Whitney U-test comparing in each case the 5 mice per group, ns=not significant at the 0.05 significance level. FIG. 3C shows protection against blood stage Pb/Pf infection. 200 µl of sera from rabbit #74 or from a control naïve rabbit were passively transferred to groups of 7 or 4 mice, respectively, by i.v. injection. Mice were then challenged by allowing 3, 5, 6 or 12 mosquitoes infected with Pb/Pf sporozoites to feed on the mice for 5 min. Mice were bled daily starting on day 4 post-challenge and blood-stage infection assessed by microscopy on stained blood smears.

FIG. 5A shows liver burden as assessed by determining parasite 18S rRNA copies in the liver. Circles represent individual mice, boxes represent mean values. P values are for Mann-Whitey U-test between groups for each formulation, with each group having six mice, except the Mal-3T in alum group, which had five mice. FIG. 5B shows post-boost antibody levels in pooled sera were determined by ELISA using rCSP, NANP or NVDP peptides as solid phase ligands. IFA titers were performed on dry Pb/Pf sporozoites.

FIG. 6A-C shows protective efficacy of WHc(C61S)-Mal-78-3T immunization against *P. berghei/P. falciparum* blood stage malaria infection. Groups of ten mice were primed and boosted with 100 µg of WHc(C61S)-Mal-78-3T formulated in alum (250 µg/dose), alum+QS21 (20 µg/dose) or emulsified in Montanide ISA720 (50% vol/vol) and boosted in alum as indicated. FIG. 6A is a time line showing schedule of prime, boost and challenge with 12 mosquitoes infected with Pb/Pf hybrid sporozoites allowed to feed on the mice for 5 min. After feeding, mosquitoes were examined for blood in the gut, confirming that multiple mosquitoes had fed on each animal. FIG. 6B is a graphic representation of the percentage of mice remaining protected (i.e., free of blood stage parasites) during the 14 day monitoring period. FIG. 6C is a summary of results. One mouse from the Alum+QS21 group died before challenge.

FIG. 7A-C shows protective efficacy of WHc-Pv-78 (VLP-206) immunization against *P. berghei/P. vivax* malaria infection. Mice were primed and boosted with 100 µg of WHc-Pv-78 or WHcAg emulsified in IFAd (50% vol/vol). In FIG. 7A mice were challenged with 10,000 Pb/Pv sporozoites injected in the tail vein and liver infection determined by qPCR. P value is for the Mann-Whitney U-test with four mice in the WHc-Pv-78 group and five mice in the control WHc group. In FIG. 7B-C mice were exposed to the bites of 10 Pb/Pv-infected mosquitoes for 5 min, after which, mosquitoes were examined for blood in the gut to confirm that multiple mosquitoes had fed on each animal. Malarial infection was determined by blood smear during the 14 day monitoring period. The amino acid sequence of VLP-206 is set forth as SEQ ID NO:85.

FIG. 10A shows the resulting amino acid sequence of the hybrid CS protein (SEQ ID NO:21), which includes N-terminal sequence derived from *P. berghei* (ANKA) and C-terminal sequence derived from *P. falciparum* (3D7). FIG. 10B shows an alignment illustrating conservation of T cell epitopes on *P. berghei* CS (SEQ ID NO:22) and *P. falciparum* CS (SEQ ID NO:23). The *P. falciparum* T cell domain was incorporated into the WHc(C61S)-Mal-78-3T VLP (VLP-162). The percentages represent identities and similarities (homologies) between the two sequences.

FIG. 11 shows selection criteria for hybrid woodchuck hepadnavirus cores carrying multiple epitopes of multiple malaria parasite stages.

FIG. 12 is a comparison of vaccine features of WHc (C61S)-Mal-78-3T (VLP-162) versus previous generation malaria VLPs RTS,S (MOSQUIRIX™ malaria vaccine of GlaxoSmithKline Biologicals, S.A., of Rixensart, Belgium) and ICC-1132 (MALARIVAX™ malaria vaccine developed by of Immune Complex Corporation, later Apovia Inc., San Diego, Calif.).

FIG. 13 provides an alignment of amino acid sequences of woodchuck hepadnavirus core antigen (WHcAg) and derivatives thereof. Asterisks denote amino acid identity. The amino acid sequences of the woodchuck hepadnavirus core antigens are set forth as follows: WHcAg as SEQ ID NO:1; delta2WHcAg as SEQ ID NO:2; delta3WHcAg as SEQ ID NO:3; delta4WHcAg as SEQ ID NO:4; delta5WHcAg as SEQ ID NO:5; delta6WHcAg as SEQ ID NO:6; delta7WHcAg as SEQ ID NO:7. The amino acid sequence of various other hepadnavirus core antigens are also provided herein: GScAg as SEQ ID NO:8, AGScAg as SEQ ID NO:9; and HBcAg as SEQ ID NO:10.

FIG. 14A is a schematic representation of WHc(C61S)-Mal-78-3T (also referred to herein as VLP-162). FIG. 14B provides an alignment of the amino acid sequences of the wild type full length WHcAg (SEQ ID NO:1) and VLP-162 (SEQ ID NO:20).

FIG. 15A provides an alignment of the amino acid sequences of the wild type full length WHcAg (SEQ ID NO:1) and VLP-206 (SEQ ID NO:85). FIG. 15B provides an alignment of the amino acid sequences of the wild type full length WHcAg (SEQ ID NO:1) and VLP-245 (SEQ ID NO:86).

DESCRIPTION

Figure 2:
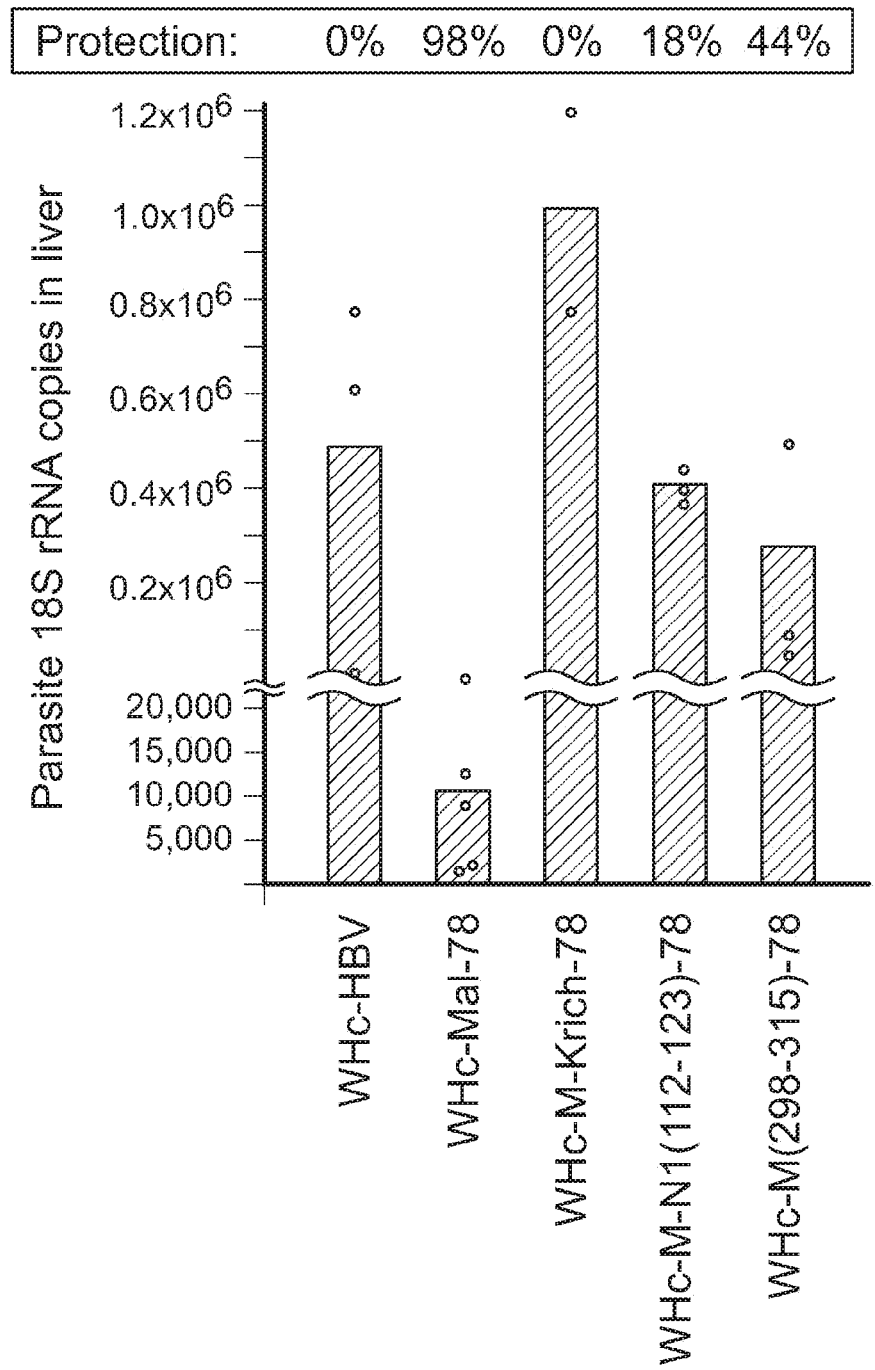
FIG. 2 is a comparison of protective efficacy of WHc-CS VLPs. Groups of mice were immunized with WHc-HBV negative control and CS-repeat (WHc-Mal-78) VLPs (2 doses of 20 µg and 10 µg in IFAd): CS-non-repeat VLPs (3 doses of 20 µg, 10 µg, 10 µg in IFAd). From 2 to 3.5 months after the last immunization dose all mice were challenged with 10,000 Pb/Pf sporozoites. Parasite 18S rRNA copy number in the liver was determined by qPCR 40 hours after infection. Circles represent individual mice and the bars represent mean values. % protection is based on mean values in comparison to the WHc-HBV negative control.

The present disclosure relates to rodent hepadnavirus core antigens including one or more B cell and T cell epitopes of a malaria parasite antigen. More specifically, the present disclosure relates to hybrid woodchuck hepadnavirus core antigens that have been modified to diminish the antibody response to the core antigen so as to enhance the antibody response to fragments of malaria antigen(s) included therein.

In order to design *P. falciparum* preerythrocytic vaccine candidates, a library of circumsporozoite (CS) T and B cell epitopes displayed on the woodchuck hepatitis virus core antigen (WHcAg) VLP platform was produced. To test the protective efficacy of the WHcAg-CS VLPs, hybrid CS *P. berghei/P. falciparum* (Pb/Pf) sporozoites were used to challenge immunized mice. VLPs carrying one or two different CS repeat B cell epitopes and three VLPs carrying different CS non-repeat B cell epitopes elicited high levels of anti-insert antibodies (Abs). VLPs carrying CS repeat B cell epitopes conferred 98% protection of the liver against a 10,000 Pb/Pf sporozoite challenge. In contrast, VLPs carrying the CS non-repeat B cell epitopes were minimally-to-non-protective. One-to-three CS-specific CD4/CD8 T cell sites were also fused to VLPs, which primed CS-specific, as well as WHcAg-specific T cells. However, a VLP carrying only the three T cell epitopes failed to protect against a sporozoite challenge, indicating a requirement for anti-CS repeat Abs. A VLP carrying two CS repeat B cell epitopes and three CS T cell epitopes in alum adjuvant elicited high titer anti-CS Abs (endpoint dilution titer>1×10$^6$) and provided 80-100% protection against blood stage malaria. Using a similar strategy, VLPs were constructed carrying *P. vivax* CS repeat B cell epitopes (WHc-Pv-78), which elicited high levels of anti-CS Abs and conferred 99% protection of the liver against a 10,000 Pb/Pv sporozoite challenge and elicited sterile immunity to blood stage infection. These results indicate that immunization with epitope-focused VLPs carrying selected B and T cell epitopes from the *P. falciparum* and *P. vivax* CS proteins can elicit sterile immunity against blood stage malaria. Thus, hybrid WHcAg-CS VLPs are suitable for use as a bivalent *P. falciparum/P. vivax* malaria vaccine.

Rodent Hepadnavirus Core Antigens

Exemplary rodent hepadnavirus core antigens of the present disclosure include woodchuck (WHcAg), ground squirrel (GScAg), arctic ground squirrel (AGScAg) hepadnavirus core antigens. Rodent hepadnavirus core antigens have been chosen as carriers in part because they are multimeric, self-assembling, virus-like particles (VLP). The basic subunit of the core particle is a 21 kDa polypeptide monomer that spontaneously assembles into a 240 subunit particulate structure of about 34 nm in diameter. The tertiary and quaternary structures of hepadnavirus core particles have been elucidated (Conway et al., Nature, 386:91-94, 1997). The immunodominant B cell epitope on hepadnavirus core particles is localized around amino acids 76-82 (Schodel et al., J Exp Med, 180:1037-1046, 1994) forming a loop connecting adjacent alpha-helices. This observation is consistent with the finding that a heterologous antigen inserted within the 76-82 loop region of HBcAg was significantly more antigenic and immunogenic than the antigen inserted at the N- or C-termini and, importantly, more immunogenic than the antigen in the context of its native protein (Schodel et al., J Virol, 66:106-114, 1992).

Full length and truncated wild type WHcAg cores, as well as recombinant WHcAg cores containing various mutations are suitable for use as carriers for malaria antigens for production of hybrid VLPs. Some preferred recombinant WHcAg cores are listed in Table I. The WHcAg particles were designed to include either a heterologous B cell epitope within the WHcAg immunodominant loop extending from residues 76-82 of wild type WHcAg (Δ1 mutation), or alter endogenous WHcAg-specific B cell epitopes in order to reduce WHcAg-specific antigenicity and/or immunogenicity without negatively affecting the antigenicity and/or immunogenicity of heterologous B cell epitopes inserted within the WHcAg. The mutations designed to decrease WHcAg-specific antigenicity and/or immunogenicity are designated as Δ2-Δ7 mutations or modifications. These modified WHcAg carrier platforms provide an advantageous system for presentation of heterologous antigens (hAg), such as malaria antigens.

In some embodiments, the woodchuck hepadnavirus core antigen with reduced antigenicity comprises one, two, three, four or five modifications of the group consisting of the Δ2-Δ7 modifications. Exemplary combinations of modifications include: Δ2 and one or more of Δ3, Δ4, Δ5, Δ6.x and Δ7.x; Δ3 and one or more of Δ2, Δ4, Δ5, Δ6.x and Δ7.x; Δ4 and one or more of Δ2, Δ3, Δ5, Δ6.x and Δ7.x; Δ5 and one or more of Δ2, Δ3, Δ4, Δ6.x and Δ7.x; Δ6 and one or more of Δ2, Δ3, Δ4, Δ5.x and Δ7.x; and Δ7 and one or more of Δ2, Δ3, Δ4, Δ5.x and Δ6.x.

In some embodiments, the present disclosure provides a woodchuck hepadnavirus core antigen with reduced antigenicity, which comprises SEQ ID NO:12, SEQ ID NO:13, or a variant thereof that is at least 90% identical (e.g., at least 90%, 91%, 92%, 93%, 94%, 95%, 96%, 97%, 98%, or 99% identical) to SEQ ID NO:12 or SEQ ID NO:13. In some preferred embodiments, the variant is at least 95% identical to SEQ ID NO:12 or SEQ ID NO:13, but does not comprise SEQ ID NO:11 or SEQ ID NO:1. In some embodiments, the woodchuck hepadnavirus core antigen with reduced antigenicity comprises one of the amino acid sequences selected from the group consisting of SEQ ID NO:2, SEQ ID NO:3, SEQ ID NO:4, SEQ ID NO:5, SEQ ID NO:6 and SEQ ID NO:7.

TABLE I

WHcAg Mutations Affecting Antigenicity and/or Immunogenicity

| Designation | Description |
|---|---|
| Δ1 | WHcAg/insertion of a heterologous antigen within the immunodominant loop |
| Δ2 | WHcAg/L21A, D26A, L27A, N28A, A29V, V31A substitutions |
| Δ3 | WHcAg/N136P, A137P substitutions |
| Δ4 | WHcAg/C61S substitution |
| Δ5 | WHcAg/replacement of residues 62-85, 65-88 or 64-87 with a heterologous antigen |
| Δ6 | WHcAg/R150A, R151A, R152A, R156A, R159A, R162A, R163A, R164A, R169A, R170A, R171A, R177A, R178A, R179A, R180A substitutions |
| Δ6.1 | WHcAg/R150A, R151A, R152A, R156A, R159A, R162A, R163A, R164A, R169A, R170A, R171A substitutions |
| Δ7 | WHcAg/N75A, I76A, T77A, S78A, E79A, Q80A, V81A, R82A, T83A substitutions |
| Δ7.1 | WHcAg/N75A, I76S, T77S, S78E, E79L, Q80E, V81L, R82E, T83L substitutions |

Heterologous Antigens

A heterologous antigen (hAg) of the present disclosure is a polypeptide that is different from a woodchuck hepadnavirus core antigen. In particular, when used to refer to a portion of a fusion protein or a hybrid core antigen comprising a woodchuck hepadnavirus core antigen and a heterologous antigen, the term heterologous antigen refers to the portion, which is not derived from or does not otherwise correspond to the woodchuck hepadnavirus core antigen. In some embodiments, the heterologous antigen is a polypeptide of from 4 to 120 amino acids in length. Unless otherwise indicated, the term heterologous antigen refers to a malaria antigen throughout the present disclosure.

In some embodiments, the heterologous antigen comprises one B cell epitope, while in others it comprises two, three, four or five B cell epitopes, or even a larger plurality of B cell epitopes. In some preferred embodiments, the heterologous antigen further comprises one T cell epitope, or it comprises two, three, four or five T cell epitopes, or even a larger plurality of T cell epitopes. In some embodiments, the T cell epitope is a helper T (Th) cell epitope (MHC class II-restricted epitope). In some embodiments, the T cell epitope is a cytotoxic T cell (CTL) epitope (MHC class I-restricted epitope). Determination as to whether a given heterologous antigen of a hybrid core antigen comprises a B cell epitope can be made by analyzing heterologous antigen-specific antibody-binding of serum of a subject immunized with the hybrid core antigen (or polynucleotide encoding the hybrid core antigen). Determination as to whether a given heterologous antigen of a hybrid core antigen comprises a Th cell epitope can be made by analyzing heterologous antigen-induced proliferation or cytokine secretion by peripheral blood lymphocytes (PBL) of a subject immunized with the hybrid core antigen (or polynucleotide encoding the hybrid core antigen). Determination as to whether a given heterologous antigen of a hybrid core antigen comprises a CTL cell epitope can be made by analyzing heterologous antigen-specific lysis of a target cell that expresses the heterologous antigen by CTL expanded from PBL of a subject immunized with a polynucleotide encoding the hybrid core antigen. Other methods of determining whether a heterologous antigen or fragment thereof comprises B, Th and/or CTL epitopes are known in the art.

The heterologous antigen of the hybrid VLPs of the present disclosure may comprise a fragment of a surface protein. In other embodiments, the heterologous antigen comprises a fragment of a secreted protein. In other embodiments, the heterologous antigen comprises a fragment of a cytosolic protein. In still further embodiments, the heterologous antigen is itself a fusion protein comprising fragments of two, three, four or five different polypeptides.

The hybrid VLPs of the present disclosure comprise at least one malaria antigen as the heterologous antigen. In some embodiments, the malaria antigen has the amino acid sequence of an antigen derived from P. falciparum, P. vivax, P. ovale or P. malariae or is at least 90% identical thereto (e.g., at least 90%, 91%, 92%, 93%, 94%, 95%, 96%, 97%, 98%, or 99% identical to a malaria antigen or fragment thereof). In some preferred embodiments, the malaria antigen is at least 95% identical to an antigen derived from P. falciparum, P. vivax, P. ovale or P. malariae. In some embodiments, the malaria antigen is inserted at a position within the woodchuck hepadnavirus core antigen selected from the group consisting of N-terminal, 44, 71, 72, 73, 74, 75, 76, 77, 78, 81, 82, 83, 84, 85, 92, 149 and C-terminal as numbered according to SEQ ID NO:1. In some embodiments, the malaria antigen is inserted between pairs of amino acids that are noncontiguous within the wild type sequence prior to deletion of the intervening amino acids of the woodchuck hepadnavirus core antigen. For instance, in some embodiments the malaria antigen is inserted between the following amino acids 69/79, 70/80, 71/81, 72/82, 73/83, or 75/81 of the woodchuck hepadnavirus core antigen as numbered according to SEQ ID NO:1. In some preferred embodiments, the malaria antigen comprises two or more polypeptides. In some particularly preferred embodiments, the two or more polypeptides comprises a B cell domain (polypeptide of from 4 to 60 amino acids in length containing at least one B cell epitope) and a T cell domain (polypeptide of from 8 to 120 amino acids in length containing at least one T cell epitope). In some embodiments, the B cell domain is inserted in or adjacent to the immunodominant loop of the woodchuck hepadnavirus core antigen, preferably at a position within the woodchuck hepadnavirus core antigen selected from the group consisting of 61, 71, 72, 73, 74, 75, 76, 77, 78, 81, 82, 83, 84, 85, and 92 as numbered according to SEQ ID NO:1. In some embodiments, the T cell domain is inserted at the carboxyl end of the woodchuck hepadnavirus core antigen or truncated variant thereof.

One preferred malaria antigen is the circumsporozoite (CS) protein. Exemplary B cell domains and flanking linkers for polypeptide inserts within or adjacent to the immunodominant loop of WHcAg are listed in Table II. Exemplary T cell domains for polypeptide inserts at the C-terminus of WHcAg are listed in Table III.

TABLE II

Malaria Polypeptides Containing B Cell Epitopes

| Name | N-linker | Malaria Sequence | C-linker | SEQ ID NO. |
|---|---|---|---|---|
| Mal^ | GIL | NANP NVDP NANP NANP NANP | L | 24 |
| Mal1 | GIL | DP NANP NVDP NANP NV | L | 25 |
| Mal2 | GIL | NP NVDP NANP NVDP NA | L | 26 |
| Mal3 | GIL | NVDP NANP NVDP | L | 27 |
| Mal4 | GIL | NANP NVDP NANP NVDP | L | 28 |
| Mal5 | GILE | NANP NANP NANP NANP | EL | 29 |
| Krich(93-113) | GILEE | DEDKRDGNNEDNEKLRKPKHKKL | EEL | 30 |
| N1(112-123) | GILE | KLKQPGDGNPDP | EL | 31 |
| CSP(298-315) | GIL | HNMPNDPNRNVDENANAN | L | 32 |
| PfCSP(81-91)3D7 | GILE | EDNEKLRKPKH | EL | 33 |
| PfCSP(77-91)3D7 | GILE | DGNNEDNEKLRKPKH | EL | 34 |
| PfCSP(81-94)3D7 | GILEEE | EDNEKLRKPKHKKL | EEEL | 35 |
| PfCSP(81-97)3D7 | GILEEE | EDNEKLRKPKHKKLQP | EEEL | 36 |
| PfRH5(26-36)3D7 | GILE | ENAIKKTKNQE | EL | 37 |
| 5A08Mimo | GILEE | SAIKKPVT | EEL | 38 |
| PfRH5(200-213A)3D7 | GILE | YGKAIAVDAFIKKINE | EL | 39 |
| PfRH5(353-360A)3D7 | GILD | TNGIRYAYD | L | 40 |
| CSP(81-97)2KA | GILEE | EDNEALRAPKHKKLQP | EEL | 57 |
| CSP(81-97)3KA | GILE | EDNEALRAPKHKALKQP | EL | 58 |
| CSP(81-97)4KA93 | GILE | EDNEALRAPKHAALKQP | EL | 59 |
| CSP(81-97)4KA95 | GILE | EDNEALRAPKHAKLAQP | EL | 60 |
| CSP(81-97)5KA | GIL | EDNEALRAPKHAALAQP | L | 61 |
| CSP(82-92)Gly1 | GIL | ADNEGLRKPKHA | EEL | 62 |
| CSP(82-92)Gly2 | GIL | ADNEGLRKGKHA | EEL | 63 |
| CSP(82-92)Gly3 | GIL | ADNEGGRGGKHA | EL | 64 |
| CSP(81-92)K85A | | EDNEALRKPKHK | | 65 |
| Rh5(194-213A) | GILEE | YHKSSTYGKAIAVDAFIKKI | EEL | 66 |
| Rh5(346-360) | GILE | YNNNFCNTNGIRYHYD | EL | 67 |
| Rh5(353-360) | GILE | TNGIRYHYDEYIH | EL | 68 |
| Pv (VK210) | GIL | DRADGQPAGDRADGQPAGDRAAGQPAGDRAAGQPAGD | L | 69 |
| Pv (VK247) | GIL | ANGAGNQPGANGAGNQPGANGAGDQPGANGAGDQPG | L | 70 |
| CSP(81-97)con | | XDNEXXRXXK HXXXXXX<br>where X @ position:<br>1 = E or A,<br>5 = A or G,<br>6 = L or G,<br>8 = A, K or G,<br>9 = P or G,<br>12 = K or A,<br>13 = K, A or absent,<br>14 = L or absent, | | 71 |

TABLE II-continued

Malaria Polypeptides Containing B Cell Epitopes

| Name | N-linker | Malaria Sequence | C-linker | SEQ ID NO. |
|------|----------|------------------|----------|------------|
|      |          | 15 = K, A or absent,<br>16 = Q of absent, and<br>17 = P or absent. |          |            |

^Mal was inserted many places. Minimally, 74, 75, 77, 78, 75/81, 92, Cterm, Nterm, where in 75/81 the malaria sequence inserted between WHc amino acids 75 and 81 with 76-80 deleted.

TABLE III

Malaria Polypeptides Containing T Cell Epitopes

| Name | Malaria Sequence | SEQ ID NO. |
|------|------------------|------------|
| PfUTC (333-352) | EYLNKIQNSLSTEWSPCSVT | 41 |
| PfTH.3R (354-378) | GNGIQVRIKPGSANKPKDELDYEN | 42 |
| PfCS.T3 (378-392) | DIEKKICKMEKCSSV | 43 |
| PbUTC (333-352) | EFVKQIRDSITEEWSQCNVT | 44 |
| PbTH.3R (354-378) | GSGIRVRKRKGSNKKAEDLTLEDI | 45 |
| PBCS.T3 (378-392) | DTEICKMDKCSSIFN | 46 |
| 7G8-3TC | QYLKKIKNSISTEWSPCSVT C<br>GNGIQVRIKPGSANKPKDELDYEN DIEKKICKMEKCSSV | 47 |
| 3D7-3TC | EYLNKIQNSLSTEWSPCSVT C<br>GNGIQVRIKPGSANKPKDELDYAN DIEKKICKMEKCSSV | 48 |
| 3TC | EYLNKIQNSLSTEWSPCSVT S<br>GNGIQVRIKPGSANKPKDELDYEN DIEKKICKMEKCSSV | 49 |
| 3TCcon | XYLXKIXNSXSTEWSPCSVT X<br>GNGIQVRIKPGSANKPKDELDYXN DIEKKICKMEKCSSV<br>where X @ position:<br>1 = Q or E, 4 = K or N, 7 = K or Q,<br>10 = I or L, 21 = C or S, and 44 = E or A. | 50 |

Nucleic acid sequences encoding polypeptide inserts were either designed to contain unique enzyme restriction sites, or overlapping oligonucleotides were designed to insert the sequence into the pUC-WHcAg vector. For some inserts, the restriction sites utilized result in the inclusion of N-terminal and C-terminal linkers flanking the malaria polypeptide insert.

The standard linker/insert combination of hybrid VLPs comprising a malaria antigen within or adjacent to the immunodominant loop of WHcAg is GIL-Xn-L, where Xn is an insert, X is any amino acid, and n is 60 or less (SEQ ID NO:17). The malaria antigen is optionally flanked on one or both sides by one or more negatively charged amino acids glutamic acid (E) or aspartic acid (D) such that Xn can be represented by the formula [E/D]y-MaAg-[E/D]z in which both y and z are integers independently selected from the group consisting of 0, 1, 2, 3 and 4, and MaAg is a malaria antigen of up to 60 amino acids in length (SEQ ID NO:88).

The linker/insert combination of hybrid VLPs comprising a malaria antigen at the N-terminus of WHcAg is Xn-WLWG, where Xn is an insert, X is any amino acid, and n is 60 or less (SEQ ID NO:18). The linker/insert combination of hybrid VLPs comprising a malaria antigen at the C-terminus of WHcAg is [D]y[I]z-Xm in which both y and z are integers independently selected from the group consisting of 0, 1 and 2, where Xm is an insert, X is any amino acid, and m is up to 120 amino acids in length (SEQ ID NO:89).

As indicated above, the B cell domain (containing at least one B cell epitope) is from 4 to 60 amino acids in length, preferably 5 to 55 amino acids in length, preferably 10 to 50 amino acids in length, preferably 15 to 45 amino acids in length, or preferably 20 to 40 amino acids in length. In some embodiments, the length of the B cell domain is within any range having a lower limit of 4, 5, 6, 7, 8, 9, 10, 11, 12, 13, 14, 15, 16, 17, 18, 19 or 20 amino acids and an independently selected upper limit of 60, 55, 50, 45, 40, 35, 30, 25 or 20 amino acids in length, provided that the lower limit is less than the upper limit.

Likewise as indicated above, the T cell domain (containing at least one T cell epitope) is from 8 to 120 amino acids in length, preferably 10 to 110 amino acids in length, preferably 20 to 100 amino acids in length, or preferably 25 to 50 amino acids in length. In some embodiments, the length of the T cell domain is within any range having a lower limit of 8, 9, 10, 11, 12, 13, 14, 15, 16, 17, 18, 19, 20, 25 or 30 amino acids and an independently selected upper limit of 120, 110, 100, 90, 80, 70, 60, 55, 50, 45, 40, 35 or 30 amino acids in length, provided that the lower limit is less than the upper limit.

Development of Fusion Proteins and Hybrid Particles

A problem inherent to the insertion of heterologous epitope sequences into VLP genes is that such manipulation can abolish self-assembly. This assembly problem is so severe that several groups working with the HBcAg or with other VLP technologies (e.g., the L1 protein of the human papillomavirus and Qβ phage) have opted to chemically link the foreign epitopes to the VLPs rather than inserting the epitopes into the particles by recombinant methods. The need to chemically conjugate heterologous antigens has been circumvented by development of combinatorial technology (Billaud et al., J Virol, 79:13656-13666, 2005). This was achieved by determining 17 different insertion sites and 28 modifications of the WHcAg C-terminus that together favor assembly of chimeric particles, as well as the identification of a number of additional improvements (see, e.g., U.S. Pat. Nos. 7,144,712; 7,320,795; and 7,883,843). Table IV lists categories of hybrid particles, based on whether modifications to the hAg insert sequence, the WHcAg carrier sequence, the linker sequence (residues separating WHcAg and hAg sequences), insert position and/or replacement of carrier with insert sequence are present. ELISA-based screening systems have been developed that measure expression levels, VLP assembly, and insert antigenicity using crude bacterial lysates, avoiding the need to employ labor-intensive purification steps for hybrid VLPs that do not express and/or assemble well.

TABLE IV

Categories of Hybrid, WHcAg-hAg VLP Mutants

| Category | Description |
| --- | --- |
| standard | heterologous polypeptide inserted at position 78 within the immunodominant loop |
| epitope-modified | alterations affecting the heterologous polypeptide |
| carrier-modified | alterations affecting the WHcAg carrier |
| linker-modified | addition or deletion of heterologous polypeptide linkers |
| varied position | insertion of the heterologous polypeptide at a position tolerant of assembly other than position 78 of the WHcAg carrier |
| replacement | replacement of WHcAg carrier residues with a heterologous polypeptide |

Antigenic and Immunogenic Characterization of Hybrid, WHcAg-hAg VLPs

A. Antigenicity

Prior to immunogenicity testing, hybrid WHcAg-hAg VLPs are characterized for expression, particle assembly, and ability to bind a hAg-specific antibody. The same capture ELISA system used to detect hybrid VLPs in bacterial lysates may be used for purified particles. In brief, expression, particle assembly, and antibody binding are assayed by ELISA. SDS-PAGE and Western blotting are used to assess the size and antigenicity of hybrid VLPs.

B. Immunogenicity

The immune response to hybrid VLPs is assessed. In addition to anti-insert, anti-hAg-protein and anti-WHcAg antibody endpoint titers, antibody specificity, isotype distribution, antibody persistence and antibody avidity are monitored. Immune sera are compared to the activity of a reference antibody by ELISA and neutralization assays. Immune responses are tested in vivo in various mammalian species (e.g., rodents such as rats and mice, nonhuman primates, humans, etc.).

Compositions

The compositions of the present disclosure comprise a hybrid woodchuck hepadnavirus core antigen or a polynucleotide encoding the hybrid core antigen, wherein the hybrid core antigen is a fusion protein comprising a heterologous polypeptide and a woodchuck hepadnavirus core antigen, wherein the fusion protein is capable of assembling as a hybrid virus-like particle (VLP). In some embodiments, the heterologous polypeptide comprises at least one B cell epitope (e.g., capable of being bound by an antibody). In preferred embodiments, the composition is an antigenic composition. In some embodiments, the composition further comprises a pharmaceutically acceptable carrier. The term "carrier" refers to a vehicle within which the hybrid core antigen or polynucleotide encoding the antigen is administered to a mammalian subject. The term carrier encompasses diluents, excipients, adjuvants and combinations thereof. Pharmaceutically acceptable carriers are well known in the art (see, e.g., Remington's Pharmaceutical Sciences by Martin, 1975).

Exemplary "diluents" include sterile liquids such as sterile water, saline solutions, and buffers (e.g., phosphate, tris, borate, succinate, histidine, etc.). Exemplary "excipients" are inert substances include but are not limited to polymers (e.g., polyethylene glycol), carbohydrates (e.g., starch, glucose, lactose, sucrose, cellulose, etc.), and alcohols (e.g., glycerol, sorbitol, xylitol, etc.).

Adjuvants are broadly separated into two classes based upon their primary mechanism of action: vaccine delivery systems (e.g., emulsions, microparticles, iscoms, liposomes, etc.) that target associated antigens to antigen presenting cells (APC); and immunostimulatory adjuvants (e.g., LPS, MLP, CpG, etc.) that directly activate innate immune responses. The WHcAg platform provides a delivery system that targets antigen specific B cells and other primary APC, as well as efficient T cell help for antigen-specific B cells. Additionally, the core platform functions as an immunostimulatory adjuvant by directly activating antigen-specific B cells by virtue of cross-linking membrane immunoglobulin (mIg) receptors for induction of B7.1 and B7.2 costimulatory molecule expression on naive resting B cells (Milich et al., Proc Natl Acad Sci USA, 94:14648-14653, 1997).

A. Traditional and Molecular Adjuvants

Although adjuvants are not required when using the WHcAg delivery system, some embodiments of the present disclosure employ traditional and/or molecular adjuvants. Specifically, immunization in saline effectively elicits anti-insert antibody production. However, formulation in non-inflammatory agents such as IFA (mineral oil), Montanide ISA 720 (squalene), and aluminum phosphate (AIP04), enhance immunogenicity. Additionally, administration of WHcAg results in the production of all four IgG isotypes, regardless of which if any adjuvant is employed. Inclusion of a CpG motif also enhances the primary response. Moreover, use of an inflammatory adjuvant such as the Ribi formulation is not more beneficial than is the use of non-inflammatory adjuvants, indicating that the benefits of the adjuvants result from a depot effect rather than from nonspecific inflammation. Thus, the core platform is used with no adjuvant or with non-inflammatory adjuvants depending upon the application and the quantity of antibody desired. In some embodiments of the present disclosure, IFA is used in murine studies, whereas alum or squalene is used in human studies. In instances where it is desirable to deliver hybrid WHcAg particles in a single dose in saline, a molecular adjuvant is employed. A number of molecular adjuvants are employed to bridge the gap between innate and adaptive immunity by providing a co-stimulus to target B cells or other APCs.

B. Other Molecular Adjuvants

Genes encoding the murine CD40L (both 655 and 470 nucleic acid versions) have been used successfully to express these ligands at the C-terminus of WHcAg (See, WO 2005/011571). Moreover, immunization of mice with hybrid WHcAg-CD40L particles results in the production of higher anti-core antibody titers than does the immunization of mice with WHcAg particles. However, lower than desirable yields of purified particles have been obtained. Therefore, mosaic particles containing less than 100% CD40L-fused polypeptides are produced to overcome this problem. The other molecular adjuvants inserted within the WHcAg, including the C3d fragment, BAFF and LAG-3, have a tendency to become internalized when inserted at the C-terminus. Therefore tandem repeats of molecular adjuvants are used to resist internalization. Alternatively, various mutations within the so-called hinge region of WHcAg, between the assembly domain and the DNA/RNA-binding region of the core particle are made to prevent internalization of C-terminal sequences. However, internalization represents a problem for those molecular adjuvants such as CD40L, C3d, BAFF and LAG-3, which function at the APC/B cell membrane. In contrast, internalization of molecular adjuvants such as CpG DN is not an issue as these types of adjuvants function at the level of cytosolic receptors.

Another type of molecular adjuvant or immune enhancer is the inclusion within hybrid core particles of a CD4+ T cell epitope, preferably a "universal" CD4+ T cell epitope that is recognized by a large proportion of CD4+ T cells (such as by more than 50%, preferably more than 60%, more preferably more than 70%, most preferably greater than 80%), of CD4+ T cells. In one embodiment, universal CD4+ T cell epitopes bind to a variety of human MHC class II molecules and are able to stimulate T helper cells. In another embodiment, universal CD4+ T cell epitopes are preferably derived from antigens to which the human population is frequently exposed either by natural infection or vaccination (Falugi et al., Eur J Immunol, 31:3816-3824, 2001). A number of such universal CD4+ T cell epitopes have been described including, but not limited to: Tetanus Toxin (TT) residues 632-651; TT residues 950-969; TT residues 947-967, TT residues 830-843, TT residues 1084-1099, TT residues 1174-1189 (Demotz et al., Eur J Immunol, 23:425-432, 1993); Diphtheria Toxin (DT) residues 271-290; DT residues 321-340; DT residues 331-350; DT residues 411-430; DT residues 351-370; DT residues 431-450 (Diethelm-Okita et al., J Infect Dis, 1818:1001-1009, 2000); *Plasmodium falciparum* circumsporozoite (CSP) residues 321-345 and CSP residues 378-395 (Hammer et al., Cell, 74:197-203, 1993); Hepatitis B antigen (HBsAg) residues 19-33 (Greenstein et al., J Immunol, 148:3970-3977, 1992); Influenza hemagglutinin residues 307-319; Influenza matrix residues 17-31 (Alexander et al., J Immunol, 164:1625-1633, 2000); and measles virus fusion protein (MVF) residues 288-302 (Dakappagari et al., J Immunol, 170:4242-4253, 2003).

Methods of Inducing an Immune Response

The present disclosure provides methods for eliciting an immune response in an animal in need thereof, comprising administering to the animal an effective amount of an antigenic composition comprising a hybrid woodchuck hepadnavirus core antigen, wherein the hybrid core antigen is a fusion protein comprising a heterologous antigen and a woodchuck hepadnavirus core antigen with reduced antigenicity, and wherein said fusion protein assembles as a hybrid virus-like particle (VLP). Also provided by the present disclosure are methods for eliciting an immune response in an animal in need thereof, comprising administering to the animal an effective amount of an antigenic composition comprising a polynucleotide encoding a hybrid woodchuck hepadnavirus core antigen, wherein the hybrid core antigen is a fusion protein comprising a heterologous antigen and a woodchuck hepadnavirus core antigen with reduced antigenicity, and wherein said fusion protein assembles as a hybrid virus-like particle (VLP). Unless otherwise indicated, the antigenic composition is an immunogenic composition.

The immune response raised by the methods of the present disclosure generally includes an antibody response, preferably a neutralizing antibody response, preferably a protective antibody response. Methods for assessing antibody responses after administration of an antigenic composition (immunization or vaccination) are well known in the art. In some embodiments, the immune response comprises a T cell-mediated response (e.g., heterologous antigen-specific response such as a proliferative response, a cytokine response, etc.). In preferred embodiments, the immune response comprises both a B cell and a T cell response. Antigenic compositions can be administered in a number of suitable ways, such as intramuscular injection, subcutaneous injection, and intradermal administration. Additional modes of administration include but are not limited to intranasal administration, and oral administration.

Antigenic compositions may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >55 years old, >60 years old, preferably >65 years old), and the young (e.g., <6 years old, 1-5 years old, preferably less than 1 year old).

Administration can involve a single dose or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naive subjects or subjects of a hyporesponsive population (e.g., diabetics, subjects with chronic kidney disease, etc.). Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.). Preferably multiple doses are administered from one, two, three, four or five months apart. Antigenic compositions of the present disclosure may be administered to patients at substantially the same time as (e.g., during the same medical consultation or visit to a healthcare professional) other vaccines.

In general, the amount of protein in each dose of the antigenic composition is selected as an amount effective to induce an immune response in the subject, without causing significant, adverse side effects in the subject. Preferably the immune response elicited is a neutralizing antibody, preferably a protective antibody response. Protective in this context does not necessarily mean the subject is completely protected against infection, rather it means that the subject is protected from developing symptoms of disease, especially severe disease associated with the pathogen corresponding to the heterologous antigen.

The amount of hybrid core antigen (e.g., VLP) can vary depending upon which antigenic composition is employed. Generally, it is expected that each human dose will comprise 1-1500 µg of protein (e.g., hybrid core antigen), such as from about 1 µg to about 1000 µg, for example, from about 1 µg to about 500 µg, or from about 1 µg to about 100 µg. In some embodiments, the amount of the protein is within any range having a lower limit of 10, 20, 30, 40, 50, 60, 70, 80, 90, 100, 110, 120, 130, 140, 150, 160, 170, 180, 190, 200, 210, 220, 230, 240 or 250 µg, and an independently selected upper limit of 1000, 950, 900, 850, 800, 750, 700, 650, 600, 550, 500, 450, 400, 350, 300 or 250 µg, provided that the lower limit is less than the upper limit. Generally a human dose will be in a volume of from 0.1 ml to 1 ml, preferably from 0.25 ml to 0.5 ml. The amount utilized in an immunogenic composition is selected based on the subject population. An optimal amount for a particular composition can be ascertained by standard studies involving observation of antibody titers and other responses (e.g., antigen-induced cytokine secretion) in subjects. Following an initial vaccination, subjects can receive a boost in about 4-12 weeks.

Kits

Also provided by the present disclosure are kits comprising a hybrid woodchuck hepadnavirus core antigen and a woodchuck hepadnavirus core antigen, wherein the hybrid core antigen is a fusion protein comprising a heterologous antigen and a woodchuck hepadnavirus core antigen with reduced antigenicity, and wherein said fusion protein assembles as a hybrid virus-like particle (VLP), and wherein the core antigen lacks the heterologous antigen. In some embodiments, the kits further comprise instructions for measuring heterologous antigen-specific antibodies. In some embodiments, the antibodies are present in serum from a blood sample of a subject immunized with an antigenic composition comprising the hybrid woodchuck hepadnavirus core antigen.

As used herein, the term "instructions" refers to directions for using reagents (e.g., a hybrid core antigen and a core antigen) contained in the kit for measuring antibody titer. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination.

Definitions

As used herein, the singular forms "a", "an", and "the" include plural references unless indicated otherwise. For example, "an" excipient includes one or more excipients. The term "plurality" refers to two or more.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Current Protocols in Molecular Biology (Ausubel et al., eds., 1987); PCR: The Polymerase Chain Reaction, (Mullis et al., eds., 1994); Culture of Animal Cells: A Manual of Basic Technique (Freshney, 1987); Harlow et al., Antibodies: A Laboratory Manual (Harlow et al., 1988); and Current Protocols in Immunology (Coligan et al., eds., 1991).

As used herein, the terms "virus-like particle" and "VLP" refer to a structure that resembles a virus. VLPs of the present disclosure lack a viral genome and are therefore noninfectious. Preferred VLPs of the present disclosure are woodchuck hepadnavirus core antigen (WHcAg) VLPs.

The terms "hybrid" and "chimeric" as used in reference to a hepadnavirus core antigen, refer to a fusion protein of the hepadnavirus core antigen and an unrelated antigen (e.g., bacterial polypeptide, and variants thereof). For instance, in some embodiments, the term "hybrid WHcAg" refers to a fusion protein comprising both a WHcAg component (full length, or partial) and a heterologous antigen or fragment thereof.

The term "heterologous" with respect to a nucleic acid, or a polypeptide, indicates that the component occurs where it is not normally found in nature and/or that it originates from a different source or species.

An "effective amount" or a "sufficient amount" of a substance is that amount necessary to effect beneficial or desired results, including clinical results, and, as such, an "effective amount" depends upon the context in which it is being applied. In the context of administering an immunogenic composition, an effective amount contains sufficient antigen (e.g., hybrid, WHcAg-hAg VLP) to elicit an immune response (preferably a measurable level of hAg pathogen-neutralizing antibodies). An effective amount can be administered in one or more doses.

The term "dose" as used herein in reference to an immunogenic composition refers to a measured portion of the immunogenic composition taken by (administered to or received by) a subject at any one time.

The term "about" as used herein in reference to a value, encompasses from 90% to 110% of that value (e.g., about 200 μg VLP refers to 180 μg to 220 μg VLP).

As used herein the term "immunization" refers to a process that increases an organisms' reaction to antigen and therefore improves its ability to resist or overcome infection.

The term "vaccination" as used herein refers to the introduction of vaccine into a body of an organism.

A "variant" when referring to a polynucleotide or a polypeptide (e.g., a viral polynucleotide or polypeptide) is a polynucleotide or a polypeptide that differs from a reference polynucleotide or polypeptide. Usually, the difference(s) between the variant and the reference constitute a proportionally small number of differences as compared to the reference (e.g., at least 90%, 91%, 92%, 93%, 94%, 95%, 96%, 97%, 98% or 99% identical). In some embodiments, the present disclosure provides hybrid WHcAg-hAg VLPs having at least one addition, insertion or substitution in one or both of the WHcAg or hAg portion of the VLP.

The term "wild type" when used in reference to a polynucleotide or a polypeptide refers to a polynucleotide or a polypeptide that has the characteristics of that polynucleotide or a polypeptide when isolated from a naturally-occurring source. A wild type polynucleotide or a polypeptide is that which is most frequently observed in a population and is thus arbitrarily designated as the "normal" form of the polynucleotide or a polypeptide.

Amino acids may be grouped according to common side-chain properties: hydrophobic (Met, Ala, Val, Leu, Ile); neutral hydrophilic (Cys, Ser, Thr, Asn, Gln); acidic (Asp, Glu); basic (His, Lys, Arg); aromatic (Trp, Tyr, Phe); and orientative (Gly, Pro). Another grouping of amino acids according to side-chain properties is as follows: aliphatic (glycine, alanine, valine, leucine, and isoleucine); aliphatic-hydroxyl (serine and threonine); amide (asparagine and glutamine); aromatic (phenylalanine, tyrosine, and tryptophan); acidic (glutamic acid and aspartic acid); basic (lysine, arginine, and histidine); sulfur (cysteine and methionine); and cyclic (proline). In some embodiments, the amino acid substitution is a conservative substitution involving an exchange of a member of one class for another member of the same class. In other embodiments, the amino acid substitution is a non-conservative substitution involving an exchange of a member of one class for a member of a different class.

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. A "recombinant" protein is one that is encoded by a heterologous (e.g., recombinant) nucleic acid, which has been introduced into a host cell, such as a bacterial or eukaryotic cell. The nucleic acid can be introduced, on an expression vector having signals capable of expressing the protein encoded by the introduced nucleic acid or the nucleic acid can be integrated into the host cell chromosome.

An "antigen" is a compound, composition, or substance that can stimulate the production of antibodies and/or a T cell response in a subject, including compositions that are injected, absorbed or otherwise introduced into a subject. The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. Thus, with respect to a protective immune response against a pathogen, the dominant antigenic epitopes are those antigenic moieties that when recognized by the host immune system result in protection from disease caused by the pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

"Adjuvant" refers to a substance which, when added to a composition comprising an antigen, nonspecifically enhances or potentiates an immune response to the antigen in the recipient upon exposure. Common adjuvants include suspensions of minerals (alum, aluminum hydroxide, aluminum phosphate) onto which an antigen is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

An "antibody" or "immunoglobulin" is a plasma protein, made up of four polypeptides that binds specifically to an antigen. An antibody molecule is made up of two heavy chain polypeptides and two light chain polypeptides (or multiples thereof) held together by disulfide bonds. In humans, antibodies are defined into five isotypes or classes: IgG, IgM, IgA, IgD, and IgE. IgG antibodies can be further divided into four sublclasses (IgG1, IgG2, IgG3 and IgG4). A "neutralizing" antibody is an antibody that is capable of inhibiting the infectivity of a virus. Accordingly, a neutralizing antibodies specific for a virus are capable of inhibiting or reducing infectivity of the virus.

An "immunogenic composition" is a composition of matter suitable for administration to a human or animal subject (e.g., in an experimental or clinical setting) that is capable of eliciting a specific immune response, e.g., against a pathogen, such as a malaria parasite. As such, an immunogenic composition includes one or more antigens (for example, polypeptide antigens) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., virus) following exposure of the subject to the pathogen. In the context of this disclosure, the term immunogenic composition will be understood to encompass compositions that are intended for administration to a subject or population of subjects for the purpose of eliciting a protective or palliative immune response against a virus (that is, vaccine compositions or vaccines).

An "immune response" is a response of a cell of the immune system, such as a B cell, T cell, or monocyte, to a stimulus, such as a pathogen or antigen (e.g., formulated as an immunogenic composition or vaccine). An immune response can be a B cell response, which results in the production of specific antibodies, such as antigen specific neutralizing antibodies. An immune response can also be a T cell response, such as a CD4+ response or a CD8+ response. B cell and T cell responses are aspects of a "cellular" immune response. An immune response can also be a "humoral" immune response, which is mediated by antibodies. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo. Exposure of a subject to an immunogenic stimulus, such as a pathogen or antigen (e.g., formulated as an immunogenic composition or vaccine), elicits a primary immune response specific for the stimulus, that is, the exposure "primes" the immune response. A subsequent exposure, e.g., by immunization, to the stimulus can increase or "boost" the magnitude (or duration, or both) of the specific immune response. Thus, "boosting" a preexisting immune response by administering an immunogenic composition increases the magnitude of an antigen (or pathogen) specific response, (e.g., by increasing antibody titer and/or affinity, by increasing the frequency of antigen specific B or T cells, by inducing maturation effector function, or any combination thereof).

The term "reduces" is a relative term, such that an agent reduces a response or condition if the response or condition is quantitatively diminished following administration of the agent, or if it is diminished following administration of the agent, as compared to a reference agent. Similarly, the term "protects" does not necessarily mean that an agent completely eliminates the risk of an infection or disease caused by infection, so long as at least one characteristic of the response or condition is substantially or significantly reduced or eliminated. Thus, an immunogenic composition that protects against or reduces an infection or a disease, or symptom thereof, can, but does not necessarily prevent or eliminate infection or disease in all subjects, so long as the incidence or severity of infection or incidence or severity of disease is measurably reduced, for example, by at least about 50%, or by at least about 60%, or by at least about 70%, or by at least about 80%, or by at least about 90% of the infection or response in the absence of the agent, or in comparison to a reference agent.

A "subject" refers to a mammalian subject. In the context of this disclosure, the subject can be an experimental subject, such as a non-human mammal (e.g., mouse, rat, rabbit, non-human primate, etc.). Alternatively, the subject can be a human subject.

The terms "derived from" or "of" when used in reference to a nucleic acid or protein indicates that its sequence is identical or substantially identical to that of an organism of interest.

The terms "decrease," "reduce" and "reduction" as used in reference to biological function (e.g., enzymatic activity, production of compound, expression of a protein, etc.) refer to a measurable lessening in the function by preferably at least 10%, more preferably at least 50%, still more preferably at least 75%, and most preferably at least 90%. Depending upon the function, the reduction may be from 10% to 100%. The term "substantial reduction" and the like refers to a reduction of at least 50%, 75%, 90%, 95% or 100%.

The terms "increase," "elevate" and "elevation" as used in reference to biological function (e.g., enzymatic activity, production of compound, expression of a protein, etc.) refer to a measurable augmentation in the function by preferably at least 10%, more preferably at least 50%, still more preferably at least 75%, and most preferably at least 90%. Depending upon the function, the elevation may be from 10% to 100%; or at least 10-fold, 100-fold, or 1000-fold up to 100-fold, 1000-fold or 10,000-fold or more. The term "substantial elevation" and the like refers to an elevation of at least 50%, 75%, 90%, 95% or 100%.

The terms "isolated" and "purified" as used herein refers to a material that is removed from at least one component with which it is naturally associated (e.g., removed from its original environment). The term "isolated," when used in reference to a recombinant protein, refers to a protein that has been removed from the culture medium of the host cell (e.g., bacteria) that produced the protein. As such an isolated protein is free of extraneous compounds (e.g., culture medium, bacterial components, etc.).

EXAMPLES

Abbreviations: Ab (antibody); AGScAg (arctic ground squirrel hepadnavirus core antigen); BSA (bovine serum albumin); CS (circumsporozoite); ELISA (enzyme-linked immunosorbent assay); GScAg (ground squirrel hepadnavirus core antigen); HBcAg (human hepatitis B virus core antigen); (hAg) heterologous antigen; IFA (immunofluorescence assay); MAb or mAb (monoclonal antibody); Mal (malaria); OD (optical density); PBS (phosphate buffered saline); Pb (*P. berghei*); Pf (*P. falciparum*); Pv (*P. vivax*); VLP (virus-like particle); WHcAg (woodchuck hepadnavirus core antigen); and WT (wild type).

Example 1

Hybrid Woodchuck Hepadna Virus Core Antigens Containing Malaria Epitopes Elicit Sterile Immunity to Blood Stage Infections This examples describes the production and testing of *P. falciparum* preerythrocytic vaccine candidates, which comprise B and T cell epitopes of the circumsporozoite (CS) protein displayed on woodchuck hepadna virus core antigen (WHcAg) virus-like particles (VLPs).

Materials And Methods

Animals. The (B10×B10.$) F1 mice used in VLP screening and immunogenicity evaluation were obtained from the breeding colony of the Vaccine Research Institute of San Diego (VRISD). The B6 mice used for protection studies were obtained from NCI (Fredrick, Md.). The rabbits used for immunogenicity testing were New Zealand White rabbits obtained from ProSci Inc. (Poway, Calif.). All animal care was performed according to National Institutes of Health standards as set forth in the Guide for the Care and Use of Laboratory Animals (2011).

Recombinant WHcAg hybrid VLP Construction. The woodchuck hepadnavirus genome has previously been described (Cohen et al., Virology, 162:12-20, 1998), GENBANK Accession No. NC_004107 (SEQ ID NO:16). The WHcAg and hybrid WHcAg VLPs were expressed from the pUC-WHcAg vector expressing the full-length WHcAg protein codon optimized for expression in E. coli [18]. For inserting heterologous B cell epitopes, EcoRI-XhoI restriction sites were engineered into the open reading frame between amino acids 78 and 79 of the core protein gene. The engineered restriction sites add a Gly-Ile-Leu linker on the N-terminal side and a Leu linker on the C-terminal side of the inserted epitopes. For fusing heterologous T cell epitopes, an EcoRV restriction site was engineered at the 3' end of the WHcAg gene, which adds an Asp-Ile linker between the WHcAg gene and the fused epitopes. Epitopes were cloned into the VLP gene using synthetic oligonucleotides comprising the desired epitope coding sequence and the appropriate engineered restriction sites. The WHc(C61S) point mutation to reduce carrier antigenicity was constructed by PCR using primer mismatches to create point mutations. All WHcAg constructs were transformed into Alpha-Select competent E. coli (Bioline USA, Inc.) and confirmed by DNA sequencing. Inserted B cell epitope sequences were exactly matched to the CSP sequence from clone 7G8 of P. falciparum used in the construction of the CS(Pf) or the VK210 repeat from Salvador I strain of P. vivax used in the construction of the Pb/Pv hybrid sporozoites, respectively. The inserted T cell epitopes had only one conservative mismatch, i.e., Cys 283 of the CS protein in the new Pb-Pf-CSP-CT hybrid sporozoites is a Ser in the VLPs with the TH and 3T T cell epitope sequences.

Some of the hybrid WHcAg VLPs were constructed on full length (SEQ ID NO:1) or truncated WHcAg cores (SEQ ID NO:2), while others were constructed on full length or truncated WHcAg cores comprising modifications. Some WHcAg modifications were previously described in U.S. Pat. No. 7,320,795. Other WHcAg modifications were made so as to reduce carrier-specific antigenicity, and include: Δ2-WHcAg, Δ3-WHcAg, Δ4-WHcAg, Δ5-WHcAg, Δ6-WHcAg, Δ6.1-WHcAg, Δ7-WHcAg, and Δ7.1-WHcAg (described above in Table I).

Purified Proteins and Synthetic Peptides. The VLP particles were expressed in Alpha-Select E. coli cells grown in Terrific Broth (Teknova, Hollister, Calif.). Cells were lysed by passage through an EmulsiFlex-C3 (Avestin, Ottawa, ON, Canada) and the lysate heated to 65° C. for approximately 10 min, then clarified by centrifugation. The WHcAg particles were selectively precipitated by the addition of solid ammonium sulfate to approximately 45% saturation (277 g/L) and the precipitates were collected by centrifugation. Precipitated VLPs were re-dissolved in minimum buffer (10 mM Tris, pH 8), dialized against the same buffer and applied to a Sepharose CL4B column (5×100 cm). Finally, VLPs were formulated in 20 mM Tris, pH8, 100 mM NaCl. Endotoxin was removed from the core preparations by phase separation with Triton X-114 [19,20]. Briefly, the VLP solution was made 1% Triton X-114 and incubated at 4° C. for 30 min with mixing, incubated at 37° C. for 10 min, centrifuged at 20K×G for 10 min and the protein recovered in the upper phase. This was repeated for 4 extractions. The purified VLPs were 0.2 um sterile-filtered, characterized and aliquoted. Characterization typically includes custom ELISA, native agarose gel electrophoresis, PAGE, heat stability, circular dichroism and dynamic light scattering as previously described [18,21].

Recombinant CS protein was produced from the CS27 IV C clone (MRA-272, MR4, ATCC Manassas, Va.) obtained through the Malaria Research and Reference Reagent Resource Center (www.mr4.org) and deposited by Photini Sinnis [22]. The open reading frame was moved to the pQE-60 vector (Qiagen) and transformed into M15 E. coli cells (Qiagen). Integrity of the gene was confirmed by DNA sequencing before purification by standard methods. Briefly, LB medium, supplemented with 2 g/L glucose, 25 µg/ml Kanamycin and 50 µg/ml Ampicilin, was inoculated with a 1:40 dilution of overnight culture. Bacteria were grown at 37° C. to an A600 of 0.8-1.0, isopropyl β-D-1-thiogalactopyranoside added to a concentration of 100 mg/L, grown 3 hours longer and harvested by centrifugation. Cells were suspended in lysis buffer (25 mM Tris, pH 8, 0.3 M NaCl, 10 mM imidazole) and lysed by a single passage through an Avestin EmulsiFlex-C3 (Ottawa, ON, Canada). The lysate was clarified by centrifugation at 48,000×G for 30 min, and applied to a nickel column (BioRad Profinity IMAC). Unbound proteins were removed by elution with the lysis buffer, then bound proteins were eluted in the same buffer containing 100 mM imidazole. This procedure yielded approximately 10 mg of pure protein per liter of cultured bacteria.

Synthetic peptides derived from the WHcAg or CS sequences were synthesized by Eton Biosciences (San Diego, Calif.).

Immunizations and serology. Groups of mice were immunized intraperitoneally (i.p.) with the WHcAg hybrid VLPs (usually 10-20 µg) emulsified in incomplete Freund's adjuvant (IFAd) for both antibody production and T cell experiments. The dose was varied when other adjuvants were used, i.e., saline (200 µg) and alum (100 µg). For mouse experiments, mice were bled retro-orbitally and sera pooled from each group. Periodically individual mouse sera were tested to confirm the fidelity of the pooled sera results. Anti-WHc and anti-insert immunoglobulin G (IgG) antibodies were measured in murine sera by an indirect solid-phase ELISA by using the homologous WHcAg (50 ng/well) or synthetic peptides (0.5 µg/well), representing the inserted sequence, as solid-phase ligands as described previously [15]. Serial dilutions of both test sera and pre-immunization sera were made and the data are expressed as antibody titers representing the reciprocals of the highest dilutions of sera required to yield an optical density at 492 nm (OD 492) three times an equal dilution of pre-immunization sera. IgG isotype-specific ELISAs were performed by using IgG1-, IgG2a-, IgG2b- and IgG3-specific peroxidase-labeled secondary antibodies (Southern Biotechnology, Birmingham, Ala.). Rabbits were immunized with WHcAg hybrid VLPs (200 µg in IFAd) and boosted either with 200 µg in saline or 100 µg in IFAd.

IFA. Indirect immunofluorescence assays (IFA) using both live and air-dried sporozoites were used to characterize and titrate antibody responses. Briefly, for live-sporozoite IFAs, 40,000 parasites were incubated on ice with different sera dilutions. Sporozoites were then washed 3 times with cold PBS with 1% BSA, suspended in 0.2 ml and placed into the well of a Lab-Tek chambered coverglass (Thermo Scientific Nunc, Rochester, N.Y.). The chamber was then spun at 300×G for 2 min and, after discarding the supernatant, 0.2 ml of PBS with 4% Paraformaldehyde (Sigma, Saint Louis, Mo.) were added. Samples were incubated for 1 h at room temperature, washed 3 times with PBS and incubated with secondary antibody [AlexaFluor 488 F(ab')2 fragment of goat anti-mouse IgG(H+L); 2 mg/ml; Invitrogen] for 30 min. Samples were then washed and green-fluorescent sporozoites were visualized using a Nikon Eclipse 90i fluorescent microscope. IFAs using air-dried sporozoites were performed as previously described [17].

In vitro T cell cytokine assays. Spleen cells from groups of 3 each of (B10×B10.s) F1 mice were harvested and pooled 4-6 weeks after immunization with the various WHcAg hybrid VLPs. Spleen cells ($5\times10^5$) were cultured with varying concentrations of WHcAg, CS or synthetic peptides derived from WHcAg or CS protein. For cytokine assays, culture supernatants were harvested at 48 h for IL-2 determination and at 96 h for interferon-gamma (IFNγ) determination by ELISA. IFNγ production was measured by a two-site ELISA using mAb 170 and a polyclonal goat anti-mouse IFNγ (Genzyme Corp., Boston, Mass.).

Development of *P. berghei* chimeric parasites expressing the C-terminal region of the *P. falciparum* CS protein (Pb/Pf-CSP-CT). The new transgenic strain derived from *P. berghei* ANKA strain expressing the C-terminus of *P. falciparum* was generated using the plasmid pR-CSPfCT, which carries the C-terminal region of the *P. falciparum* CSP. This plasmid was derived from plasmid pIC-CSPfCT, which resulted from the replacement of the *P. berghei* CSP C-terminus with the C-terminal region of the 3D7 strain of *P. falciparum* CSP. Briefly, a 306-bp restriction fragment encompassing base pairs 715 to 1020 of the *P. berghei* CSP gene was excised from a modified version of pIC-CSwt [23] using the restriction enzymes SexAI and PacI and then replaced with a fragment comprising the *P. falciparum* CSP C-terminal region. The *P. falciparum* CSP C-terminus was excised as a 312-bp SexAI-PacI restriction fragment from plasmid pPfCT (Genescript, Piscataway Township, N.J.), synthesized to comprise the *P. falciparum* CSP C-terminal region. Thus, the CSP gene in the resulting plasmid, pIC-CSPPfCT, consists of the *P. berghei* N-terminal and repeat regions (base pairs 1 to 786) and the remainder of the *P. falciparum* CSP (base pairs 787 to 1026). We then excised the hybrid CSP gene from pIC-CSPfCT as a KpnI-XhoI fragment and inserted it into the transfection plasmid, pR-CSPfCT. KpnI and SacI were used to release the inserted fragment from pR-CSPfCT prior to transfection of WT *P. berghei* (ANKA strain) parasites, as previously described [24]. Transgenic parasites were selected in Swiss Webster mice (NCI, Frederick, Md.) by treatment with pyrimethamine (MP Biomedicals, Solon, Ohio) in drinking water (0.07 mg/ml). Pyrimethamine-resistant parasites were then cloned by limiting-dilution.

Successful recombination at the 5' and 3' ends of the locus was verified by PCR. The primers used to confirm 5' integration were 5'-F (TCACCCTCAA GTTGGGTAAA A set forth as SEQ ID NO:51) and PbPfCT-R (GCAGAGCCAG GCTTTATTCT set forth as SEQ ID NO:52); the primers to verify integration at the 3' end were 3'-F (TGTAAAAATG TGTATGTTGT GTGC set forth as SEQ ID NO:53) and 3'-R (GTGCCCATTA CGACTTTGCT set forth as SEQ ID NO:54). To verify that the cloned parasite population did not have contaminating WT *P. berghei* parasites, we developed a PCR assay using primers that flank the SexAI restriction site and then digested the resulting product with this enzyme. This restriction site is not present in the WT *P. berghei* CSP sequence but was inserted by replacement with our synthetic construct. The primers used for this PCR analysis were PbWT NT-F (TGTTA-CAATG AAGGAAATGA TAATAAATTG TAT set forth as SEQ ID NO:55) and Pb 3'UTR-R (TCTTTTGGAC ATAT-ATTCAT TTTAGCA set forth as SEQ ID NO:56). Lastly, DNA isolated from the cloned chimeric parasites was sequenced to confirm the replacement of the *P. berghei* C-terminal region with the *P. falciparum* CSP C-terminus sequence. The sequence of the hybrid CS protein is provided in FIG. 10A.

In vivo protection assays. To measure liver parasite load, C57B1/6 mice were challenged i.v. with 10,000 Pb/Pf or Pb/Pv hybrid sporozoites. Forty-eight hours later livers were harvested to assess the parasite load by RT-PCR as previously described [25]. We assessed sterile protection by monitoring the mice for development of blood-stage parasites after feeding by infected *Anopheles stephensi* mosquitoes. Briefly, prior to challenging mice, the percentage of infected mosquitoes was determined by choosing at least 10 mosquitoes from the pool and examining each salivary gland for the presence of sporozoites. Based on this information, the number of sporozoites used for the challenge was determined. The mice were anesthetized by i.p. injection of 250 µl of 2% avertin prior to feeding Pb/Pf- or Pb/Pv-infected *A. stephensi* mosquitoes for five minutes. After feeding, all mosquitoes were examined for the presence of blood in their gut to determine the number that took a blood meal. Daily blood smears were performed starting at 4 days after challenge. For measuring protection mediated by antibodies, Pb/Pf (described as CS(Pf) in [16]) or Pb/Pv [17] hybrid sporozoites were used for the challenge when VLPs targeting *P. falciparum* and *P. vivax* epitopes, respectively, were used as immunogens. For assessing protective efficacy of T cell epitopes, the new Pb-Pf-CSP-CT hybrid sporozoites described above were used for the challenge.

Results

Immunogenicity of VLPs carrying repeat versus non-repeat CS B cell epitopes. A number of interesting candidate epitopes outside the CS repeat domain have been described. For example, non-repeat CS B cell epitopes which have been shown to elicit in vitro neutralizing antibodies include: aa93-113 (lysine (K)-rich region), aa112-123 (conserved N1), and aa298-315 [26-28]. Similarly, a high percentage of adults and lesser numbers of children living in malaria endemic areas possess antibodies specific for CS C-terminal sequences that represent CD4+ and CD8+ recognition sites for human and murine T cells (i.e., UTC, TH3.R and CS.T3 regions) [29]. For several reasons the consideration of these non-repeat, CS B cell epitopes for vaccine design has been marginalized. Firstly, the immunodominance of the NANP and NVDP repeats and the established neutralizing efficacy of anti-CS repeat antibodies has reduced interest in non-repeat B cell epitopes somewhat [30-32]. Secondly, the induction of high titer CS-specific antibodies to non-repeat epitopes has been difficult with most immunogens. Our WHcAg platform technology allows insertion of virtually any CS sequence onto WHcAg. The resulting immunogens elicit high titer antibody even if the CS sequence is cryptic on the native CS protein. The Pb/Pf sporozoite technology allows evaluation of efficacy of these candidate vaccines by inserting the Pf B and T cell candidate epitopes in the CS protein of Pb sporozoites. The combination of these technologies permitted us to overcome the problems that have prevented analysis of the protective efficacy of CS non-repeat B and T cell sites in the past.

We produced, characterized and examined the immunogenicity of hybrid-WHcAg VLPs carrying the NANP/NVDP repeat epitopes and three selected non-repeat CS-specific B cell epitopes: the N1 region (aa 112-123); the K-rich region (aa 93-113); and the aa 298-315 region (see FIG. 1A-B) in comparison to full length rCS protein. Although the T cell response to CS protein is highly genetically restricted in mice and humans [33,34], we avoided this problem by immunizing a high responder strain (H-2b). Immunization with the full length rCS protein elicited very high antibody production to the 2 repeat epitopes, NANP and NVDP. However, consistent with a cryptic nature of the non-repeat CS B cell epitopes, immunization with rCS protein elicited no antibody to the CS298-315 region, extremely low antibody production to the N1 region (i.e., 1:1000 titer) and relatively low antibody production to the K-rich region (i.e., 1:125,000 titer) after primary and secondary immunization (Table 1). In contrast, both repeat and non-repeat B cell regions "excised" from the CS protein and inserted onto hybrid WHcAg VLPs elicited high levels of anti-insert antibodies (i.e., at least $1:3\times10^6$ titers) (Table 1). Furthermore, the repeat and non-repeat anti-insert antibodies bound rCS protein in ELISAs. The repeat and non-repeat anti-insert antibodies also bound dry, hybrid Pb/Pf sporozoites to varying degrees as demonstrated by immunofluorescence assays (IFA) (Table 1). Interestingly, only the repeat-specific anti-insert antibodies (i.e., NANP/NVDP-specific) bound live sporozoites. These observations suggest that the three non-repeat B cell epitopes on the CS protein may be cryptic on intact, viable sporozoites.

described above. As shown in FIG. 2, immunization (2 doses of 20 and 10 μg) with VLPs carrying the repeat B cell epitopes protected mice challenged with 10,000 Pb/Pf sporozoites at a level of 98% in terms of parasite 18S rRNA copies detected in liver compared to mice immunized with a control hybrid WHcAg VLP carrying an irrelevant insert from the hepatitis B virus (HBV). In contrast, immunization (3 doses of 20, 10, and 10 μg) with the hybrid WHcAg VLPs carrying each of the three non-repeat B cell epitopes provided little to no protection (0-44%) against Pb/Pf sporozoite challenge despite the fact that high levels of anti-insert antibodies were present in the immunized mice (FIG. 2, Table 1). These results suggest that the non-repeat B cell epitopes may be cryptic on viable sporozoites in vivo. The results also suggest that it may not be productive to include these three non-repeat B cell epitopes in a CS-VLP vaccine candidate. A caveat to this interpretation is that the non-repeat B cell epitopes in the context of the VLPs may not represent the epitope structures present within the native CS protein, although anti-non-repeat Abs do bind rCS and dry sporozoites. Ab exception may be the non-CS repeat epitope recognized by mAb 5D5.

Confirmation that CS repeat antibodies are predominant in providing protection. As an alternate approach to addressing the question of the importance of repeat vs. non-repeat CS-specific antibodies, we performed an experiment using rCS as the immunogen rather than hybrid VLPs. Mice were immunized with 2 doses of rCS (20 μg/10 μg) and the resulting antisera were pooled and pre-incubated with the 10,000 Pb/Pf sporozoites used for the challenge. This antisera provided significant protection compared to sporozoites pre-incubated in normal mouse sera (NMS). However, if the anti-rCS antisera was pre-adsorbed with repeat-containing

TABLE 1-1

Endpoint Dilution Titers of WHc-CS VLPs carrying B cell epitopes.

| CS (Insert) | anti-WHc | anti-NANP | anti-NVDP | anti-N1 | anti-K rich | anti-CS (298-315) | anti-CSP | IFA dry hybrid | IFA viable hybrid | ↓ Liver Stage |
|---|---|---|---|---|---|---|---|---|---|---|
| NANP/NVDP | $6 \times 10^6$ | $>10^7$ | $6 \times 10^6$ | — | — | — | $>10^7$ | 16,000 | ++ >300 | 98% |
| N1 (112-123) | $3 \times 10^6$ | — | — | $3 \times 10^6$ | — | — | $6 \times 10^6$ | 1,800 | — | 18% |
| K rich (93-113) | 625,000 | — | — | — | $3 \times 10^6$ | — | $6 \times 10^6$ | 600 | — | 0% |
| CS (298-315) | $6 \times 10^6$ | — | — | — | — | $3 \times 10^6$ | $>10^7$ | 16,000 | — | 44% |
| CSP Full | 0 | $6 \times 10^6$ | 625,000 | 1,000 | 125,000 | 0 | $6 \times 10^6$ | ND | ND | ND |

↓ Reduction in liver parasite load.

In Table 1-1, the listed WHcAg hybrid VLPs and full length rCS protein were used to immunize mice (2 doses; 20 μg and 10 μg in IFAd). Secondary antisera were pooled, serially diluted and analyzed by ELISA for binding to: solid phase WHcAg; repeat peptides (NANP)$_5$ (SEQ ID NO:90) and (DPNANPNV)$_2$ (SEQ ID NO:91); non-repeat peptides N1, Krich, CSP298-315; and rCS. Antisera were also evaluated by IFA on dry or viable sporozoites. The protective efficiency after in vivo challenge with 10,000 Pb/Pf sporozoites of mice immunized with the listed WHc-CS VLPs is also shown.

Figure 8:
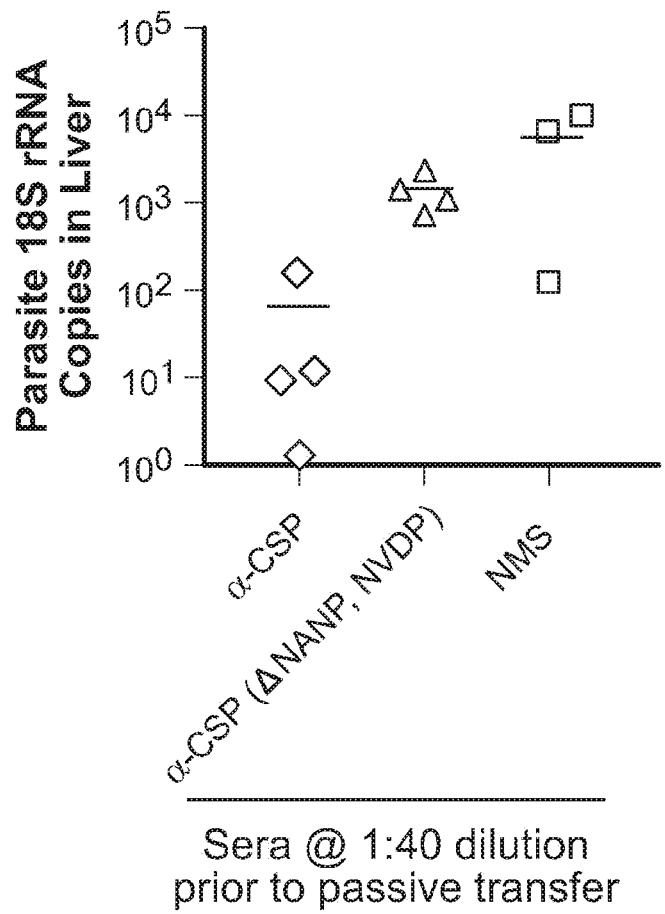
FIG. 8 shows that anti-CS repeat antibodies protect against a sporozoite challenge. Mice were immunized with rCS and sera either unadsorbed or adsorbed with NANP/NVDP-containing VLPs (ANANP, NVDP) were incubated with 10,000 sporozoites prior to challenge. NMS, normal mouse sera.

Protective efficacy of VLPs carrying repeat versus non-repeat CS B cell epitopes. We also performed immunization/challenge experiments to determine the protective efficacy of hybrid WHcAg VLPs carrying the 2 repeat B cell epitopes (NANP/NVDP) and the three non-repeat B cell epitopes VLPs (Δ NANP, NVDP) prior to being added to the 10,000 sporozoites, the protective efficacy was largely lost (FIG. 8).

Figure 3A:
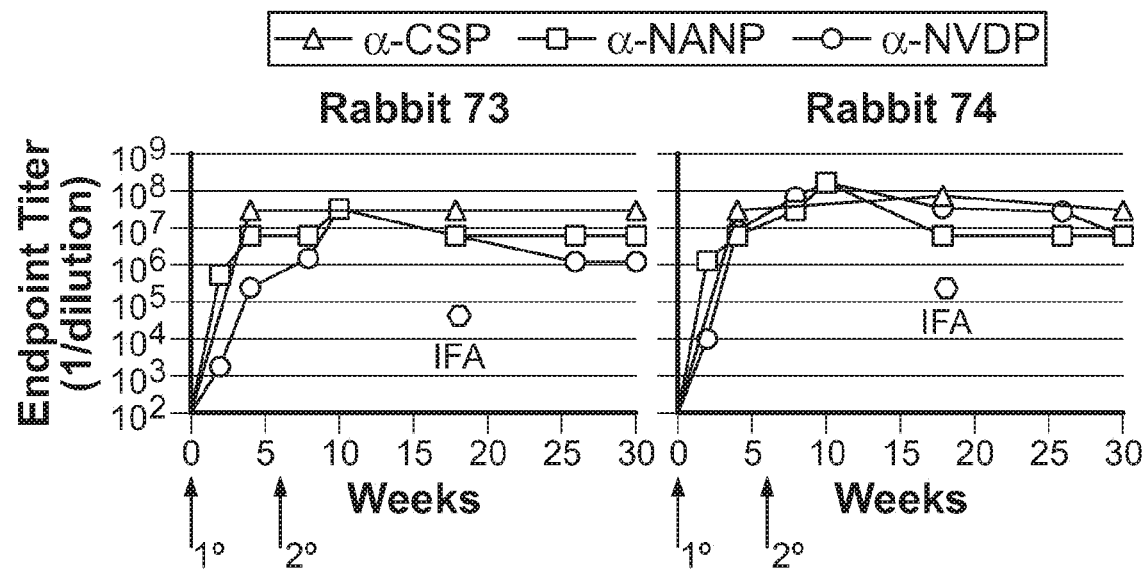
FIG. 3A-C shows immunogenicity of WHc-Mal-78-UTC in rabbits and protective efficacy of anti-VLP sera In FIG. 3A animals were primed with 200 µg of WHc-Mal-78-UTC emulsified in IFAd and boosted at week 6 with 100 µg emulsified in IFAd (rabbit 73) or 200 µg in saline (rabbit 74). Serum was collected at the indicated time points and endpoint titers against NANP, NVDP and rCSP determined by ELISA. The sporozoite-specific IFA assay was performed on 18 week antisera and is represented by a star-shaped point.
Figure 3B:
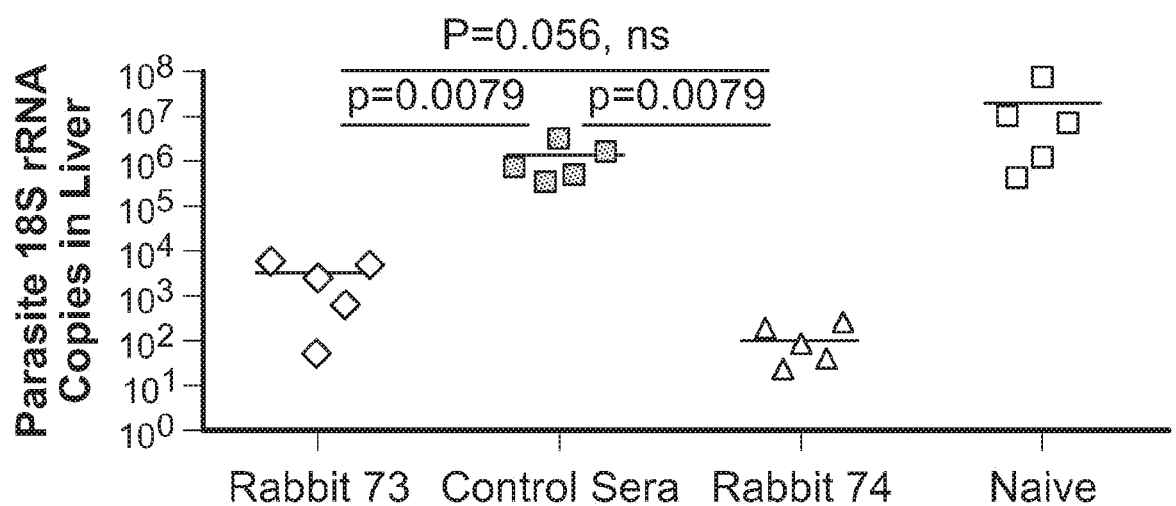
Figure 3C:
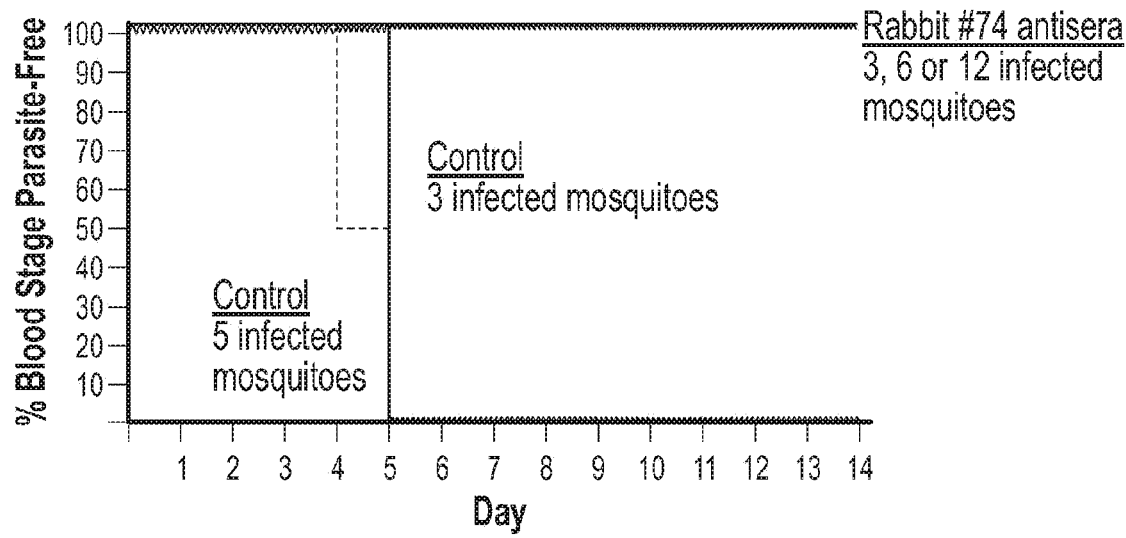

WHc-Mal-78-UTC elicits protective Abs in rabbits. To examine protective efficacy of antisera from a second species, two rabbits were immunized with a VLP carrying the 2 CS repeat B cell epitopes and a malaria-specific human T cell epitope (UTC), designated WHc-Mal-78-UTC (FIG. 3A). The antisera were passively transferred into naïve murine recipients. The recipients of anti-VLP rabbit sera were either challenged intravenously (i.v.) with 10,000 Pb/Pf sporozoites and parasite burden in the liver determined (FIG. 3B) or challenged by the bites of infected mosquitoes and blood-stage parasitemia monitored over a 10-14 day period (FIG. 3C). Both rabbits (#73 and #74) produced high titer anti-NANP, anti-NVDP and anti-rCS Abs detected by ELISA and by IFA on hybrid sporozoites (FIG. 3A). Antisera (0.5 ml) from both rabbits were passively transferred (i.v.) to naïve mice and the mice were immediately challenged with 10,000 Pb/Pf sporozoites (i.v.). Forty hours later the parasite liver burdens were determined. Passively transferred anti-VLP sera from both rabbits significantly reduced the parasite liver burden as compared to control rabbit sera, although rabbit #74 sera was most effective (FIG. 3B). It is notable that rabbit #74 was primed with WHc-Mal-78-UTC emulsified in IFAd but boosted with the VLP in saline, whereas, rabbit #73 was primed and boosted in IFAd. This suggests that there may be no advantage to the use of potent adjuvants after the primary injection of the VLPs. Rabbit #74 serum was chosen to passively transfer (0.2 ml) to murine recipients, which were challenged with the bites of from 3 to 12 Pb/Pf-infected mosquitoes over a five minute time frame. Blood stage parasitemia was monitored for the next 10-14 days. All 21 mice receiving the anti-WHc-Mal-78-UTC rabbit sera were totally protected from blood stage parasitemia regardless of exposure to 3, 6 or 12 infected mosquitoes. The 8 control mice exposed to 3 or 6 infected mosquitoes demonstrated infection by day 4 or 5 (FIG. 3C). However, it is interesting to note that the adoptive transfer of 0.2 ml of a 1:3 dilution of rabbit #74 sera failed to protect mice against blood stage infection. These studies demonstrate that the protective efficacy elicited by WHc-Mal-78-UTC VLPs can be mediated solely by anti-CS repeat Abs, but a threshold level of protective Abs is required.

Figure 4:
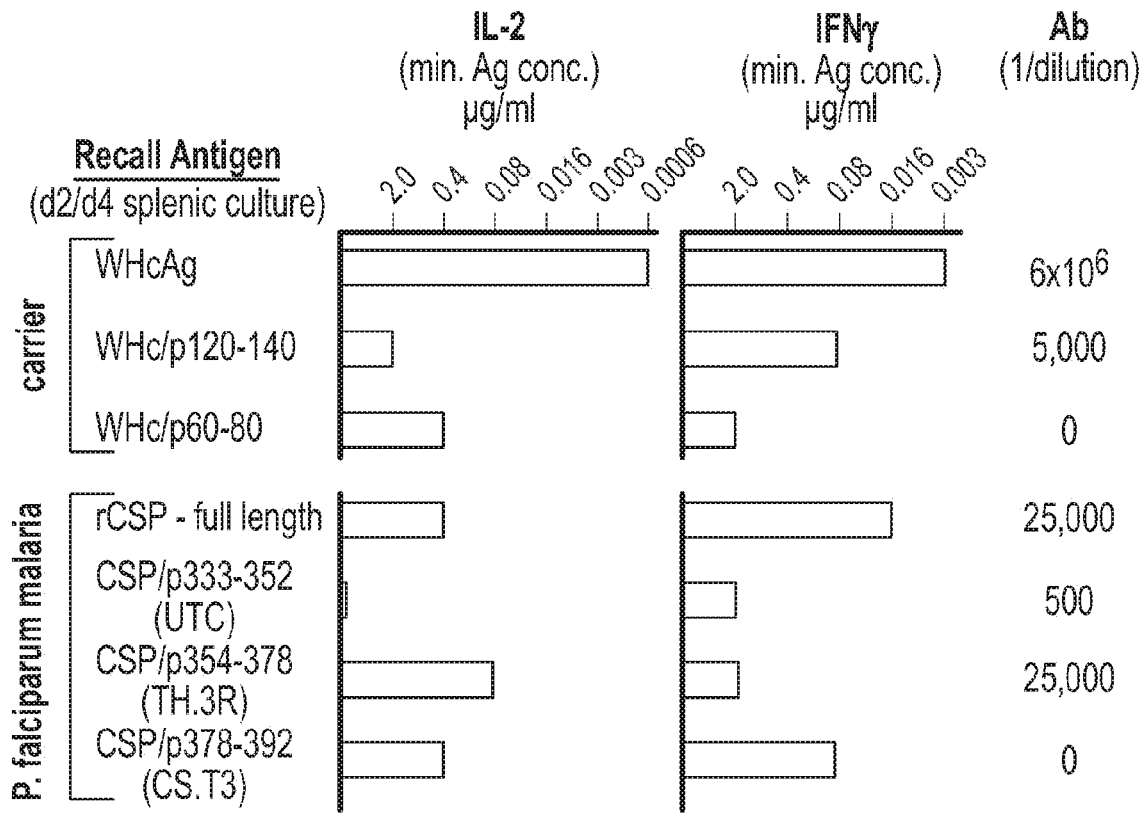
FIG. 4 shows that WHc-Ct-3T primes malaria-specific as well as WHcAg-specific CD4+ T cells. To assess T cell priming, three mice were immunized with WHc-Ct-3T (a single 20 µg dose in IFAd) and 10 days later spleen cells were harvested and cultured as pools with varying concentrations of the indicated recall antigens. Culture supernatants were collected at day 2 for determination of IL-2 and day 4 for determination of IFNγ. The minimum concentration of each antigen necessary to yield detectable cytokine is shown. For antibody production, mice were immunized (20 µg/IFAd) and boosted (10 µg/IFAd).
Figure 9:
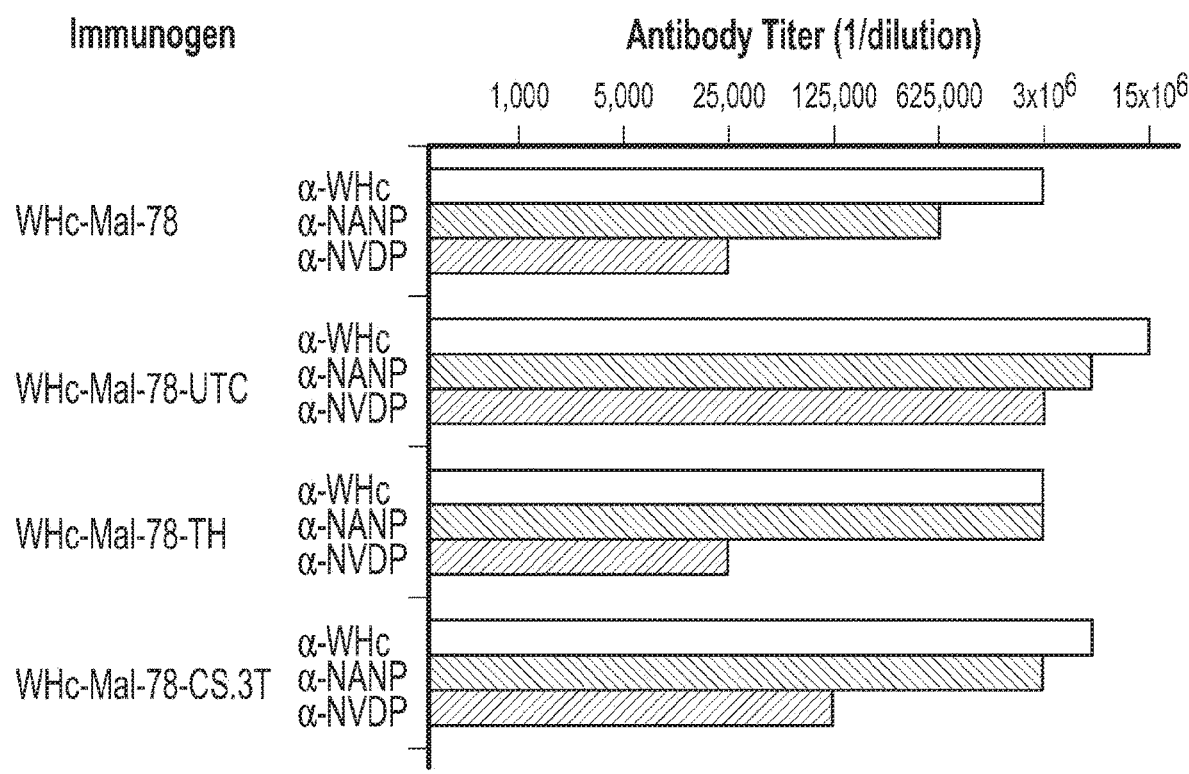
FIG. 9 is a comparison of WHc-CS VLPs containing malaria-specific T cell epitopes. Groups of 3 mice were immunized (2 doses: 20 µg and 10 µg in IFAd) with the indicated WHcAg hybrid VLPs. Secondary antisera were pooled and serially diluted and analyzed by ELISA for binding to solid-phase WHcAg, NANP and NVDP. Endpoint titers of pooled sera are shown.

Addition of CS-specific T cell domains. An important goal is to add CS-specific T cell sites to vaccine candidates in order to prime CS-specific CD4+/CD8+ T cells as well as elicit CS-specific neutralizing antibodies. For this purpose, we added 1, 2 or all 3 (i.e., UTC, TH.3R, and CS.T3) well characterized human T cell domains to a standard hybrid WHcAg VLP carrying the 2 CS specific repeats (i.e. WHc-Mal-78). The T cell domains were added to the C-terminus of the hybrid WHcAg VLPs and all 3 hybrid VLPs were successfully produced and were shown to be approximately equally immunogenic in terms of anti-NANP and anti-NVDP antibody production (FIG. 9). In order to determine the contribution of CS-specific T cells to the protective efficacy of candidate VLP vaccines, the established protective efficacy of anti-NANP/NVDP antibodies had to be excluded. For that purpose, we constructed a hybrid WHcAg VLP carrying only the 3 T cell regions and devoid of the neutralizing CS repeat B cell epitopes designated WHc-Ct-3T. As shown in FIG. 4, immunization with WHc-Ct-3T primed both WHcAg-specific and CS protein-specific CD4+ T cells as determined by cytokine production elicited by splenic T cells cultured with a panel of WHcAg and CS protein-specific proteins and peptides. Also note that WHc-Ct-3T immunization elicited low level Ab production to rCS and the TH.3R site, which is also a B cell epitope in addition to a CD4+ T cell epitope. Because the Pb/Pf hybrid sporozoites used in the previous studies do not contain the P. falciparum T cell domains, a new transgenic Pb sporozoite (Pb/Pf-CSP-CT) containing the complete C-terminus (i.e., aa318-397) from the Pf CS protein was produced (FIG. 1A). Therefore, we were able to perform an immunization/challenge experiment with WHc-Ct-3T VLPs. Although WHc-Ct-3T was immunogenic for both CS-specific B and CD4+ T cell epitopes (FIG. 4), no protection against a 10,000 Pb/Pf-CSP-CT sporozoite challenge was elicited.

Figure 5A:
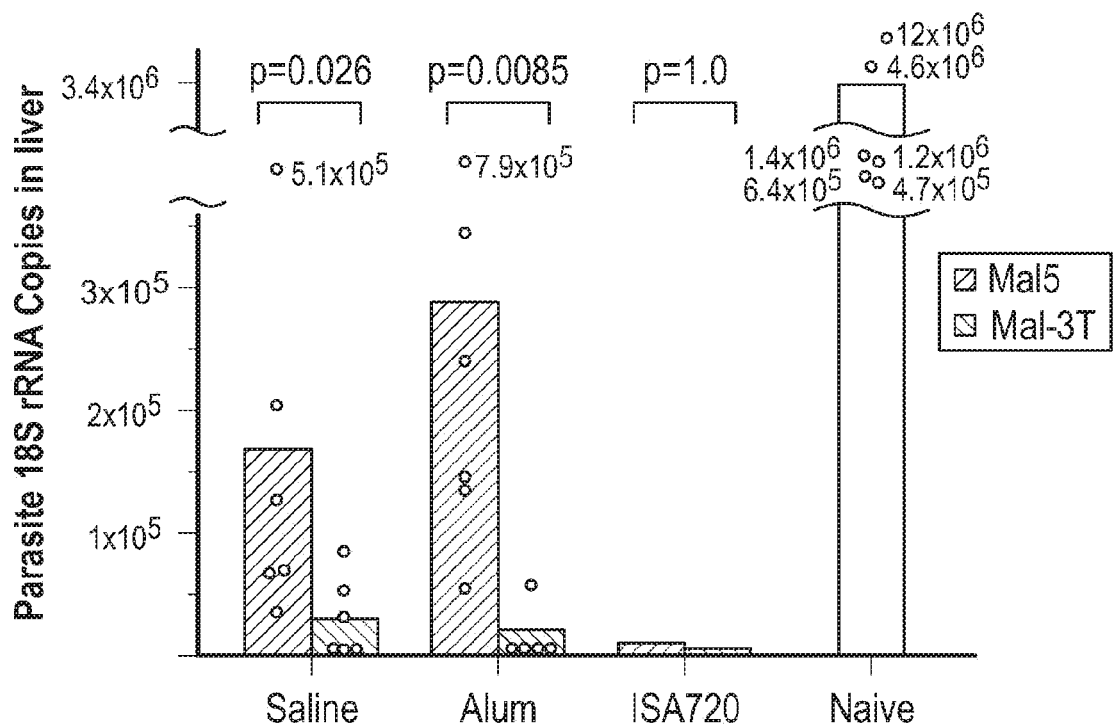
FIG. 5A-B is a comparison of protective efficacy and serology for WHc-Mal5-78 (Mal5) vs WHc-Mal-78-3T (Mal-3T). Groups of 6 mice each were immunized with WHc-Mal5-78 or WHc-Mal-78-3T formulated in either saline, alum or Montanide ISA-720 and given a single booster injection. After the boost mice were challenged with 10,000 hybrid sporozoites.
Figure 5B:
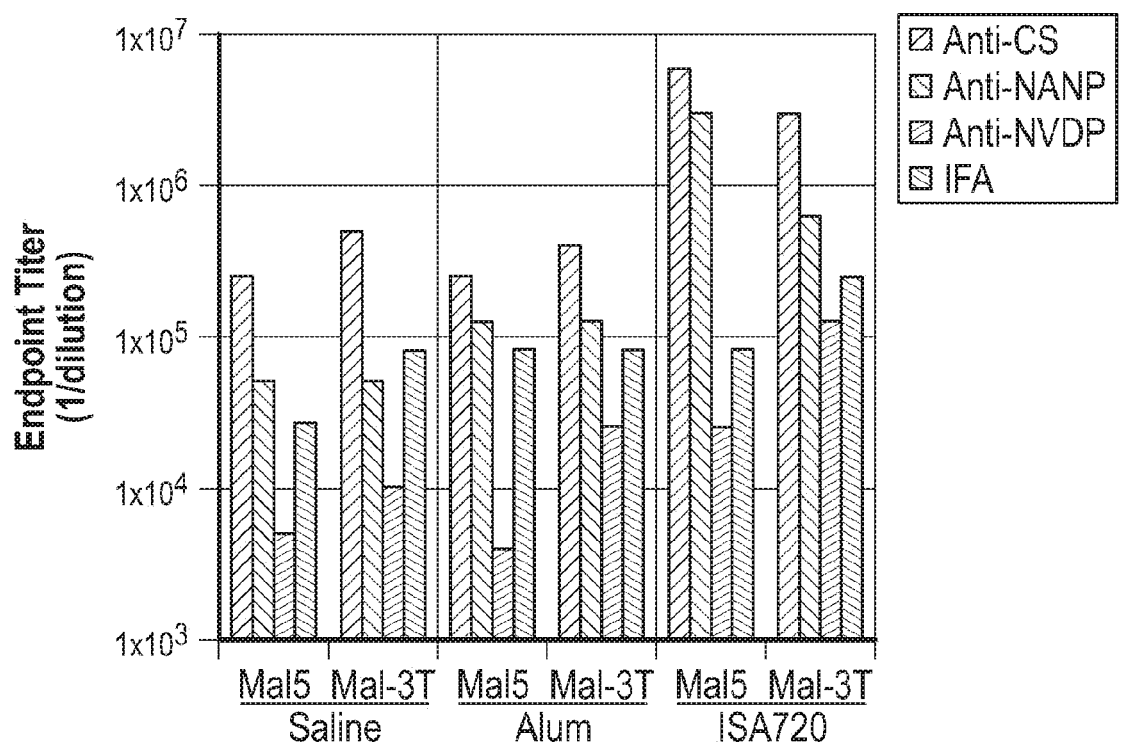

Effect of the 3 CS-specific T cell domains on protective efficacy. Because anti-NANP-specific Abs play a dominant role in protection, we compared the protective efficacy of a standard VLP (WHc-Mal5-78) containing only (NANP)$_4$ (SEQ ID NO:92), which was previously shown to elicit significant protection against a Pb/Pf sporozoite challenge, with a VLP containing the NANPNVDP(NANP)$_3$ (SEQ ID NO:19) B cell insert in the loop of WHcAg plus all 3 T cell domains (WHc-Mal-78-3T) inserted at the C-terminus of WHcAg. Groups of 6 mice were primed and boosted with WHc-Mal5-78 or WHc-Mal-78-3T formulated either in saline only (200 µg VLPs), alum (100 µg VLPs) or Montanide ISA720 (50 µg VLPs). Both VLPs elicited significant reduction in parasite liver burden (at least 90% reduction in parasite 18S rRNA copies in liver) in all three formulations compared to naïve challenged control mice (FIG. 5A). However, the VLP carrying the three T cell domains (WHc-Mal-78-3T) elicited statistically superior protection in saline (99.1% vs 95% protection) and in alum (99.2% vs 91.7% protection) compared to the (NANP)$_4$ (SEQ ID NO:92) B cell insert only-containing VLP (WHc-Mal5-78). Both VLPs were equally protective when formulated in Montanide ISA720 (FIG. 5A). Anti-CS, anti-NANP, and anti-NVDP antibodies were measured by ELISA and IFAs were performed to determine if differential antibody levels would explain the superior protective efficacy of the WHc-Mal-78-3T VLP formulated in saline and alum (FIG. 5B). No significant serological differences were noted between the two VLPs. However, there was a trend towards higher titer anti-NVDP repeat antibodies in the WHc-Mal-78-3T-immunized groups, especially when formulated in alum. This was expected because the WHc-Mal5 VLP does not contain the NVDP repeat. However, the polyclonal anti-NANP antibodies elicited by the WHc-Mal5 VLP demonstrated cross-reactivity for the (NVDP)$_2$ (SEQ ID NO:93) peptide. IgG isotype testing also revealed no significant differences between anti-CS antibodies elicited by WHc-Mal5 and WHc-Mal-78-3T VLPs. This suggests that malaria-specific CD4+ T cells primed by immunization with the WHc-Mal-78-3T VLP may have contributed to the greater efficacy either indirectly by providing an additional source of T helper cell function or, more likely, by directly exerting a negative effect on liver stage development via cytokine production. Although the hybrid sporozoites used for challenge did not contain the Pf T cell domains engineered into the WHc-Mal-78-3T VLPs, the 3 T cell domains of P. falciparum and P. berghei share a significant degree of homology as shown in FIG. 10B. In any event, the superior performance of the WHc-Mal-78-3T VLP elevated this VLP to a primary vaccine candidate.

A WHcAg-CS VLP in alum elicits sterile immunity to blood stage malaria. WHc-Mal-78-3T performed well in terms of reducing parasite load in the liver after a 10,000 Pb/Pf sporozoite challenge (up to 99.98% reduction, FIG. 5B), however, to determine if this level of reduction in liver burden is sufficient to yield full protection from blood stage parasitemia an immunization/challenge experiment monitoring blood stage parasitemia as the final endpoint is required because a single surviving sporozoite infecting the liver can result in a blood stage infection [35]. For this experiment we modified WHc-Mal-78-3T by a point mutation (C61S) in the WHcAg, which eliminated the intermolecular disulfide bond at residue 61. The C61S mutation in WHcAg-hybrid VLPs was chosen because it can reduce anti-WHc (carrier-specific) antibody production and/or increase anti-insert antibody production.

Groups of 10 mice each were immunized and boosted with 100 µg of the WHc(C61S)-Mal-78-3T VLP either formulated in alum, alum+QS-21, or primed with an emulsion of Montanide ISA 720 (50%) and boosted in alum. The control group was primed with 100 µg of WHcAg (no insert) emulsified in Montanide ISA 720 and boosted in alum (FIG. 6A). Six weeks after the boost mice were challenged by exposure to the bites of 12 Pb/Pf-infected mosquitoes for 5 minutes. This method of challenge was chosen because it represents a more physiologically relevant route of infection as compared to i.v. injection of sporozoites. Blood was sampled over the next 14 days and examined for parasitemia (FIG. 6B). As shown in FIG. 6C, 10 of 10 WHcAg-immunized control mice became positive for blood stage malaria within a mean of 4.4 days. In contrast, 0 of 9 mice immunized with WHc(C61S)-Mal-78-3T formulated in alum+QS-21 became infected; 1 of 10 mice immunized in Montanide/alum became infected; and 2 of 10 mice immunized in alum became infected. The 3 of 29 mice in the experimental groups that did become infected demonstrated delayed parasitemia (mean of 6.0 days), suggesting a possible elimination of 99% of sporozoites given that 90% elimination is required to obtain a one day delay in developing a patent blood stage infection. The serology of each group pre-challenge and of the survivors three months post-challenge is shown in Table 2. Although anti-CS Ab titers decreased over time, anti-CS Abs were still in excess of $1\times10^6$ endpoint titers three months post-challenge in all adjuvant groups. The apparent lack of a boost to the anti-CS Ab titers may reflect the low immunogenicity of the protein in the context of the parasite infection.

zoites (Table 3). Immunization with 100 µg of WHc-Pv-78 in IFAd elicited extremely high titer anti-CS Pv repeat antibodies ($1.5\times10^8$). This immunization schedule was chosen to examine the protective efficacy of WHc-Pv-78 VLPs against experimental liver infection as well as blood stage infection with hybrid Pb/Pv sporozoites in mice. As shown in FIG. 7A, immunization with WHc-Pv-78 VLPs provided 99% protection in terms of parasite 18S rRNA copies detected in the liver compared to mice immunized with the WHcAg carrier after challenge with 10,000 Pb/Pv sporozoites. To determine if this level of reduction in liver parasite burden was sufficient to provide sterile immunity to blood stage infection, WHc-Pv-78 VLP-immunized and WHcAg-immunized mice were challenged by exposure to the bites of 10 Pb/Pv-infected mosquitoes for 5 minutes. Whereas 4 of 5 control mice became infected in a pre-patent period of 4.5 days, 0 of 4 WHc-Pv-78-immunized mice were infected over an observation period of 14 days (FIG. 7B). Given these positive protective efficacy results with VLP-206 and the sequence similarity of the VK-210 and VK-247 CS repeat sequences, the insertion of the VK-247 CS repeat sequence (SEQ ID NO:70) onto the WHcAg carrier is expected to elicit protective antibodies against the VK-247 strain of P. vivax. Immunization of subjects with an antigenic composition comprising a VLP with both CS repeats of a VK-210 strain and CS repeats of a VK-247 strain will increase the diversity of protective antibodies against P. vivax. Similarly, immunization of subjects with an antigenic composition comprising a first VLP with CS repeats of a VK-210 strain, and second VLP with CS repeats of a VK-247 strain, will also result in a broadly reactive antibody response against P. vivax.

TABLE 1-2

Kinetics of IgG Ab titers through primary immunization (1°) with WHc(C61S)-Mal-78-3T, at the boost (2°) and at 3 months post-challenge.

| Immunogen | Formulation | | Endpoint Titer (1/dilution) | | | |
|---|---|---|---|---|---|---|
| | | | α-rCSP | α-NANP | α-NVDP | α-WHc |
| WHc(C61S)-Mal-78-3T | Alum | 1° | 82.5K | 43K | 5.5K | 125K |
| | Alum | 2° | $4.7 \times 10^6$ | $4 \times 10^6$ | 900K | $3.5 \times 10^6$ |
| | | 3 mo post-challenge | $2.2 \times 10^6$ | $1.6 \times 10^6$ | 540K | 875K |
| WHc(C61S)-Mal-78-3T | Alum + QS-21 | 1° | 103K | 68K | 13.5K | 125K |
| | Alum + QS-21 | 2° | $4.5 \times 10^6$ | $4.8 \times 10^6$ | $1.5 \times 10^6$ | $3 \times 10^6$ |
| | | 3 mo post-challenge | $1.25 \times 10^6$ | 925K | 242K | $1.7 \times 10^6$ |
| WHc(C61S)-Mal-78-3T | ISA-720 | 1° | 183K | 113K | 17.8K | 475K |
| | Alum | 2° | $4.3 \times 10^6$ | $4.3 \times 10^6$ | $1.3 \times 10^6$ | $2.6 \times 10^6$ |
| | | 3 mo post-challenge | $1.25 \times 10^6$ | $1.1 \times 10^6$ | 160K | 708K |
| WHcAg | ISA-720 | 1° | 0 | 0 | 0 | 625K |
| | Alum | 2° | 0 | 0 | 0 | $11.7 \times 10^6$ |
| | | 3 mo post-challenge | na | na | na | na |

Mean endpoint dilution titers from 9-10 mice in each group are shown.

Preliminary evaluation of a VLP carrying P. vivax CS epitopes. A hybrid WHcAg VLP carrying 2 copies each of both variants of type 1 (VK210) CS repeat epitopes from P. vivax parasites (SEQ ID NO:69) was constructed (WHc-Pv-78, also referred to as VLP-206). In vivo protective efficacy was evaluated using hybrid P. berghei/P. vivax (Pb/Pv) sporozoites expressing the repeat region of the P. vivax CS protein (both VK210 variants) [17]. Immunization with 2 doses of varying amounts of WHc-Pv-78 VLPs in either incomplete Freund's adjuvant (IFAd) or alum elicited high titer anti-CS PV repeat antibodies as detected on solid phase peptide and verified by IFA assay on Pb/Pv hybrid sporo-

TABLE 1-3

Immunogenicity of WHc-Pv-78 VLPs.

| Immunogen | Adjuvant | Dose | 1°/2° | Antibody Titer (1/dilution) | | |
|---|---|---|---|---|---|---|
| | | | | α-WHc | α-Pv1a | IFA |
| WHc-Pv-78 n = 9 | Alum | 100 µg | 1° | 80.5K | 24.5K | — |
| | | 100 µg | 2° | $9.5 \times 10^6$ | $2.2 \times 10^6$ | 8.1K |
| WHc-Pv-78 n = 3 | IFAd | 20 µg | 1° | 250K | 250K | — |
| | | 10 µg | 2° | $3 \times 10^6$ | $3 \times 10^6$ | — |
| WHc-Pv-78 | IFAd | 100 µg | 1° | $3 \times 10^6$ | $9 \times 10^6$ | — |

TABLE 1-3-continued

Immunogenicity of WHc-Pv-78 VLPs.

| Immunogen | Adjuvant | Dose | 1°/2° | Antibody Titer (1/dilution) | | |
|---|---|---|---|---|---|---|
| | | | | α-WHc | α-Pv1a | IFA |
| n = 8 | | 100 µg | 2° | $6.5 \times 10^7$ | $1.5 \times 10^8$ | 72.9K |
| WHcAg | IFAd | 100 µg | 1° | $6 \times 10^6$ | 0 | — |
| n = 10 | | 100 µg | 2° | $2.3 \times 10^8$ | 0 | 0 |
| Mab 2F2 (mg/ml) | — | — | — | 0 | $45 \times 10^6$ | — |

Mean endpoint dilution Ab titers shown. 1°, primary; 2°, secondary antisera. IFA assay used Pb/Pv dry sporozoites.

Discussion

An epitope-focused approach was utilized to present selected epitopes from the CS protein of the *P. falciparum* and *P. vivax* malaria parasites on the WHcAg carrier platform. Two repeat and three non-repeat B cell epitopes from the *P. falciparum* CS protein were inserted into the WHcAg carrier. Although all hybrid VLPs elicited high levels of anti-insert Abs, only hybrid VLPs carrying the CS repeat B cell epitopes (NANP and NVDP) provided significant protection of the liver (98%) against an experimental challenge with hybrid Pb/Pf sporozoites in mice. Whereas, anti-CS repeat and anti-CS non-repeat Abs bound dry Pb/Pf sporozoites, only anti-CS repeat Abs bound viable sporozoites. This data suggests that the three non-repeat B cell epitopes are poorly expressed or cryptic on viable sporozoites. Addition of three well-defined malaria-specific human T cell domains to the hybrid VLPs enhanced protective efficacy in the liver as well as primed malaria-specific CD4+ T cell cytokine production. However, immunization with hybrid VLPs carrying only the three malaria-specific T cell domains was unable to provide protection, indicating that anti-CS repeat Abs are necessary for protection. In fact, anti-CS repeat Abs are sufficient for protection against liver stage as well as blood stage infection as demonstrated by sterile immunity to blood stage infection following adoptive transfer of rabbit anti-VLP antiserum. Furthermore, active immunization with a hybrid VLP, designated WHc(C61S)-Mal-78-3T (VLP-162), elicited sterile immunity to blood stage infection in 26 of 29 mice and delayed parasitemia in the remaining three mice, depending on adjuvant formulation. The alum+QS-21 formulation was the most efficient adjuvant and yielded 100% protection from blood stage infection. The results indicate that immunization with an epitope-focused VLP containing selected B and T cell epitopes from the *P. falciparum* CS protein formulated in adjuvants acceptable for human use can elicit sterile immunity against blood stage malaria if sufficient anti-CS protective Abs are produced.

In this current study we developed a species variant of the HBcAg, the WHcAg, as a platform for *P. falciparum/P. vivax* CS epitopes in order to avoid the disadvantages of using a carrier derived from a human pathogen [36-38]. This is especially important for a malaria vaccine because HBV and malaria are co-endemic in many regions of the world and chronic HBV carriers are often immune tolerant to both HBcAg and HBsAg (note that the HBsAg is used as a carrier in the RTS,S vaccine). Additional modifications to the WHc(C61S)-Mal-78.3T vaccine candidate compared to ICC1132 are: the use of the full length WHcAg to accommodate the encapsidation of ssRNA as a TLR7 ligand, which enhances immunogenicity [39]; incorporation of additional malaria-specific T cell domains; and mutation of the WHcAg cysteine 61, which eliminates intermolecular disulfide bonds common to both WHcAg and HBcAg. The C61S mutation in hybrid VLPs can reduce anti-WHc (carrier-specific) Ab production and/or increase anti-insert Ab production. For these reasons the WHcAg is a superior choice to the HBcAg as a VLP platform for malaria CS epitopes. FIG. 12 provides a comparison of WHc(C61S)-Mal-78-3T (VLP-162) with ICC.1132.

A number of CS-based vaccines have been developed recently [40-43]. Typically, protective efficacy has been determined using different challenge methods and different chimeric rodent parasites, making comparisons difficult. For example, hybrid Pb/Pf parasites used herein express an extended CS repeat region from the Pf CS protein [16], whereas, other hybrid Pb/Pf parasites used for challenge experiments [40,42] contain the full-length Pf CS protein [44].

In the absence of head-to-head comparative studies to date, the WHc(C61S)-Mal-78-3T candidate embodies a number of unique characteristics that may be advantageous in comparison to other CS-vaccine candidates. The enhanced immunogenicity and protective efficacy of WHc(C61S)-Mal-78-3T suggests that the suboptimal performance of a preerythrocytic vaccine candidate is not likely due to the selection of the CS repeat region as a target or to a paucity of B cell epitopes, but rather to insufficient production of protective Abs. For example, the RTS,S vaccine shares similar CS-specific B and T cell epitopes with WHc(C61S)-Mal-78-3T but the carrier moieties are markedly different. WHc(C61S)-Mal-78-3T efficiently self-assembles into hybrid VLPs, which are stable even at 65° C., whereas the HBsAg-based RTS,S requires the addition of excess native HBsAg particles. Compared to the HBsAg, hepadnavirus nucleocapsids are inherently more immunogenic in mice and humans during natural infection or after immunization [45-48], are less susceptible to MHC restricted non-responsiveness and can function as T cell-independent immunogens [45,48]. Finally, use of the WHcAg would circumvent HBV-specific immune tolerance present in populations endemic for HBV that are often endemic for malaria as well [38]. As a practical matter, WHcAg-CS VLPs are produced in high yields in bacteria and are extremely heat stable, therefore, production costs are relatively low and no cold-chain is required. FIG. 12 provides a comparison of WHc(C61S)-Mal-78-3T (VLP-162) with RTS,S.

Example 2

Hybrid Woodchuck Hepadna Virus Core Antigens Containing a Malaria Non-Repeat CS Protein Epitope The basic structure of the malaria circumsporozoite (CS) protein consists of an immunodominant, central repeat domain flanked by a highly charged N-terminal portion that binds heparin sulfate proteoglycans, contains a conserved proteolytic cleavage site and a C-terminal flanking region containing a type I thrombospodin repeat motif (Plassmeyer et al., J Biol Chem, 284:26951-26963, 2009). Recently mAb 5D5 was found to bind an epitope located in the N-terminal region of the CS protein (Esoinosa et al., J Infect Dis, 212:1111-1119, 2015). mAb 5D5 has several noteworthy characteristics. It binds an epitope mapped to CS(81-91), which is highly conserved. mAb 5D5 binds to live sporozoites and inhibits proteolytic processing at the N-terminus of the CS protein. Passive transfer of mAb 5D5 produces a 1-2 log reduction in parasite load within the liver after challenge with Pb-Pf sporozoites, which is equivalent to the standard, CS repeat-specific mAb 2A10. Importantly, combining mAb 5D5 and mAb 2A10 results in enhanced protection compared to either mAb alone.

Given these impressive characteristics, we endeavored to develop a VLP capable of eliciting a 5D5-like antibody response. Previously, the N-terminal region has been described as immunologically inert, cryptic and inaccessible due to reversible conformational changes that mask some epitopes until the sporozoite interacts with the hepatocyte membrane. We addressed the problem of accessibility of the 5D5 epitope by presenting it on the exposed loop or N-terminus of the WHcAg. Unless otherwise noted, materials and methods as described in Example 1 were employed in Example 2. Interestingly, inserting CS(81-91) on VLPs was immunogenic, but the fine specificity of the Abs produced differed from that of 5D5.

We produced 10 VLPs carrying various lengths of the mAb 5D5 epitope from 72-94, 81-91, to 81-97, inserted at various positions in the WHcAg (78, 81, N-Terminus) (see Table 2-1). mAb 5D5 bound all 10 solid phase VLPs to varying degrees (Table 2-1 column a). The VLPs were relatively immunogenic and raised anti-CS Ab with end point titers between 1:125,000-1:3×10$^6$ after 2 doses (Table 2-1 column b). The anti-VLP Abs inhibited mAb 5D5 binding of CS (Table 2-1 column c). All anti-VLP Abs recognized sporozoites in immunofluorescence assays (IFA) (Table 2-1 column d). However, when the anti-VLP antisera were tested for protective efficacy by adoptive transfer into mice challenged with Pb/Pf transgenic sporozoites, protection of the liver from infection varied from 0-65% reduction in parasite load in the liver (Table 2-1 column e). VLP-245 elicited the greatest protective efficacy (i.e., 65% reduction in liver parasite load. Therefore, three additional VLPs consisting of variants of VLP-245 were produced bearing CS residues 82-91 with one, two, or four glycine substitutions for K85, K85/P89, and K85/L86/K88/P89, respectively (SEQ ID NOs:62-64). The glycines substituted for non-essential, non-contact residues of the 5D5 Mab epitope. These epitope-modified hybrid, WHcAg-hAg VLPs are expected to elicit a polyclonal antibody response with greater protective efficacy than the corresponding hybrid, WHcAg-hAg VLPs lacking epitope modifications. Those VLPs capable of eliciting sera resulting in 50% or greater reduction in parasite load in the liver upon adoptive transfer are suitable for use in preferred antigenic compositions and vaccines of the present disclosure. Similarly, VLPs comprising the insert amino acid sequence and position combination of the exemplary VLPs having a desirable level of liver protective efficacy are suitable for use in preferred antigenic compositions and vaccines of the present disclosure.

Surprised by the partial protective efficacy given that all anti-VLP Abs bound CS and competed with mAb 5D5 for binding to CS, we examined the fine specificity of the anti-VLP Abs compared to mAb 5D5 using a panel of alanine substituted peptides. The contact residues for mAb 5D5 were: $D^{82}$, $N^{83}$, $E^{84}$, $R^{87}$, $K^{90}$, $H^{91}$. Note that of the six lysines only $K^{90}$ was critical for mAb 5D5 binding. Analysis of anti-VLP sera revealed that fine specificity mapping was not as definitive, most likely due to the polyclonal nature of the anti-VLP sera. Nevertheless, distinct differences were apparent between anti-VLP sera and mAb 5D5. For example, the six residues critical for mAb 5D5 binding were variable and much less critical for anti-VLP sera binding as shown in Table 2-2. Interestingly, the inverse was true for anti-VLP and mAb 5D5 binding to the lysine-substituted peptides. Whereas, $K^{90}$ was the only lysine critical for mAb 5D5 binding, it was not necessary for binding by any of the anti-VLP sera, and conversely, the other five lysines were important for anti-VLP binding but not for mAb 5D5 binding. Note that the peptide in which five of the six lysines were substituted by alanines (except $K^{90}$) was recognized by mAb 5D5 (41% of WT peptide) and minimally by two anti-VLP sera and not at all by the other eight anti-VLP sera. Therefore, to more faithfully mimic the fine specificity of mAb 5D5, mutant CS(81-91) sequences were designed by substituting the five lysines with alanines to "re-direct" antibody production to the six known contact residues of mAb 5D5. The amino acid sequences of the multiply-substituted inserts and insert positions within the WHcAg are shown in Table 2-3.

TABLE 2-1

Initial 5D5 VLP Library

| VLP | Insert & position | VLP antigens 5D5 (ng/ml) Direct Binding to VLP (a) | α-CSP titer (1/dil) (b) | α-VLP Inhib 5D5-CSP 50% binding (c) | IFA (d) | ↓↓ Spzt Liver Load (0.25-0.3 ml passive) (e) |
|---|---|---|---|---|---|---|
| VLP245 | 81-91 @78 | 2.0 | 3M | 1:130K | 1:900 | 65% |
| VLP246 | 77-91 @78 | 4.0 | 625K | 1:30K | 1:2700 | — |
| VLP248 | 81-97 @78 | 90 | 125K | 1:3K | 1:900 | 0 |
| VLP249 | 81-91 @78 | 18 | 625K | 1:5K | 1:2700 | 0 |
| VLP250 | 77-91 @78 | 460 | 625K | 1:25K | 1:2700 | 37% |
| VLP251 | 81-94 @78 | 2300 | 125K | 1:5K | 1:900 | 20% |
| VLP255 | 81-94 @81 | 0.7 | 625K | 1:30K | 1:2700 | 35% |
| VLP256 | 81-97 @81 | 0.7 | 625K | 1:150K | 1:900 | 57% |
| VLP257 | 81-94 @Nterm | 0.7 | 625K | 1:25K | 1:900 | 55% |
| Krich | 72-94 @78 | 4.0 | 625K | 1:25K | 1:900 | 50% |

TABLE 2-2 anti-CS(81-95) VLP Antibody Specificity

| Peptide Panel | anti-"5D5" VLP Sera | | | | | | | | | K-rich | Mad 5D5 |
|---|---|---|---|---|---|---|---|---|---|---|---|
| | 245 | 246 | 249 | 250 | 248 | 251 | 255 | 256 | 257 | | |
| EANEKLRKPKHKKLKQP | ++ | + | +++ | + | +++ | ++ | +++ | +++ | ++ | - | + |
| EDAEKLRKPKHKKLKQP | - | + | +++ | - | ++ | + | ++ | ++ | ++ | - | - |
| EDNEALRKPKHKKLKQP | + | + | ++ | + | ++ | ++ | + | + | - | - | +++ |
| EDNEKLRKPAHKKLKQP | +++ | +++ | +++ | ++ | +++ | +++ | +++ | +++ | +++ | +++ | - |
| EDNEKLRKPKAKKLKQP | +++ | +++ | +++ | +++ | +++ | +++ | +++ | +++ | +++ | +++ | - |
| EDNEKLRAPKHKKLAQP | +++ | ++ | ++ | ++ | ++ | ++ | ++ | +++ | +++ | +++ | +++ |
| EDNEALRAPKHKKLAQP | ++ | + | - | - | - | - | - | - | - | - | +++ |
| EDNEALRAPKHAALAQP | - | - | - | - | + | + | - | - | - | - | ++ |

The amino acid sequences of the CS(81-95) peptide panel are set forth as SEQ ID NOs:72-79.

TABLE 2-3

Subsequent 5D5 VLP Library With Multiply-Substituted Inserts

| Insert Name | Insert Sequence | SEQ ID NO: | Position | VLP |
|---|---|---|---|---|
| CSP(81-97)2KA | EDNEALRAPKHKKLKQP | 80 | 81<br>N-term | 307<br>312 |
| CSP(81-97)3KA | EDNEALRAPKHKALKQP | 81 | 81<br>N-term | 308<br>313 |
| CSP(81-97)4KA93 | EDNEALRAPKHAALKQP | 82 | 81<br>N-term | 309<br>314 |
| CSP(81-97)4KA95 | EDNEALRAPKHAKLAQP | 83 | 81<br>N-term | 310<br>315 |
| CSP(81-97)5KA | EDNEALRAPKHAALAQP | 84 | 81<br>N-term | 311<br>316 |

VLP-313, VLP-314, and VLP-316 have been produced. These VLPs contain three, four and five K-to-A substitutions within aa 81-91, respectively, inserted at the N-terminus of WHcAg (Table 2-3). Although these VLPs may elicit alanine-dependent antibodies in addition to mAb 5D5-like antibodies, the alanine-dependent antibodies are less likely to cross-react with native CS and most importantly less likely to block mAb 5D5-like antibody activity. Preliminary evidence indicates that VLP-313, VLP-314, and VLP-316 are all recognized by mAb 5D5 and inhibit mAb 5D5 binding to CS equivalently to VLP-257, which contains the WT 81-94 sequence at the N-terminus of WHcAg. Importantly, anti-VLP-257 sera binding to CS is only inhibited by VLP-257 and not by VLP-313, VLP-314, and VLP-316. This indicates that while VLP-313, VLP-314, and VLP-316 have preserved the mAb 5D5 epitope, the lysine-dependent epitope(s) recognized by the polyclonal anti-VLP-257 sera have been functionally eliminated. Therefore, immunization with VLP-313, VLP-314, and VLP-316 is likely to elicit mAb 5D5-like antibodies as opposed to the lysine-dependent antibody responses elicited by full length CS or the VLPs carrying the non-mutated 81-91/97 sequences.

Example 3

Hybrid Woodchuck Hepadna Virus Core Antigens Containing a Malaria RH Epitope

Pf reticulocyte-binding protein homolog 5 (RH5) is a recently identified merozoite protein. The RH5 protein is known to mediate a critical non-redundant interaction with the human red blood cell surface protein basigin during invasion (Crosnier et al., Nature, 480:534-537, 2011). Antibodies induced by RH5 in mice and rabbits block erythrocyte invasion more efficiently than antibodies to all other known antigens and cross-inhibit all strains and field isolates tested to date. Most recently, a recombinant RH5 vaccine protected monkeys against a virulent heterologous *P. falciparum* challenge and the protection was associated with anti-RH5 Ab titer and in vitro parasite-neutralizing activity, indicating that the growth inhibition assay will be useful in predicting in vivo efficacy (Douglas et al., Cell Host Microbe, 17:130-139, 2015).

Several linear RH5 epitopes have been identified that are recognized by mAbs capable of blocking the RH5-basigin interaction and erythrocyte invasion in vitro. The minimal specificity of mAb QA5 was defined as RH5(200-213) and the minimal specificity of mAb 9AD4 was defined as RH5(353-361) (Williams, et al., PLoS Pathogen, 8:e1002991, 2012). Additionally, the minimal specificity of mAb 5A08 was defined as a mimetope sequence present in native RH5(25-36) (Ord et al., Maral J, 13:326, 2014). Based on the known neutralizing capabilities of these three mAbs, the minimal epitopes are displayed on the WHcAg carrier platform (see Table 4) as described for the CS-specific epitopes. Initial ELISAs of bacterial lysates using these three mAbs represent the first screen to determine WHcAg expression levels (WHc-conformation-independent mAb), VLP assembly (WHc-conformation-dependent mAb) and RH5 epitope antigenicity (RH5 mAb). Purified WHc-RH5 hybrid VLPs are also tested in a growth inhibition assay.

In a preliminary experiment the RH5(25-36) epitope inserted onto the WHcAg (VLP-270) elicited anti-RH5 antibodies capable of 75% inhibition in the growth inhibition assay at an IgG concentration of 1.0 mg/ml. Therefore, the presentation of these RH5 epitopes on hybrid VLPs is expected to yield candidates effective against the blood stage.

The disclosure of US Publication No. 2016-0022801 of Milich and Whitacre is hereby incorporated by reference in its entirety. In particular, the examples of US Publication No. 2016-0022801, are hereby incorporated by reference.

REFERENCES

1. Guerra et al., Trends Parasitol. 2006; 22: 353-358.
2. Murray et al., The Lancet. 2012; 379: 413-431.
3. Stoute et al., J Infect Dis. 1998; 178: 1139-44.
4. Webster et al., Proc Natl Acad Sci USA. 2005; 102: 4836-4841.
5. Gordon et al., J Infect Dis. 1995; 171: 1576-85.
6. Stoute et al., N Engl J Med. 1997; 336: 86-91.
7. Bojang et al., Lancet. 2001; 358: 1927-34.
8. Alloueche et al., Am J Trop Med Hyg. 2003; 68: 97-101.
9. Alonso et al., Lancet. 2004; 364: 1411-20.
10. Aponte et al., Lancet. 2007; 370: 1543-51.
11. Olotu et al., N Engl J Med. 2013; 368: 1111-1120.
12. Duffy et al., Expert Rev Vaccines. 2012; 11: 1261.
13. Schödel et al., J Exp Med. 1994; 180: 1037-46.
14. Schödel et al., Behring Inst Mitt. 1997; 98: 114-9.
15. Milich et al., Vaccine. 2001; 20: 771-88.
16. Persson et al., J Immunol. 2002; 169: 6681-5.
17. Espinosa et al., Infect Immun. 2013; 81: 2882-2887.
18. Billaud et al., J Virol. 2005; 79: 13656-66.
19. Aida and Pabst., J Immunol Methods. 1990; 132: 191-195.
20. Liu et al., Clin Biochem. 1997; 30: 455-463.
21. Whitacre et al., Chapter 13: Use of VLPs in the Design of Malaria Vaccines. In: Yury Khudyakov, Paul Pumpens, editors. Viral Nanotechnology. CRC Press; 2015. p. 536.
22. Cerami et al., Cell. 1992; 70: 1021-1033.
23. Cockburn et al., PLoS Pathog. 2011; 7: e1001318.
24. Ménard and Janse, Methods. 1997; 13: 148-157.
25. Bruña-Romero et al., Int J Parasitol. 2001; 31: 1499-1502.
26. Aley et al., J Exp Med. 1986; 164: 1915-22.
27. Rathore et al., J Biol Chem. 2005; 280: 20524-9.
28. White et al., Vaccine. 1993; 11: 1341-6.
29. Calle et al., J Immunol. 1992; 149: 2695-701.
30. Kumar et al., Nature. 2006; 444: 937-40.
31. Zavala et al., J Exp Med. 1983; 157: 1947-57.
32. Zavala et al., Science. 1985; 228: 1436-40.
33. Good et al., J Exp Med. 1986; 164: 655-660.
34. Good et al., Proc Natl Acad Sci. 1988; 85: 1199-1203.
35. White et al., PLoS One. 2013; 8: e61395.
36. Birkett et al., Infect Immun. 2002; 70: 6860-70.
37. Walther et al., Vaccine. 2005; 23: 857-64.
38. Billaud et al., Vaccine. 2007; 25: 1593-606.
39. Lee et al., J Immunol. 2009; 182: 6670-81.
40. Kaba et al., PLoS One. 2012; 7: e48304.
41. Kastenmüller et al., Infect Immun. 2013; 81: 789-800.
42. Porter et al., Clin Vaccine Immunol. 2013; 20: 803-10.
43. Przysiecki et al., Front Cell Infect Microbiol. 2012; 2: 146.
44. Tewari et al., J Biol Chem. 2002; 277: 47613-8.
45. Milich and McLachlan, Science. 1986; 234: 1398-401.
46. Hoofnagle et al., Lancet. 1973; 2: 869-73.
47. Betancourt et al., Int J Infect Dis. 2007; 11: 394-401.
48. Alper, Exp Clin Immunogenet. 1995; 12: 171-81
. Whitacre et al., PLoS One, 2015; 10(5): e0124856

EXEMPLARY EMBODIMENTS

1. An antigenic composition comprising a hybrid woodchuck hepadnavirus core antigen, wherein the hybrid core antigen is a fusion protein comprising a malaria antigen and a woodchuck hepadnavirus core antigen, the woodchuck hepadnavirus core antigen comprises the amino acid sequence of SEQ ID NO:12 or 14 the malaria antigen comprises a B cell domain of from 4 to 60 amino acids and length and a T cell domain of from 8 to 120 amino acids in length, the B cell domain is inserted at a first position and the T cell domain is inserted at a second position, and the first position is not adjacent to the second position within the core antigen, and the fusion protein is capable of assembling as a hybrid virus-like particle (VLP).

2. The antigenic composition of embodiment 1, wherein the first position is an internal position of the core antigen selected from the group consisting of 61, 71, 72, 73, 74, 75, 76, 77, 78, 81, 82, 83, 84, 85 and 92 as numbered according to SEQ ID NO:1, or wherein the first position is at position 78.

3. The antigenic composition of embodiment 1 or embodiment 2, wherein the second position is a terminal position of the core antigen selected from the group consisting of N-terminal, 149 (truncated C-terminal), 187 and 188 as numbered according to SEQ ID NO:1, or wherein the second position is at position 188.

4. The antigenic composition of embodiment 1, wherein the first position is 78 and the second position is 188.

5. The antigen composition of any of the preceding embodiments, wherein the core antigen is a modified woodchuck hepadnavirus core antigen comprising the amino acid sequence of SEQ ID NO:13, but does not comprise SEQ ID NO:1 or SEQ ID NO:11.

6. The antigenic composition of embodiment 5, wherein the modified woodchuck hepadnavirus comprises one of the amino acid sequences selected from the group consisting of SEQ ID NO:2, SEQ ID NO:3, SEQ ID NO:4, SEQ ID NO:5, SEQ ID NO:6 and SEQ ID NO:7, or wherein the modified woodchuck hepadnavirus core antigen comprises the amino acid sequence of SEQ ID NO:4 or a variant of SEQ ID NO:4 with a R164G substitution.

7. The antigenic composition of embodiment 5, wherein the modified woodchuck hepadnavirus core antigen comprises one, two, three, four or five modifications of the group consisting of:

Δ2=WHcAg/L21A, D26A, L27A, N28A, A29V, V31A substitutions;
Δ3=WHcAg/N136P, A137P substitutions;
Δ4=WHcAg/C61S substitution;
Δ5=WHcAg/replacement of residues 62-85, 65-88 or 64-87 with a heterologous antigen;
Δ6=WHcAg/R150A, R151A, R152A, R156A, R159A, R162A, R163A, R164A, R169A, R170A, R171A, R177A, R178A, R179A, R180A substitutions; and
Δ7=WHcAg/N75A, I76A, T77A, S78A, E79A, Q80A, V81A, R82A, T83A substitutions;
wherein the modifications are numbered according to SEQ ID NO:1.

8. The antigenic composition of any of the preceding embodiments, wherein the malaria antigen comprises a fragment of a circumsporozoite antigen of one or more parasite species selected from the group consisting of *P. falciparum, P. vivax, P. ovale* and *P. malariae*.

9. The antigenic composition of any of the preceding embodiments, wherein one or both of the B cell domain and the T cell domain is a fusion protein comprising fragments of two, three, four or five different polypeptides.

10. The antigenic composition of any of the preceding embodiments, wherein the B cell domain comprises the amino acid sequence of one or more of the group consisting of SEQ ID NOs:24-40 and 57-71, or wherein the B cell domain comprises the amino acid sequence of one or more of the group consisting of SEQ ID NOs:24-40.

11. The antigenic composition of any of the preceding embodiments, wherein the T cell domain comprises the amino acid sequence selected from the group consisting of SEQ ID NOs:41-50.

10. The antigenic composition of any of the preceding embodiments, wherein the B cell domain comprises the amino acid sequence of SEQ ID NO:24 or is at least 95% identical thereto.

11. The antigenic composition of any of the preceding embodiments, wherein the T cell domain comprises the amino acid sequence of SEQ ID NO:49 or is at least 95% identical thereto.

12. The antigenic composition of any of the preceding embodiments, wherein the T cell domain is inserted at the carboxy-terminal end of the core antigen as a linker/insert combination according to the formula [D]y[I]z–Xm in which both y and z are in integers independently selected from the group consisting of 0, 1, and 2, and wherein Xm is the T cell domain.

13. The antigenic composition of any of the preceding embodiments, wherein the hybrid woodchuck hepadnavirus core antigen comprises the amino acid sequence of SEQ ID NO:20 (VLP-162) or is at least 95% identical thereto.

14. The antigenic composition of any one of embodiments 8 to 13, wherein the hybrid VLP competes with a native, or recombinant soluble form of the circumsporozoite protein for binding to a circumsporozoite protein-specific antibody.

15. The antigenic composition of any one of embodiments 8 to 14, wherein the hybrid VLP elicits a high titer, antibody response against the circumsporozoite protein or against a sporozoite of a malaria parasite that expresses the circumsporozoite protein.

16. The antigenic composition of any one of embodiments 8 to 15, wherein the hybrid VLP elicits a measurable neutralizing antibody response against a sporozoite of a malaria parasite that expresses the circumsporozoite protein.

17. The antigenic composition of any one of embodiments 8 to 16, wherein the hybrid VLP elicits a protective immune response against blood stage malaria parasite infection.

18. The antigenic composition of any one of embodiments 8 to 17, wherein the hybrid VLP elicits a protective immune response against liver stage malaria parasite infection.

19. An antigenic composition comprising a hybrid woodchuck hepadnavirus core antigen, wherein
the hybrid core antigen is a fusion protein comprising a malaria antigen and a woodchuck hepadnavirus core antigen,
the woodchuck hepadnavirus core antigen comprises the amino acid sequence of SEQ ID NO:12 or 14,
the malaria antigen comprises a B cell domain of from 4 to 60 amino acids and length, the B cell domain is inserted at a position of the core antigen selected from the group consisting of 1, 61, 71, 72, 73, 74, 75, 76, 77, 78, 81, 82, 83, 84, 85, 92, 149, 187, and 188, as numbered according to SEQ ID NO:1, and
the fusion protein is capable of assembling as a hybrid virus-like particle (VLP).

20. The antigenic composition of embodiment 19, wherein the position is an internal position of the core antigen selected from the group consisting of 61, 71, 72, 73, 74, 75, 76, 77, 78, 81, 82, 83, 84, 85 and 92 as numbered according to SEQ ID NO:1, or wherein the position is at 78.

21. The antigen composition of embodiment 19 or embodiment 20, wherein the core antigen is a modified woodchuck hepadnavirus core antigen comprising the amino acid sequence of SEQ ID NO:13, but does not comprise SEQ ID NO:1 or SEQ ID NO:11.

22. The antigenic composition of embodiment 21, wherein the modified woodchuck hepadnavirus comprises one of the amino acid sequences selected from the group consisting of SEQ ID NO:2, SEQ ID NO:3, SEQ ID NO:4, SEQ ID NO:5, SEQ ID NO:6 and SEQ ID NO:7, or wherein the modified woodchuck hepadnavirus core antigen comprises the amino acid sequence of SEQ ID NO:4 or a variant of SEQ ID NO:4 with a R164G substitution.

23. The antigenic composition of embodiment 21, wherein the modified woodchuck hepadnavirus core antigen comprises one, two, three, four or five modifications of the group consisting of:
Δ2=WHcAg/L21A, D26A, L27A, N28A, A29V, V31A substitutions;
Δ3=WHcAg/N136P, A137P substitutions;
Δ4=WHcAg/C61S substitution;
Δ5=WHcAg/replacement of residues 62-85, 65-88 or 64-87 with a heterologous antigen;
Δ6=WHcAg/R150A, R151A, R152A, R156A, R159A, R162A, R163A, R164A, R169A, R170A, R171A, R177A, R178A, R179A, R180A substitutions; and
Δ7=WHcAg/N75A, I76A, T77A, S78A, E79A, Q80A, V81A, R82A, T83A substitutions;
wherein the modifications are numbered according to SEQ ID NO:1.

24. The antigenic composition of any one of embodiments 19-23, wherein the malaria antigen comprises a fragment of a reticulocyte-binding protein homolog 5 (RH5) of one or more parasite species selected from the group consisting of *P. falciparum, P. vivax, P. ovale* and *P. malariae*.

25. The antigenic composition of embodiment 24, wherein the B cell domain comprises the amino acid sequence of one or more of the group consisting of SEQ ID NOs:37, 38, 39, 40, 66, 67 and 68.

26. The antigenic composition of embodiment 24, wherein the B cell domain comprises the amino acid sequence of SEQ ID NO:37 or is at least 95% identical thereto.

27. The antigenic composition of embodiment 24, wherein the hybrid woodchuck hepadnavirus core antigen comprises the amino acid sequence of SEQ ID NO:87 (VLP-270) or is at least 95% identical thereto.

28. The antigenic composition of any one of embodiments 19-23, wherein the malaria antigen comprises a fragment of a circumsporozoite antigen of one or more parasite species selected from the group consisting of *P. falciparum, P. vivax, P. ovale* and *P. malariae*.

29. The antigenic composition of embodiment 28, wherein the B cell domain comprises the amino acid sequence of one of the group consisting of SEQ ID NOs: 33-36, 57-65 and 71.

30. The antigenic composition of embodiment 28, wherein the B cell domain comprises the amino acid sequence of SEQ ID NO:33 or is at least 95% identical thereto.

31. The antigenic composition of embodiment 28, wherein the hybrid woodchuck hepadnavirus core antigen comprises the amino acid sequence of SEQ ID NO:86 (VLP-245) or is at least 95% identical thereto.

32. The antigenic composition of any one of embodiments 19-23, wherein the malaria antigen comprises a fragment of a circumsporozoite antigen of *P. vivax*.

33. The antigenic composition of embodiment 32, wherein the B cell domain comprises the amino acid sequence of one or both of SEQ ID NO:69 and SEQ ID NO:70.

34. The antigenic composition of embodiment 32, wherein the B cell domain comprises the amino acid sequence of SEQ ID NO:69 or is at least 95% identical thereto.

35. The antigenic composition of embodiment 32, wherein the hybrid woodchuck hepadnavirus core antigen comprises the amino acid sequence of SEQ ID NO:85 (VLP-206) or is at least 95% identical thereto.

36. The antigenic composition of any one of the preceding embodiments, wherein the composition comprises a combination of two, three, four, or five different hybrid VLPs.

37. The antigenic composition of embodiment 36, wherein the combination of different hybrid VLPs comprises a first VLP and a second VLP, wherein the first VLP is of the antigen composition of embodiment 1, the second VLP is of the antigenic composition of embodiment 24.

38. The antigen composition of embodiment 36, wherein the combination of different hybrid VLPs comprises a first VLP and a second VLP, wherein the first VLP is of the antigen composition of embodiment 1, and the second VLP is of the antigenic composition of embodiment 32.

37. The antigenic composition of embodiment 36, wherein the combination of different hybrid VLPs comprises a first VLP, a second VLP, and a third VLP, wherein the first VLP is of the antigen composition of embodiment 1, the second VLP is of the antigenic composition of embodiment 24, and the third VLP is of the antigenic composition of embodiment 32.

38. The antigenic composition of embodiment 36, wherein the combination of different hybrid VLPs comprises a first VLP, a second VLP, and a third VLP, wherein the first VLP is of the antigen composition of embodiment 13, the second VLP is of the antigenic composition of embodiment 27, and the third VLP is of the antigenic composition of embodiment 35.

39. The antigenic composition of embodiment 36, wherein the combination of different hybrid VLPs comprises a first VLP and a second VLP, and a third VLP, wherein the first VLP comprises a fragment of a *P. falciparum* circumsporozoite antigen, the second VLP comprises a fragment of a *P. vivax* circumsporozoite antigen, and the third VLP comprises a fragment of a *P. falciparum* reticulocyte-binding protein homolog 5.

40. A vaccine comprising the antigenic composition of any one of the preceding embodiments, and an adjuvant.

41. A method for eliciting a malaria antigen-reactive antibody response, comprising administering to a mammal an effective amount of the vaccine of embodiment 40.

42. A method for reducing malaria parasite infection or preventing malaria in a mammal in need thereof, comprising administering to the mammal an effective amount of the vaccine of embodiment 40 according to a vaccine regimen comprising an initial immunization and one or more subsequent immunizations.

43. A polynucleotide encoding the hybrid woodchuck hepadnavirus core antigen of any one of embodiments 1 to 35.

44. An expression construct comprising the polynucleotide of embodiment 43 in operable combination with a promoter.

45. An expression vector comprising the expression construct of embodiment 44, for expression of the hybrid woodchuck hepadnavirus core antigen in bacterial cells or yeast cells.

46. A host cell comprising the expression vector of embodiment 45.

47. A method for screening anti-malaria antigen antibodies comprising:
a) measuring binding of an antibody or fragment thereof to the hybrid woodchuck hepadnavirus core antigen of any one of embodiments 1 to 35;
b) measuring binding of the antibody or fragment thereof to a woodchuck hepadnavirus core antigen devoid of the malaria antigen; and
c) determining that the antibody or fragment thereof is specific for the malaria antigen when the antibody or fragment thereof binds to the hybrid core antigen but not the core antigen devoid of the malaria antigen.

Sequences (Not Already Listed Above)

```
>WHcAg full length
                                                         SEQ ID NO: 1
MDIDPYKEFGSSYQLLNFLPLDFFPDLNALVDTATALYEEELTGREHCSPHHTAIRQALVCWDELTKLIAWMSS
NITSEQVRTIIVNHVNDTWGLKVRQSLWFHLSCLTFGQHTVQEFLVSFGVWIRTPAPYRPPNAPILSTLPEHTV
IRRRGGARASRSPRRRTPSPRRRRSQSPRRRRSQSPSANC >WHcAg Δ2
                                                         SEQ ID NO: 2
MDIDPYKEFGSSYQLLNFLPADFFPAAAVLADTATALYEEELTGREHCSPHHTAIRQALVCWDELTKLIAWMSS
NITSEQVRTIIVNHVNDTWGLKVRQSLWFHLSCLTFGQHTVQEFLVSFGVWIRTPAPYRPPNAPILSTLPEHTV
IRRRGGARASRSPRRRTPSPRRRRSQSPRRRRSQSPSANC
```

-continued

>WHcAg Δ3
SEQ ID NO: 3
MDIDPYKEFGSSYQLLNFLPLDFFPDLNALVDTATALYEEELTGREHCSPHHTAIRQALVCWDELTKLIAWMSS
NITSEQVRTIIVNHVNDTWGLKVRQSLWFHLSCLTFGQHTVQEFLVSFGVWIRTPAPYRPPPPPILSTLPEHTV
IRRRGGARASRSPRRRTPSPRRRRSQSPRRRRSQSPSANC

>WHcAg Δ4
SEQ ID NO: 4
MDIDPYKEFGSSYQLLNFLPLDFFPDLNALVDTATALYEEELTGREHCSPHHTAIRQALVSWDELTKLIAWMSS
NITSEQVRTIIVNHVNDTWGLKVRQSLWFHLSCLTFGQHTVQEFLVSFGVWIRTPAPYRPPNAPILSTLPEHTV
IRRRGGARASRSPRRRTPSPRRRRSQSPRRRRSQSPSANC

>WHcAg Δ5
SEQ ID NO: 5
MDIDPYKEFGSSYQLLNFLPLDFFPDLNALVDTATALYEEELTGREHCSPHHTAIRQALVCXXXXXXXXXXXXX
XXXXXXXXXXXXXHVNDTWGLKVRQSLWFHLSCLTFGQHTVQEFLVSFGVWIRTPAPYRPPNAPILSTLPEHTV
IRRRGGARASRSPRRRTPSPRRRRSQSPRRRRSQSPSANC

>WHcAg Δ6
SEQ ID NO: 6
MDIDPYKEFGSSYQLLNFLPLDFFPDLNALVDTATALYEEELTGREHCSPHHTAIRQALVCWDELTKLIAWMSS
NITSEQVRTIIVNHVNDTWGLKVRQSLWFHLSCLTFGQHTVQEFLVSFGVWIRTPAPYRPPNAPILSTLPEHTV
IAAAGGAAASASPAAATPSPAAARSQSPAAAASQSPSANC

>WHcAg Δ7

SEQ ID NO: 7

MDIDPYKEFGSSYQLLNFLPLDFFPDLNALVDTATALYEEELTGREHCSPHHTAIRQALVCWDELTKLIAWMSS
AAAAAAAAAIIVNHVNDTWGLKVRQSLWFHLSCLTFGQHTVQEFLVSFGVWIRTPAPYRPPNAPILSTLPEHTV
IRRRGGARASRSPRRRTPSPRRRRSQSPRRRRSQSPSANC

>GScAg

SEQ ID NO: 8

MDIDPYKEFGSSYQLLNFLPLDFFPDLNALVDTAAALYEEELTGREHCSPHHTAIRQALVCWEELTRLITWMSE
NTTEEVRRIIVDHVNDTWGLKVRQTLWFHLSCLTFGQHTVQEFLVSFGVWIRTPAPYRPPNAPILSTLPEHTVI
RRRGGSRAARSPRRRTPSPRRRRSQSPRRRRSQSPASNC

>AGScAg

SEQ ID NO: 9

MDIDPYKEFGSSYQLLNFLPLDFFPELNALVDTATALYEEELTGREHCSPHHTAIRQALVCWEELTRLIAWMSA
NINSEEVRRVIVAHVNDTWGLKVRQNLWFHLSCLTFGQHTVQEFLVSFGVRIRTPAPYRPPNAPILSTLPEHTV
IRRRGSARVVRSPRRRTPSPRRRRSQSPRRRRQSPASNC

>HBcAg

SEQ ID NO: 10

MDIDPYKEFGATVELLSFLPSDFFPSVRDLLDTASALYREALESPEHCSPHHTALRQAILCWGELMTLATWVGV
NLEDPASRDLVVSYVNTNMGLKFRQLLWFHISCLTFGRETVIEYLVSFGVWIRTPPAYRPPNAPILSTLPETTV
VRRRGRSPRRRTPSPRRRRSQSPRRRRSQSRESQC

>WHcAg truncated

SEQ ID NO: 11

MDIDPYKEFGSSYQLLNFLPLDFFPDLNALVDTATALYEEELTGREHCSPHHTAIRQALVCWDELTKLIAWMSS
NITSEQVRTIIVNHVNDTWGLKVRQSLWFHLSCLTFGQHTVQEFLVSFGVWIRTPAPYRPPNAPILSTLPEHTV
I

>WHcAg dB truncated (X is any amino acid or missing)

SEQ ID NO: 12

MDIDPYKEFG SSYQLLNFLP XDFFPXXXXL XDTATALYEE ELTGREHCSP HHTAIRQALV

XXXXXXXXXX XXXXXXXXXX XXXXXXXHVN DTWGLKVRQS LWFHLSCLTF GQHTVQEFLV

SFGVWIRTPA PYRPPXXPIL STLPEHTVIX XXXXXXXXXX XXXXXXXXXX XXXXXXXXXX

XXXXXXXX

>WHcAg dB full length (X is any amino acid or missing)

SEQ ID NO: 13

MDIDPYKEFG SSYQLLNFLP XDFFPXXXXL XDTATALYEE ELTGREHCSP HHTAIRQALV

XXXXXXXXXX XXXXXXXXXX XXXXXXXHVN DTWGLKVRQS LWFHLSCLTF GQHTVQEFLV

SFGVWIRTPA PYRPPXXPIL STLPEHTVIX XXGGAXASXS PXXXTPSPXX XRSQSPXXXX

SQSPSANC

>WHcAg hybrid dB and dC

SEQ ID NO: 14

MDIDPYKEFG SSYQLLNFLP XDFFPXXXXL XDTATALYEE ELTGREHCSP HHTAIRQALV

XXXXXXXXXX XXXXXXXXXX XXXXXXXHVN DTWGLKVRQS LWFHLSCLTF GQHTVQEFLV

SFGVWIRTPA PYRPPXXPIL STLPEHTVIX XXGGAXASXS PXXXTPSPXX XRSQSPXXXX

SQSPSANX

>WHcAg CDS

SEQ ID NO: 15

ATGGACATAGATCCCTATAAAGAATTTGGTTCATCTTATCAGTTGTTGAATTTTCTTCCTTTGGACTTCT

TTCCTGACCTTAATGCTTTGGTGGACACTGCTACTGCCTTGTATGAAGAAGAGCTAACAGGTAGGGAACA

TTGCTCTCCGCACCATACAGCTATTAGACAAGCTTTAGTATGCTGGGATGAATTAACTAAATTGATAGCT

TGGATGAGCTCTAACATAACTTCTGAACAAGTAAGAACAATCATAGTAAATCATGTCAATGATACCTGGG

GACTTAAGGTGAGACAAAGTTTATGGTTTCATTTGTCATGTCTCACTTTTGGACAACATACAGTTCAAGA

ATTTTTAGTAAGTTTTGGAGTATGGATCAGAACTCCAGCTCCATATAGACCTCCTAATGCACCCATTCTC

TCGACTCTTCCGGAACATACAGTCATTAGGAGAAGAGGAGGTGCAAGAGCTTCTAGGTCCCCCAGAAGAC

GCACTCCCTCTCCTCGCAGGAGAAGATCTCAATCACCGCGTCGCAGACGCTCTCAATCTCCATCTGCCAA

CTGCTGA

>WHV genome

SEQ ID NO: 16

```
   1   aattcgggac ataccacgtg gtttagttcc gcctcaaact ccaacaaatc gagatcaagg
  61   gagaaagcct actcctccaa ctccacctct aagagatact caccccccact taactatgaa
 121   aaatcagact tttcatctcc aggggttcgt agacggatta cgagacttga caacaacgga
 181   acgccaacac aatgcctatg agatcctttt acaacactag cccctgcgg ttcctactgt
 241   atccaccata ttgtctcctc cctcgacgac tggggaccct gcactgtcac cggagatgtc
 301   accatcaagt ctcctaggac tcctcgcagg attacaggtg gtgtattct tgtggacaaa
 361   aatcctaaca atagctcaga atctagattg gtggtggact ctctcagtt ttccaggggg
 421   cataccagag tgcactggcc aaaattcgca gttccaaact tgcaaacact tgccaacctc
 481   ctgtccacca acttgcaatg gctttcgttg gatgtatctg cggcgtttta tcatatacct
 541   attagtcctg ctgctgtgcc tcatcttctt gttggttctc ctggactgga aaggtttaat
 601   acctgtctgt cctcttcaac ccacaacaga acaacagtc aattgcagac aatgcacaat
 661   ctctgcacaa gacatgtata ctcctcctta ctgttgttgt ttaaaaccta cggcaggaaa
 721   ttgcacttgt tggcccatcc cttcatcatg ggctttagga aattacctat gggagtgggc
 781   cttagcccgt ttctcttggc tcaatttact agtgcccttg cttcaatggt taggaggaat
 841   ttccctcatt gcgtggtttt tgcttatatg gatgatttgg ttttggggc ccgcacttct
 901   gagcatctta ccgccattta ttcccatatt tgttctgttt ttcttgattt gggtatacat
 961   ttgaatgtca ataaaacaaa atggtggggc aatcatctac atttcatggg atatgtgatt
1021   actagttcag gtgtattgcc acaagacaaa catgttaaga aaatttcccg ttatttgcgc
1081   tctgttcctg ttaatcaacc tctggattac aaaaatttgtg aaagattgac tggtattctt
1141   aactatgttg ctccttttac gctatgtgga tacgctgctt taatgccttt gtatcatgct
1201   attacttccc gtacggcttt cattttctcc tccttgtata atcctggtt gctgtctctt
1261   tatgaggagt tgtggcccgt tgtcaggcaa cgtggcgtgg tgtgcactgt gtttgctgac
1321   gcaaccccca ctggttgggg cattgccacc acctatcaac tccttttccgg gactttcgct
1381   ttccccctcc ctattgccac ggcggaactc attgccgcct gccttgcccg ctgctggaca
1441   ggggctcggc tgttgggcac tgacaattcc gtggtgttgt cggggaagct gacgtccttt
1501   ccatggctgc tcgcctgtgt tgccaactgg attctgcgcg ggacgtcctt ctgctacgtc
1561   ccttcggccc tcaatccagc ggaccttcct tcccgcggcc tgctgccggt tctgcggcct
1621   cttccgcgtc ttcgccttcg ccctcagacg agtcggatct cccttgggc cgcctcccg
```

```
1681    cctgtttcgc ctcggcgtcc ggtccgtgtt gcttggtctt cacctgtgca gaattgcgaa
1741    ccatggattc caccgtgaac tttgtctcct ggcatgcaaa tcgtcaactt ggcatgccaa
1801    gtaaggacct tggactcct tatataaaag atcaattatt aactaaatgg gaggagggca
1861    gcattgatcc tagattatca atatttgtat taggaggctg taggcataaa tgcatgcgac
1921    ttctgtaacc atgtatcttt ttcacctgtg ccttgttttt gcctgtgttc catgtcctac
1981    ttttcaagcc tccaagctgt gccttggatg gctttgggc atggacatag atccctataa
2041    agaatttggt tcatcttatc agttgttgaa ttttcttcct ttggacttct ttcctgacct
2101    taatgctttg gtggacactg ctactgcctt gtatgaagaa gagctaacag gtagggaaca
2161    ttgctctccg caccatacag ctattagaca agctttagta tgctgggatg aattaactaa
2221    attgatagct tggatgagct caacataac ttctgaacaa gtaagaacaa tcatagtaaa
2281    tcatgtcaat gatacctggg gacttaaggt gagacaaagt ttatggtttc atttgtcatg
2341    tctcactttt ggacaacata cagttcaaga attttttagta agttttggag tatggatcag
2401    aactccagct ccatatagac ctcctaatgc acccattctc tcgactcttc cggaacatac
2461    agtcattagg agaagaggag gtgcaagagc ttctaggtcc cccagaagac gcactccctc
2521    tcctcgcagg agaagatctc aatcaccgcg tcgcagacgc tctcaatctc catctgccaa
2581    ctgctgatct tcaatgggta cataaaacta atgctattac aggtctttac tctaaccaag
2641    ctgctcagtt caatccgcat tggattcaac ctgagtttcc tgaacttcat ttacataatg
2701    atttaattca aaaattgcaa cagtattttg gtcctttgac tataaatgaa aagagaaaat
2761    tgcaattaaa ttttcctgcc agatttttcc ccaaagctac taaatatttc cctttaatta
2821    aaggcataaa aaacaattat cctaattttg ctttagaaca tttctttgct accgcaaatt
2881    atttgtggac tttatgggaa gctggaattt tgtatttaag gaagaatcaa acaactttga
2941    cttttaaagg taaaccatat tcttgggaac acagacagct agtgcaacat aatgggcaac
3001    aacataaaag tcaccttcaa tccagacaaa atagcagcat ggtggcctgc agtgggcact
3061    tattacacaa ccacttatcc tcagaatcag tcagtgtttc aaccaggaat ttatcaaaca
3121    acatctctga taaatcccaa aaatcaacaa gaactggact ctgttcttat aaacagatac
3181    aaacagatag actggaacac ttggcaagga tttcctgtgg atcaaaaatt accattggtc
3241    agcagggatc tcccccaaa accttatata aatcaatcag ctcaaacttt cgaaatcaaa
3301    cctgggccta taatagttcc cgg
```

>internal linker/insert combination  
SEQ ID NO: 17  
GIL-Xn-L  
where X is any amino acid, n is 60 or less >N-terminal linker  
SEQ ID NO: 18  
Xn-WLWG  
where Xn is an insert, X is any amino acid, and n is 60 or less >Malaria epitope  
SEQ ID NO: 19  
NANP NVDP NANP NANP NANP >VLP-162  
SEQ ID NO: 20  
MDIDPYKEFGSSYQLLNFLPLDFFPDLNALVDTATALYEEELTGREHCSPHHTAIRQALV  
SWDELTKLIAWMSSNITSGILNANPNVDPNANPNANPNANPLEQVRTIIVNHVNDTWGLK  
VRQSLWFHLSCLTFGQHTVQEFLVSFGVWIRTPAPYRPPNAPILSTLPEHTVIRRRGGAR  
ASRSPRRGTPSPRRRRSQSPRRRRSQSPSANCDIEYLNKIQNSLSTEWSPCSVTSGNGIQ  
VRIKPGSANKPKDELDYENDIEKKICKMEKCSSV >Hybrid CSP                                                                    SEQ ID NO: 21

MKKCTILVVA SLLLVNSLLP GYGQNKSIQA QRNLNELCYN EGNDNKLYHV    50

LNSKNGKIYN RNTVNRLLAD APEGKKNEKK NEKIERNNKL KQPPPPPNPN   100

DPPPPNPNDP PPPNPNDPPP PNPNDPPPPN ANDPPPPNAN DPAPPNANDP   150

APPNANDPAP PNANDPAPPN ANDPPPPNPN DPAPPNANDP PPPNPNDPAP   200

PQGNNNPQPQ PRPQPQPQPQ PQPQPQPQPQ PRPQPQPQPG GNNNNKNNNN   250

DDSYIPSAEK ILEYLNKIQN SLSTEWSPCS VTCGNGIQVR IKPGSANKPK   300

DELDYENDIE KKICKMEKCS SVFNVVNSSI GLIMVLSFLF LN           342

>VLP-206                                                                       SEQ ID NO: 85

MDIDPYKEFGSSYQLLNFLPLDFFPDLNALVDTATALYEEELTGREHCSPHHTAIRQALV

CWDELTKLIAWMSSNITSGILDRADGQPAGDRADGQPAGDRAAGQPAGDLE

QVRTIIVNHVNDTWGLKVRQSLWFHLSCLTFGQHTVQEFLVSFGVWIRTPAPYRPPNAPI

LSTLPEHTVIRRGGARASRSPRRRTPSPRRRRSQSPRRRRSQSPSANC

>VLP-245                                                                       SEQ ID NO: 86

MDIDPYKEFGSSYQLLNFLPLDFFPDLNALVDTATALYEEELTGREHCSPHHTAIRQALV

CWDELTKLIAWMSSNITSGILEEDNEKLRKPKHELEQVRTIIVNHVNDTWGLKVRQSLWF

HLSCLTFGQHTVQEFLVSFGVWIRTPAPYRPPNAPILSTLPEHTVIRRGGARASRSPRR

RTPSPRRRRSQSPRRRRSQSPSANC

>VLP-270                                                                       SEQ ID NO: 87

MDIDPYKEFGSSYQLLNFLPLDFFPDLNALVDTATALYEEELTGREHCSPHHTAIRQALV

CWDELTKLIAWMSSNITSGILEENAIKKTKNQEELEQVRTIIVNHVNDTWGLKVRQSLWF

HLSCLTFGQHTVQEFLVSFGVWIRTPAPYRPPNAPILSTLPEHTVIRRGGARASRSPRR

RTPSPRRRRSQSPRRRRSQSPSANC

---

We claim:

1. An antigenic composition comprising a hybrid woodchuck hepadnavirus core antigen, wherein
   the hybrid core antigen is a fusion protein comprising a malaria antigen and a woodchuck hepadnavirus core antigen, the woodchuck hepadnavirus core antigen is a modified woodchuck hepadnavirus core antigen comprising the amino acid sequence of SEQ ID NO:14 with a serine at position 61, the malaria antigen comprises a B cell domain of from 20 to 60 amino acids in length and a T cell domain of from 30 to 120 amino acids in length, the B cell domain is inserted at position 78 and the T cell domain is inserted at position 188 as numbered according to SEQ ID NO:1, and the fusion protein is capable of assembling as a hybrid virus-like particle (VLP).

2. The antigenic composition of claim 1, wherein the modified woodchuck hepadnavirus core antigen comprises the amino acid sequence of SEQ ID NO:4.

3. The antigenic composition of claim 1, wherein the malaria antigen comprises a fragment of a circumsporozoite antigen of one or more parasite species selected from the group consisting of *P. falciparum, P. vivax, P. ovale* and *P. malariae.*

4. The antigenic composition of claim 1, wherein one or both of the B cell domain and the T cell domain is a fusion protein comprising fragments of two, three, four or five different polypeptides.

5. The antigenic composition of claim 1, wherein the B cell domain comprises the amino acid sequence of SEQ ID NO:24 or the amino acid sequence at least 95% identical thereto.

6. The antigenic composition of claim 1, wherein the T cell domain comprises the amino acid sequence of SEQ ID NO:49 or the amino acid sequence at least 95% identical thereto.

7. The antigenic composition of claim 1, wherein the T cell domain is inserted as a linker/insert combination according to the formula [D]y[I]z–Xm in which both y and z are 1, and Xm is the T cell domain.

8. The antigenic composition of claim 1, wherein the hybrid woodchuck hepadnavirus core antigen comprises the amino acid sequence of SEQ ID NO:20 or the amino acid sequence at least 95% identical thereto.

9. The antigenic composition of claim 1, wherein
the B cell domain comprises the amino acid sequence of SEQ ID NO:24,
the T cell domain comprises the amino acid sequence of SEQ ID NO:49, and
the hybrid VLP competes with a native, or recombinant soluble form of the circumsporozoite protein for binding to a circumsporozoite protein-specific antibody.

10. The antigenic composition of claim 9, wherein the hybrid VLP elicits a high titer, antibody response against the circumsporozoite protein or against a sporozoite of a malaria parasite that expresses the circumsporozoite protein.

11. The antigenic composition of claim 9, wherein the hybrid VLP elicits a measurable neutralizing antibody response against a sporozoite of a malaria parasite that expresses the circumsporozoite protein.

12. The antigenic composition of claim 9, wherein the hybrid VLP elicits a protective immune response against blood stage malaria parasite infection.

13. The antigenic composition of claim 9, wherein the hybrid VLP elicits a protective immune response against liver stage malaria parasite infection.

14. A vaccine comprising the antigenic composition of claim 1, and an adjuvant.

15. A method for eliciting a malaria antigen-reactive antibody response, comprising administering to a mammal an effective amount of the vaccine of claim 14.

16. A method for reducing malaria parasite infection or preventing malaria in a mammal in need thereof, comprising administering to the mammal an effective amount of the vaccine of claim 14 according to a vaccine regimen comprising an initial immunization and one or more subsequent immunizations.

17. An expression construct comprising a polynucleotide encoding the hybrid woodchuck hepadnavirus core antigen of claim 1 in operable combination with a promoter.

18. An expression vector comprising the expression construct of claim 17, for expression of the hybrid woodchuck hepadnavirus core antigen in bacterial cells or yeast cells.

19. A host cell comprising the expression vector of claim 18.

20. A method for screening anti-malaria antigen antibodies comprising:
a) measuring binding of an antibody or fragment thereof to the hybrid woodchuck hepadnavirus core antigen of claim 1;
b) measuring binding of the antibody or fragment thereof to a woodchuck hepadnavirus core antigen devoid of the malaria antigen; and
c) determining that the antibody or fragment thereof is specific for the malaria antigen when the antibody or fragment thereof binds to the hybrid core antigen but not the core antigen devoid of the malaria antigen.

* * * * *